United States Patent
Hunt et al.

(10) Patent No.: US 6,982,265 B1
(45) Date of Patent: *Jan. 3, 2006

(54) PYRROLOTRIAZINE INHIBITORS OF KINASES

(75) Inventors: John T. Hunt, Princeton, NJ (US);
Rajeev S. Bhide, Langhorne, PA (US);
Robert Michael Borzilleri, New Hope, PA (US); Ligang Qian, Hopewell, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/573,829

(22) Filed: May 18, 2000

Related U.S. Application Data

(60) Provisional application No. 60/135,265, filed on May 21, 1999, provisional application No. 60/193,727, filed on Mar. 31, 2000.

(51) Int. Cl.
*C07D 487/04* (2006.01)
*A61K 31/153* (2006.01)
*A61P 35/00* (2006.01)
*A61P 27/02* (2006.01)
*A61P 29/00* (2006.01)

(52) U.S. Cl. ............ 514/243; 544/183; 548/530; 548/532

(58) Field of Classification Search ............ 514/234.5, 514/243; 544/111, 112, 183
See application file for complete search history.

(56) References Cited

U.S. PATENT DOCUMENTS

| | | |
|---|---|---|
| 4,908,056 A | 3/1990 | Tseng ........................ 71/90 |
| 5,686,457 A | 11/1997 | Traxler et al. |
| 6,670,357 B2 * | 12/2003 | Leftheris et al. ............ 514/218 |
| 6,787,545 B1 * | 9/2004 | Ohtani et al. ............ 514/243 |
| 6,867,300 B2 * | 3/2005 | Godfrey et al. ............ 544/183 |
| 6,869,952 B2 * | 3/2005 | Bhide et al. ............ 514/243 |
| 2003/0069244 A1 * | 4/2003 | Leftheris et al. ............ 514/243 |
| 2005/0009823 A1 * | 1/2005 | Chen ............ 514/243 |
| 2005/0043306 A1 * | 2/2005 | Leftheris et al. ............ 514/243 |

FOREIGN PATENT DOCUMENTS

| | | |
|---|---|---|
| EP | 778 277 A1 | 6/1997 |
| EP | 0 795 556 A1 | 9/1997 |
| WO | WO 98/08847 | 3/1998 |
| WO | WO 01/14378 A1 | 3/2001 |

OTHER PUBLICATIONS

Ewald H. et. al., "Reactionen von 1,2,4-Triazinen mit Acetylendicarbonsaure-dimethylester". Justus Liebigs Annalen Der Chemie, (1977), vol. 10, pp. 1718-1724.*
Migliara, J. Het. Chem 16, 833 (1979).*
Otter et al, Nucleoside & Nucleotides, 15(1-3), 793-807 (1996).
Quintela et al, Tetrahedron, 52(8), 3037-3048 (1996) .
Patil et al, J. Heterocyclic Chem., 31(4), 781-807 (1994) .
Neunhoeffer et al, Justus Liebigs Ann. Chem., vol. 9, 1413-1420 (1977) & Chem. Abstr. 88:121113q, (Apr. 1978) .
Skobe et al, Nature Medicine, vol. 3, No. 11, 1223-1227 (Nov. 1997) .

* cited by examiner

*Primary Examiner*—Mark L. Berch
(74) *Attorney, Agent, or Firm*—Elliott Korsen

(57) ABSTRACT

The present invention provides compounds of formula I

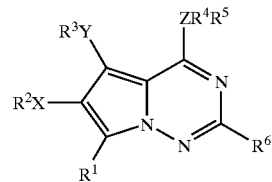

and pharmaceutically acceptable salts thereof.

The formula I compounds inhibit the tyrosine kinase activity of growth factor receptors such as VEGFR-2, FGFR-1, PDGFR, HER-1, HER-2, thereby making them useful as anti-cancer agents. The formula I compounds are also useful for the treatment of other diseases associated with signal transduction pathways operating through growth factor receptors.

9 Claims, No Drawings

PYRROLOTRIAZINE INHIBITORS OF KINASES

RELATED APPLICATIONS

This application claims priority benefit under Title 35 § 19 (e) of U.S. provisional Application No. 60/135,265, filed May 21, 1999, and U.S. provisional Application No. 60/193,727, filed Mar. 31, 2000.

FIELD OF THE INVENTION

This invention relates to compounds that inhibit the tyrosine kinase activity of growth factor receptors such as VEGFR-2, FGFR-1, PDGFR, HER1, and HER2, thereby making them useful as anti-cancer agents. The compounds are also useful in the treatment of diseases, other than cancer, which are associated with signal transduction pathways operating through growth factor receptors such as VEGFR-2.

BACKGROUND OF THE INVENTION

Normal angiogenesis plays an important role in a variety of processes including embryonic development, wound healing, obesity and several components of female reproductive function. Undesirable or pathological angiogenesis had been associated with disease states including diabetic retinopathy, psoriasis, cancer, rheumatoid arthritis, atheroma, Kaposi's sarcoma and haemangioma (Fan et al, 1995, Trend Pharmacol. Sci. 16: 57–66; Folkman, 1995, Nature Medicine 1: 27–31). Alteration of vascular permeability is thought to play a role in both normal and pathophysiological processes (Cullinan-Bove et al, 1993,, Endocrinology 133: 829–837; Senger et al, 1993 Cancer and Metastasis Reviews, 12: 303–324).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1 (VEGFR-1), the kinase insert domain-containing receptor, KDR (also referred to as Flk-1 or VEGFR-2), and another fms-like tyrosine kinase receptor, Flt4 (VEGFR-3). Two of these related RTKs, Flt and KDR, have been shown to bind vascular endothelial growth factor (VEGF) with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells had been associated with changes in the tyrosine phosphorylation status of cellular proteins and calcium fluxes. VEGF, along with acidic and basic fibroblast growth factor (aFGF & bFGF) have been identified as having in vitro endothelial cell growth promoting activity. By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36: 139–155) and vascular permeability (Connolly et al, 1989, J. Biol. Chem. 264: 20017–20024).

In adults, endothelial cells have a low proliferation index except in cases of tissue remodeling, such as wound healing and the female reproductive cycle, and adipogenesis. However in pathological states such as cancer, inherited vascular diseases, endometriosis, psoriasis, arthritis, retinopathies and atherosclerosis, endothelial cells are actively proliferating and organizing into vessels. Upon exposure to angiogenic stimuli with growth factors such as VEGF and bFGF, endothelial cells re-enter the cell cycle, proliferate, migrate and organize into a three-dimensional network. The ability of tumors to expand and metastasize is dependent upon the formation of this vascular network.

Binding of VEGF or bFGF to their corresponding receptor results in dimerization, autophosphorylation on tyrosine residues and enzymatic activation. These phosphotyrosine residues serve as "docking" sites for specific downstream signaling molecules and enzymatic activation results in proliferation of endothelial cells. Disruption of these pathways should inhibit endothelial cell proliferation. Disruption of the FGFR-1 pathway should also affect tumor cell proliferation since this kinase is activated in many tumor types in addition to proliferating endothelial cells. Finally, recent evidence also suggests that disruption of VEGF signaling inhibits endothelial cell migration, a critical process in vascular network formation.

The over-expression and activation of VEGFR-2 and FGFR-1 in tumor-associated vasculature has suggested a role for these molecules in tumor angiogenesis. Angiogenesis and subsequent tumor growth is inhibited by antibodies directed against VEGF ligand and VEGF receptors, and by truncated (lacking a transmembrane sequence and cytoplasmic kinase domain) soluble VEGFR-2 receptors. Dominant mutations introduced into either VEGFR-2 or FGFR-1 which result in a loss of enzymatic activity inhibits tumor growth in vivo. Antisense targeting of these receptors or their cognate ligands also inhibits angiogenesis and tumor growth. Recent evidence has elucidated, in part, the temporal requirements of these receptors in tumor growth. It appears that VEGF signaling is critical in early tumor growth and bFGF is more important at a later time associated with tumor expansion.

Other RTKs such as HER1 and HER2 are involved in cell proliferation and are associated with diseases such as psoriasis and cancer. Disruption of signal transduction by inhibition of these kinases would have an antiproliferative and therapeutic effect.

DESCRIPTION OF THE INVENTION

In accordance with the present invention, compounds of formula I

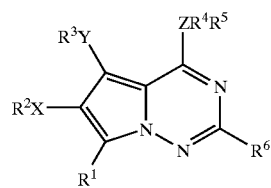

I their enantiomers, diastereomers, and pharmaceutically acceptable salts, prodrugs and solvates thereof inhibit the tyrosine kinase activity of growth factor receptors such as VEGFR-2. In formula I and throughout the specification, the above symbols are defined as follows:

X and Y are independently selected from O, OCO, S, SO, $SO_2$, CO, $CO_2$, $NR^{10}$, $NR^{11}CO$, $NR^{12}CONR^{13}$, $NR^{14}CO_2$, $NR^{15}SO_2$, $NR^{16}SO_2NR^{17}$, $SO_2NR^{18}$, $CONR^{19}$, halogen, nitro, cyano, or X or Y are absent;

Z is selected from O, S, N, or $CR^{20}$;

$R^1$ is hydrogen, $CH_3$, OH, $OCH_3$, SH, $SCH_3$, $OCOR^{21}$, $SOR^{22}$, $SO_2R^{23}$, $SO_2NR^{24}R^{25}$, $CO_2R^{26}$, $CONR^{27}R^{28}$, $NH_2$, $NR^{29}SO_2NR^{30}R^{31}$, $NR^{32}SO_2R^{33}$, $NR^{34}CR^{35}$, $NR^{36}CO_2R^{37}$, $NR^{38}CONR^{39}R^{40}$, halogen, nitro, or cyano;

$R^2$ and $R^3$ are independently hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heterocycloalkyl or substituted heterocycloalkyl, or when X is halo, nitro or cyano $R^2$ is absent or when Y is halo, nitro or cyano $R^3$ is absent;

$R^4$ and $R^5$ are independently hydrogen, alkyl, substituted alkyl, aryl, substituted aryl, heterocyclo, substituted heterocyclo, aralkyl, substituted aralkyl, or $R^4$ and $R^5$ may together form an optionally substituted monocyclic 5–7 membered saturated or unsaturated carbocyclic or heterocyclic ring, or an optionally substituted bicyclic 7–11 membered saturated or unsaturated carbocyclic or heterocyclic ring, except that when Z is O or S, $R^5$ is absent, or when Z is nitrogen, $R^4$ and $R^5$ are not both hydrogen;

$R^6$ is H, alkyl, substituted alkyl, aryl, substituted aryl, heterocyclo, substituted heterocyclo, $NR^7R^8$, $OR^9$ or halogen;

$R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{21}$, $R^{24}$, $R^{25}$, $R^{26}$, $R^{27}$, $R^{28}$, $R^{29}$, $R^{30}$, $R^{31}$, $R^{32}$, $R^{34}$, $R^{35}$, $R^{36}$, $R^{38}$, $R^{39}$ and $R^{40}$ are independently selected from the group consisting of hydrogen, alkyl, substituted alkyl, aryl, substituted aryl, heterocyclo, or substituted heterocyclo;

$R^{22}$, $R^{23}$, $R^{33}$ and $R^{37}$ are independently selected from the group consisting of alkyl, substituted alkyl, aryl, substituted aryl, heterocyclo, or substituted heterocyclo; and $R^{20}$ is selected from the group consisting of hydrogen, lower alkyl or substituted alkyl, or $R^{20}$ is absent if the carbon to which it is attached is part of an unsaturated aryl or heteroaryl ring;

with the provisos that:
a. $R^2$ may not be hydrogen if X is SO, $SO_2$, $NR^{13}CO_2$, or $NR^{14}SO_2$
b. $R^3$ may not be hydrogen if Y is SO, $SO_2$, $NR^{13}CO_2$, or $NR^{14}SO_2$.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring.

Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents. Also included are smaller heterocyclos, such as, epoxides and aziridines.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:
   a) *Design of Prodrugs*, edited by H. Bundgaard, (Elsevier, 1985) and *Methods in Enzymology*, Vol.42, p. 309–396, edited by K. Widder, et al. (Acamedic Press, 1985);
   b) *A Textbook of Drug Design and Development*, edited by Krosgaard-Larsen and H. Bundgaard, Chapter 5, "Design and Application of Prodrugs," by H. Bundgaard, p. 113–191 (1991);
   c) H. Bundgaard, *Advanced Drug Delivery Reviews*, 8, 1–38 (1992);

It should further be understood that solvates (e.g., hydrates) of the compounds of formula I are also with the scope of the present invention. Methods of solvation are generally known in the art.

Use and Utility

The present invention is based on the discovery that certain pyrrolotriazines are inhibitors of protein kinases. More specifically, they inhibit the effects of VEGF, a property of value in the treatment of disease states associated with angiogenesis and/or increased vascular permeability such as cancer. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with VEGF, especially those tumors which are significantly dependent on VEGF for their growth and spread, including for example, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung. In another embodiment, the compounds of the present invention are also useful in the treatment of noncancerous disorders such as diabetes, diabetic retinopathy, psoriasis, rheumatoid arthritis, obesity, Kaposi's sarcoma, haemangioma, acute and chronic nephropathies (including proliferative glomerulonephritis and diabetesinduced renal disease), atheroma, arterial restenosis, autoimmune diseases, acute inflammation and ocular diseases with retinal vessel proliferation, diabetic retinopathy, retinopathy of prematurity and macular degeneration. The invention also relates to prevention of blastocyte implantation in a mammal, treatment of atherosclerosis, excema, sclerodema, hemangioma. Compounds of the present invention posses good activity against VEGF receptor tyrosine kinase while possessing some activity against other tyrosine kinases.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined herein before.

The compounds described herein also inhibit other receptor tyrosine kinases including HER1 and HER2 and are therefore useful in the treatment of proliferative disorders such as psoriasis and cancer. The HER1 receptor kinase has been shown to be expressed and activated in many solid tumors including non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor effficacy in preclinical and clinical studies. It is therefore expected that inhibitors of the HER1 and HER2 kinases will have efficacy in the treatment of tumors that depend on signaling from either of the two receptors. The ability of these compounds to inhibit HER1 further adds to their use as antiangiogenic agents. See the following documents and references cited therein: Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R, Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000).

In addition, the formula I compounds of this invention may be used as contraceptives in mammals.

The antiproliferative, antiangiogenic and/or vascular permeability reducing treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anticancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin $\alpha_v\beta_3$ function, angiostatin, razoxin);

(ii) cytostatic agents such as antiestrogens (for example tamoxifen, toremifen, raloxifene, droloxifene, iodoxyfene), progestogens (for example megestrol acetate), aromatase inhibitors (for example anastrozole, letrazole, borazole, exemestane), antiharmones, antiprogestogens, antiandrogens (for example flutamide, nilutamide, bicalutamide, cyproterone acetate), LHRH agonists and antagonists (for example gosereline acetate, luprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotephan); antimitotic agents (for example vinca alkaloids like vincristine and taxoids like taxol, taxotere and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols); and biological response modifiers.

As stated above, the formula I compounds of the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as VEGFR-2.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may be administered in a dosage range of about 0.05 to 200 mg/kg/day, preferably less than 100 mg/kg/day, in a single dose or in 2 to 4 divided doses.

Biological Assays

| VEGFR-2 and FGFR-1 Kinase assays: | | |
|---|---|---|
| Reagents | Final Concentration | |
| Stock Solution | VEGFR-2 | FGFR-1 |
| Tris pH 7.0 | 20 mM | 20 mM |
| BSA 10 mg/ml | 25 µg/ml | 25 µg/ml |
| MnCl$_2$ (1 M) | 1.5 mM | 0.5 mM |
| MgCl$_2$ (1 M) | — | 0.5 mM |
| DTT (1 M) | 0.5 mM | 0.5 mM |
| Enzyme Stock in 10% glycerol (1 mg/ml) | 5 ng/rxn | 20 ng/rxn |
| Polyglu/tyr (10 mg/ml) | 80 µg/ml | 30 µg/ml |
| ATP (1 mM) | 2.5 µM | 1.0 uM |
| γ-ATP (10 µCi/µl) | 0.5 µCi/ml | 0.5 µCi |

Incubation mixtures employed for VEGFR-2 or FGFR-1 assay contain the synthetic substrate polyGlu:Tyr, (4:1), ATP, ATP-γ-$^{33}$P and buffer containing Mn$^{++}$ and/or Mg$^{++}$, DTT, BSA, and Tris buffer. The reaction is initiated by addition of enzyme and after 60 minutes is terminated by the addition of TCA to 30%. Inhibitors are brought to 10 mM in 100% DMSO. Assays are prepared in a 96 well format. Compounds are diluted 1:500 in 100% DMSO and then 1:10 in water for a final DMSO concentration of 10%. 10 µL are added to rows B–H in a 96 well format of 10% DMSO. 20 µl of compound is added to row A at a concentration 5 fold higher than running conditions. Ten µL are transferred to each row with 10 pippetting phases for mixing, and at row F 10 µL are discarded. Row G is a control with no compound and row H is no compound and no enzyme control. Enzyme and substrate are delivered using a Tomtec Quadra station.

Plates are covered with sticky plate tops, incubated at 27° C. for 60 minutes, and then acid precipitated with TCA for 20 minutes on ice. The precipitate is transferred to UniFilter-96, GF/C microplates using either a Tomtec or Packard FilterMate harvester. Activity is determined by quantitating the incorporated radioactivity using a Packard TopCount Microplate Scintillation Counter following the addition of Microscint-20 cocktail into each dried well of the UniFilter microplates.

The instant compounds inhibit VEGFR-2 and FGFR-1 kinases with IC$_{50}$ values between 0.003–25 µM.

HER1 or HER2 Kinase Assays

Compounds of interest were assayed in a kinase buffer that contained 20 mM Tris.HCl, pH 7.5, 10 mM MnCl$_2$, 0.5 mM dithiothreitol, bovine serum albumin at 0.1 mg/ml, poly(glu/tyr, 4:1) at 0.1 mg/ml, 1 µM ATP, and 4 µCi/ml

[γ-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1, the cytoplasmic sequence of the receptor were expressed in insect cells as a GST fusion protein, which was purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER-1 and HER-2 kinases with $IC_{50}$ values between 0.003–25 µM.

Methods of Preparation

Certain compounds of formula I may generally be prepared according to the following schemes and the knowledge of one skilled in the art.

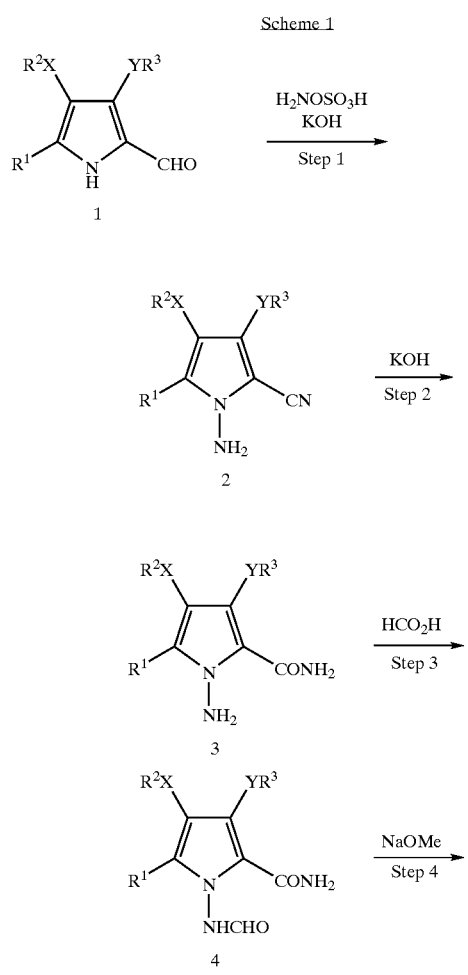

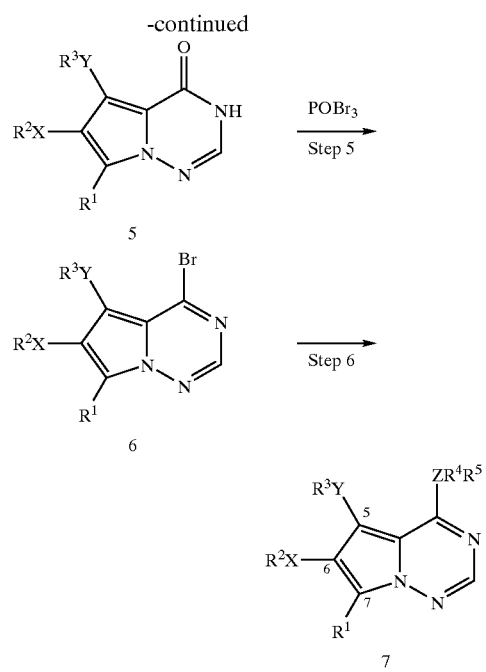

Step 1

The first step is accomplished by the reaction of an optionally substituted 2-formylpyrrole (product 1) with an aminating reagent, such as hydroxylamine-O-sulfonic acid, in an aqueous solvent at room temperature, followed by treatment under cooling with a base such as KOH. Compounds 1 may be obtained from substituted pyrroles by formylation, for example by reaction with phosphorus oxychloride and DMF. A methylpyrrole may be obtained by reduction of a formylpyrrole, for example by reaction with lithium aluminum hydride.

Step 2

The product 2 is reacted with an aqueous base such as KOH at room temperature to form the product 3 of Scheme 1.

Step 3

The compound 3 is reacted with an acylating agent, such as formic acid, in an aqueous solvent, to form the product 4 of Scheme 1.

Step 4

The compound 4 is cyclized with a base such as sodium methoxide in methanol with heating to form the product 5 of Scheme 1.

Step 5

The compound 5 is halogenated, for example with phosphorus oxybromide at elevated temperature, to form the product 6 of Scheme 1.

Step 6

The compound 6 is reacted with an amine such as an aniline in an organic solvent, such as acetonitrile, to form the product 7 of Scheme 1.

The compound 7 of Scheme 1 where $R_1$=7-halogen can be prepared from the compound 7 of Scheme 1 where $R_1$=hydrogen by reaction with a halogenating agent such as bromine in a suitable solvent such as acetic acid.

Scheme 2

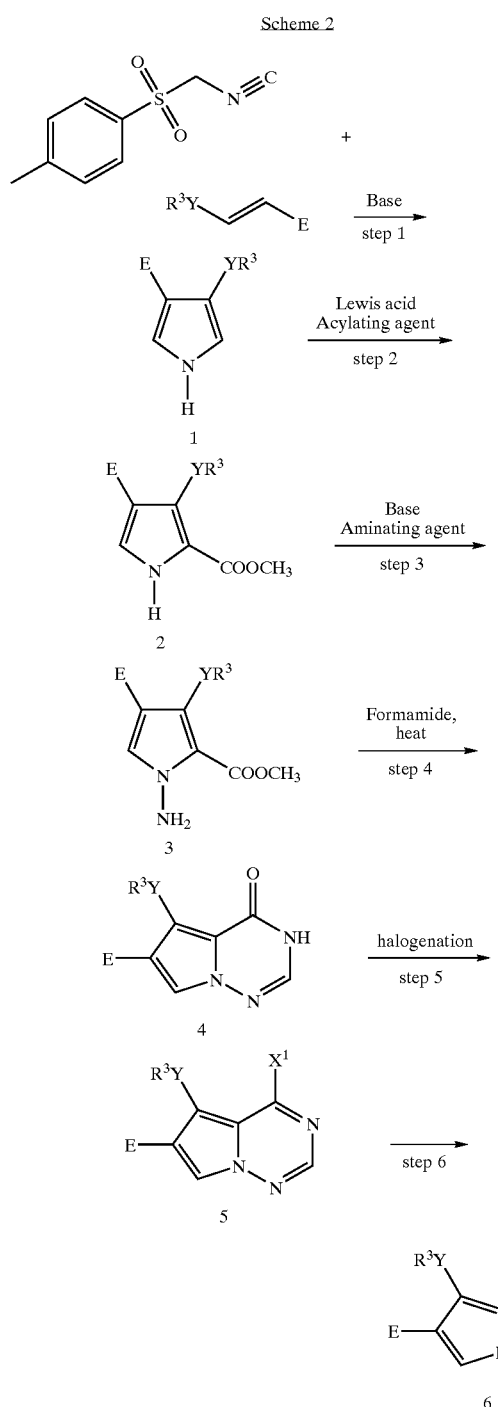

E = electron withdrawing group such as ester or nitro or ketone
X¹ = halogen

Step 1

An anion of tosylmethyl isocyanide (TosMIC) is reacted with a Michael acceptor such as ethyl crotonate to obtain disubstituted pyrrole 1. An anion of TosMIC could be made by treating a solution of it in dimethyl sulfoxide (DMSO) with a base such as sodium hydride (NaH) at rt or a solution of it in tetrahydrofuran (THF) with lithium hexamethyldisilazane at −78° C.

Step 2

Treatment of pyrrole 1 with an acylating agent such as trichloroacetyl chloride in the presence of a Lewis acid such as aluminum chloride at from rt to 50° C. followed by treatment with sodium methoxide could afford trisubstituted pyrrole 2. Alternatively, following the published procedure of (M. Suzuki, M. Miyoshi, K. Matsumoto J. Org. Chem. 1974, 39, 1980) Compound 2 could be obtained by warming an aldehyde, such as acetaldehyde, with 2 equivalents of ethyl isocyanoacetate in the presence of a base, such as DBU, in an organic solvent, such as THF.

Step 3

Pyrrole 2 could be aminated by an aminating reagent, such as diphenyl phosphoryl hydroxylamine, in the presence of a base, such as sodium hydride at rt in organic solvents, such as dimethyl formamide (DMF).

Step 4

N-Aminated pyrrole 3 upon heating at from 120 to 195° C. with formamide could undergo cyclization to afford 1,2,4-triazine 4.

Step 5

Compound 4 upon treatment with a halogenating agent, such as phosphorous oxybromide at from 60 to 115° C., in the presence or absence of a co-solvent such as 1,2-dichloroethane, compound 5 could be obtained.

Step 6

Compound 5 is reacted with amines, such as anilines in an organic solvent, such as DMF, to obtain compound 6. Alternatively, compound 5 is treated with an anion of a heterocyclic compound, such as oxindole, in an organic solvent such as THF.

Scheme 3

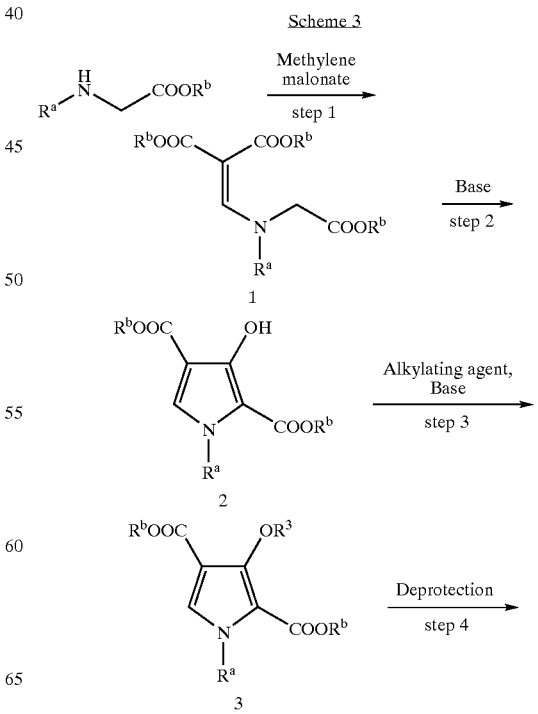

-continued

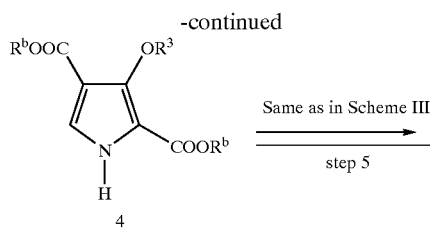

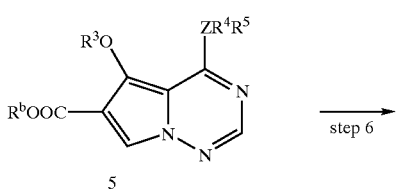

wherein $R^a = XR^2$, $R^b = R^6$ described hereinbefore

Step 1

A suitably N-protected ester of glycine, such as with benzyl group, could be added to dialkyl methylene malonate at from rt to 80° C. to obtain compound 1.

Step 2

Compound 1 could undergo cyclization to form pyrrole 2 upon treatment with a strong base, such as lithium hexamethyldisilazane at from −78° C. to rt in an organic solvent such as THF.

Step 3

Compound 2 could be alkylated by treatment with an alkylating agent, such as iodomethane or dimethyl sulfate, in the presence of a base, such as potassium carbonate, in an organic solvent, such as acetone or DMF.

Step 4

Deprotection of compound 3 could be achieved, when optionally protected by groups such as benzyl, by hydrogenation over a catalyst, such as palladium, in the presence of ammonium formate.

Step 5

Compound 4 could be converted to compound 5 in an analogous manner to that described in Scheme 2.

Step 6

Hydrolysis of the ester group in compound 5 could be achieved by treatment with a base such as aqueous potassium hydroxide. The resulting acid could be coupled with an amine in the presence of a coupling agent, such as DCC or PyBrop.

Scheme 4

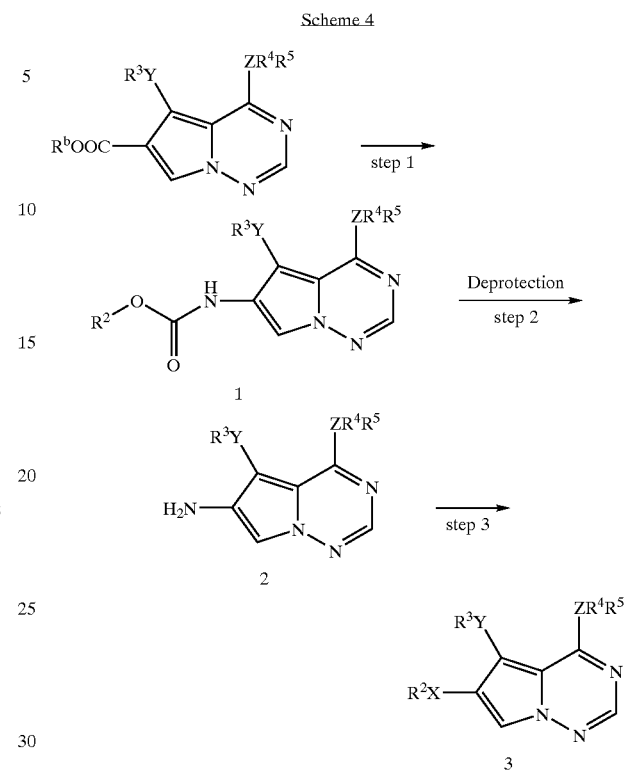

wherein $X = NR^{10}$, $NR^{11}CO$, $NR^{12}CONR^{13}$, $NR^{14}COO$, $NR^{15}SO_2$, $NR^{16}SO_2NR^{17}$, as described hereinbefore.

Step 1

Compound 5 of Scheme 3 could be converted to carboxylic acid by treatment with a base such as aqueous potassium hydroxide. This acid could undergo Curtius rearrangement by treatment with diphenyl phosphoryl azide in the presence of an alcohol, such as benzyl alcohol, in an organic solvent, such as 1,4-dioxane, to afford compound 1.

Step 2

Deprotection of the carbamate group could be achieved, when optionally protected by groups such as carbobenzyloxy, by hydrogenation over a catalyst, such as palladium.

Step 3

The amino group of compound 2 could be acylated, for example by treatment with a carboxylic acid in the presence of a coupling agent such as DCC, or could be sulfonylated, for example by treatment with a sulfonyl chloride. Alternatively, the amino group of compound 2 may be alkylated with alkyl halides or could undergo reductive amination with aldehydes in the presence of a reducing agent, such as sodium cyanoborohydride.

Scheme 5

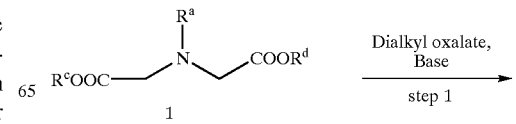

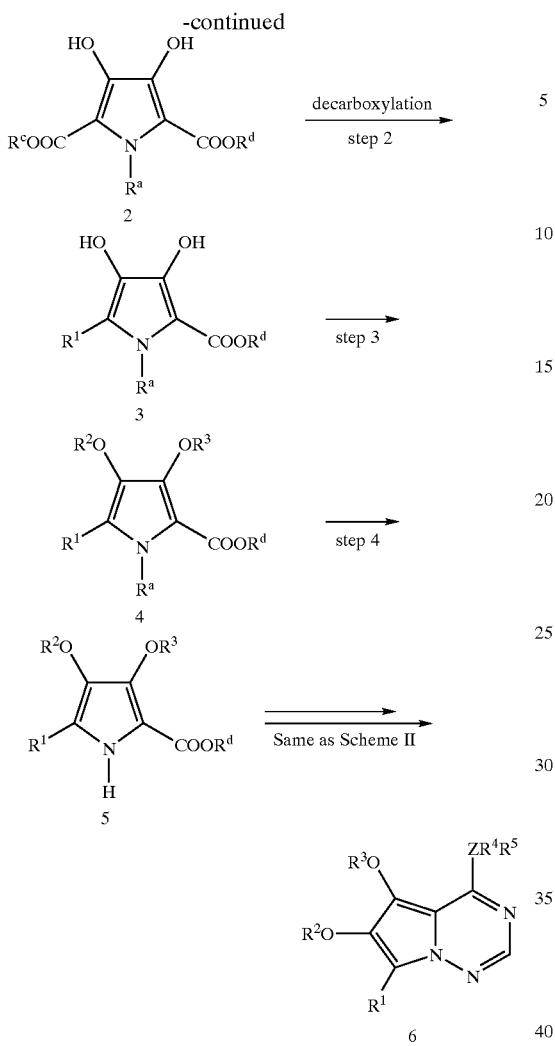

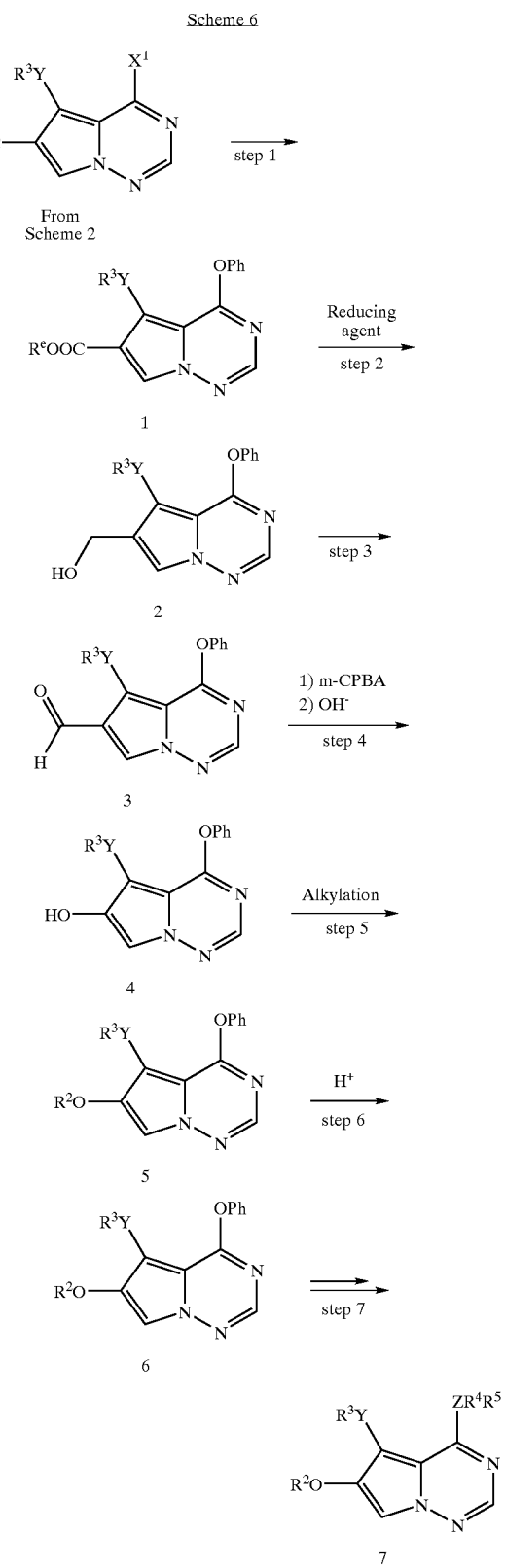

wherein $R^a = XR^2$; $R^c$, $R^d = R^6$; and $R^1$ = H or $COOR^{26}$ as described hereinbefore.

Step 1
Suitably protected compound 1 (imino dicarboxylate) could be cyclized by treatment with dialkyl oxalate in the presence of a base, such as sodium methoxide, in an organic solvent, such as methanol.

Step 2
Compound 2 upon selective deprotection, such as with trifluoro acetic acid (TFA) when optionally protected by tert-butyl ester, undergoes decarboxylation to afford Compound 3 where $R^1$=H. Step 2 is omitted to form compound 3 where $R^1$ = $COOR^{26}$.

Step 3
The hydroxy group of compound 3 could be etherified by reaction with an alkylating agent, such as dimethyl sulfate.

Step 4
Compound 4 could be deprotected by hydrogenation, when optionally protected as benzyl group, to obtain compound 5.

Step 5
Compound 5 could then be converted to compound 6 in an analogous manner to that described in step 4 of scheme 3 followed by steps 3 to 6 of Scheme 2.

$X^1$ = halogen
$R^e$ = $R^6$ described hereinbefore

19

Step 1

Compound 5 of Scheme 2 could be etherified at the 4-position, for example by treatment with phenoxide anion.

Step 2

Reduction with a reducing agent, such as DIBAL, in an organic solvent, such as toluene, could afford the alcohol 2.

Step 3

Oxidation of the alcohol could be achieved by treatment of compound 2, for example with MnO$_2$ at an elevated temperature in an organic solvent, such as toluene.

Step 4

Treatment of compound 3 with an oxidant, such as m-chloroperbenzoic acid (m-CPBA) in an organic solvent, such as dichloromethane, followed by aqueous hydrolysis with a base, such as potassium bicarbonate, could afford the hydroxy compound 4.

Step 5

Alkylation of the phenolic group in compound 4 with an agent, such as iodomethane, in the presence of a base, such as NaH, at from rt to 100° C., could afford compound 5.

Step 6

Hydrolysis of Compound 5 could be achieved by treatment with an acid, such as aqueous HCl, at an elevated temperature to afford compound 6.

Step 7

Compound 6 could be converted to compound 7 using procedures analogous to those described in Scheme 2.

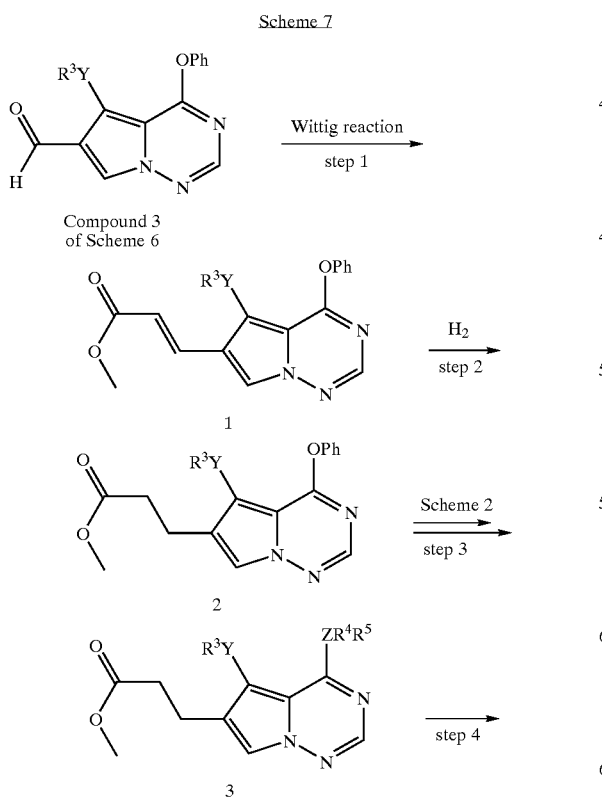

Scheme 7

20

-continued

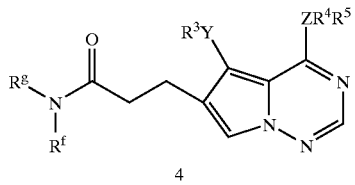

4 wherein $R^f$, $R^g$ = $R^2$ as described hereinbefore

Step 1

A compound 3 of Scheme 6 could undergo Wittig reaction, for example with phosphonates such as methyl diethylphosphonoacetate, in an organic solvent, such as dichlorethane, in the presence of a base, such as NaH to afford Compound 1.

Step 2

The double bond could be hydrogenated by treatment with hydrogen in the presence of a catalyst, such as palladium.

Step 3

Compound 2 could be converted to compound 3 by procedures described in Scheme 2.

Step 4

Hydrolysis of the ester, as described hereinbefore, followed by coupling of the resulting acid with an amine in the presence of a coupling agent, such as DCC, could afford Compound 4.

In addition, other compounds of formula I may be prepared using procedures generally known to those skilled in the art. In particular, the following examples provide additional methods for the preparation of the compounds of this invention.

The invention will now be further described by the following working examples(s), which are preferred embodiments of the invention. All temperatures are in degrees Celsius (° C.) unless otherwise indicated. HPLC purifications were done on C18 reverse phase (RP) columns using water methanol mixtures and trifluoroacetic acid as buffer solution. These examples are illustrative rather than limiting and it is to be understood that there may be other embodiments that fall within the spirit and scope of the invention as defined by the claims appended hereto.

Example 1

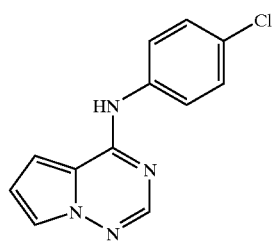

N-(4-Chlorophenyl)pyrrolo[2,1-f][1,2,4]triazin-4-amine

A. 4-Bromo-pyrrolo[2,1-f][1,2,4]triazine

A mixture of 50 mg (0.37 mmol) of pyrrolo[2,1-f][1,2,4]triazin-4(3H)-one [prepared as described in S. A. Patil, B. A. Otter and R. S. Klein, *J. Het. Chem.*, 31, 781–786 (1994)] and 0.5 g of phosphorus oxybromide was heated at 60° C. for 20 min., under argon. A clear orange melt was initially obtained which solidified to a yellow solid on continued heating. Ice was added with vigorous stirring to the solid. The mixture was extracted twice with ethyl acetate. The combined extracts were washed with sat. NaHCO$_3$ and brine, dried (MgSO$_4$), and the solvent removed to afford 63 mg of crude Compound A as an orange oil which crystallized on standing. (M+H)$^+$=198$^+$, 200$^+$ B.
4-(4-Chlorophenylamino)-pyrrolo[2,1-f][1,2,4]triazine A solution of 60 mg (0.3 mmol) of Compound A and 38 mg (0.3 mmol) of p-chloroaniline in 1.5 ml of acetonitrile was stirred overnight at rt and under argon. A white precipitate was obtained which was removed by filtration. The filter cake was suspended in ethyl acetate and sat. NaHCO$_3$ added and the mixture stirred until a solution was obtained. The organic layer was separated and washed with brine, dried (MgSO$_4$) and the solvent removed to yield 23 mg (0.094 mmol, 31%) of Example 1 as a white solid. (M+H)$^+$=245$^+$ Example 2

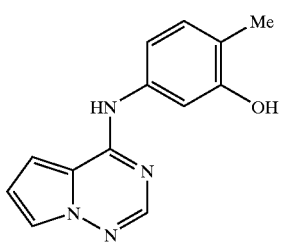

2-Methyl-5-(pyrrolo[2,1-f][1,2,4]triazin-4-ylamino)phenol

The compound of Example 2 was prepared as a white solid in 49% yield from Compound A of Example 1 and 3-hydroxy-4-methylaniline as described for Compound B of Example 1. (M+H)$^+$=241$^+$ Example 3

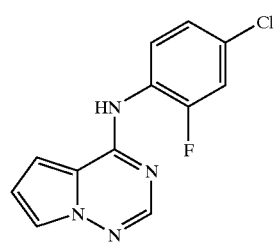

N-(4-Chloro-2-fluorophenyl)pyrrolo[2,1-f][1,2,4]triazin-4-amine

The compound of Example 3 was prepared as a white solid in 40% yield from Compound A of Example 1 and 2-fluoro-4-chloroaniline as described for Compound B of Example 1. (M+H)$^+$=263$^+$ Example 4

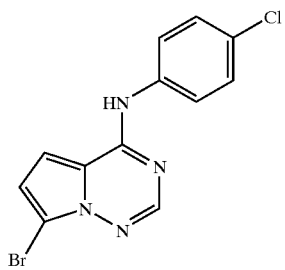

7-Bromo-N-(4-chlorophenyl)pyrrolo[2,1-f][1,2,4]triazin-4-amine

To a solution of 26 mg (0.11 mmol) of Example 1 in 1 ml of acetic acid was added dropwise a solution of 19 mg of bromine in 100 ml of acetic acid. A white precipitate was obtained during the addition. Stirring was continued for 1 hr, under argon. The mixture was evaporated to dryness and the residue diluted with ethyl acetate and treated with sat NaHCO$_3$. The clear colorless organic layer was washed with brine, dried (MgSO$_4$) and the solvent removed to give a white solid residue. This material was subjected to flash chromatography on a 15 cc column of silica gel. Elution with chloroform (100%) afforded 18 mg (0.06 mmol, 50%) of Example 4 as a white solid. (M+H)$^+$=323, 325$^+$ Example 5

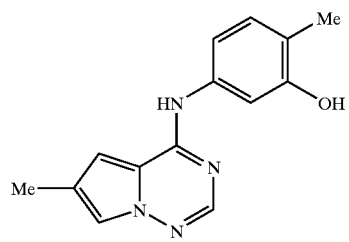

2-Methyl-5-[(6-methylpyrrolo[2,1-f][1,2,4]triazin-4-yl)amino]phenol

A.
2-Formyl-3-methylpyrrole/2-formyl-4-methylpyrrole

To 3.15 ml (41 mmol) of DMF at 0° C. under argon was added dropwise 3.81 ml (41 mmol) of phosphorus oxychloride. The cooling bath was removed and stirring was continued for 15 min. The solution was diluted with 9 ml of 1,2-dichloroethane and again cooled to 0° C. A solution of 3.0 g (37 mmol) of 3-methylpyrrole in 9 ml of 1,2-dichloroethane was added dropwise. The mixture was heated to reflux for 15 min, cooled to 0° C. and a solution of 16.2 g (203 mmol) of sodium acetate in 45 ml of water was added with vigorous stirring. The mixture was heated at reflux for 20 min and allowed to cool to room temperature. The aqueous layer was separated and extracted twice with methylene chloride. The combined organic layers were washed with sat NaHCO$_3$ until pH 7, dried (MgSO$_4$), and the solvent removed to yield a dark oily solid which was purified by flash chromatography (10% EtOAc:hexane) to afford 3.6 g (89%) of a 4:1 mixture of 2-formyl-3-methylpyrrole and 2-formyl-4-methylpyrrole as a pale yellow solid.

B. 1-Amino-2-aminocarbonyl-4-methyl-pyrrole

Compound A as an isomeric mixture was aminated as described in S. A. Patil, B. A. Otter and R. S. Klein, *J. Het. Chem.*, 31, 781–786 (1994) to form a 2:1 mixture of 1-amino-2-cyano-3-methylpyrrole and 1-amino-2-cyano-4-methylpyrrole in combined 20% yield. The mixture of nitrites was hydrolyzed as described in the reference to form Compound B as well as unreacted 1-amino-2-cyano-3-methylpyrrole, which were separated by flash chromatography (10% EtOAc:hexane).

C. 6-Methyl-pyrrolo[2,1-f][1,2,4]triazin-4(3H)-one

Compound C was prepared from Compound B as described in S. A. Patil, B. A. Otter and R. S. Klein, *J. Het. Chem.*, 31, 781–786 (1994).

D. 4-(3-Hydroxy-4-methyl-phenylamino)-6-methyl-pyrrolo[2,1-f] [1,2,4]triazine

Example 5 was prepared from Compound C using the 2 step sequence of Compound A of Example 1 and Compound B of Example 1, using 3-hydroxy-4-methylaniline. (M+H)$^+$=255.

Example 6

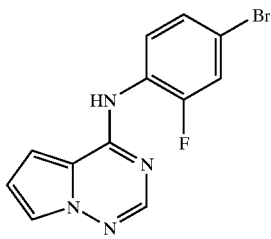

N-(4-Bromo-2-fluorophenyl)pyrrolo[2,1-f][1,2,4]triazin-4-amine

The title compound was prepared as a white solid in 57% yield from Compound A of Example 1 and 2-fluoro-4-bromoaniline as described for Compound B of Example 1. (M+H)$^+$=307, 309.

Example 7

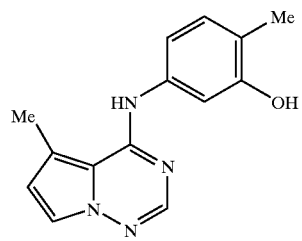

2-Methyl-5-[(5-methylpyrrolo[2,1-f][1,2,4]triazin-4-yl)amino]phenol

A. 1-Amino-2-aminocarbonyl-3-methyl-pyrrole

A solution of 290 mg (2.4 mmol) of 1-amino-2-cyano-3-methylpyrrole (prepared as described in Compound B of Example 5) and 3.5 g (62 mmol) of potassium hydroxide in 2 ml of water and 28 ml of ethanol was heated at reflux for 3 hr. The mixture was evaporated to near dryness, the residue diluted with additional water, and the mixture extracted with ethyl acetate (3×). The combined extracts were washed with brine, dried (MgSO$_4$) and the solvent removed to yield 274 mg (82%) of Compound A as a white solid.

B. 4-(3-Hydroxy-4-methyl-phenylamino)-5-methyl-pyrrolo[2,1-f] [1,2,4]triazine

Example 7 was prepared from Compound A as described for Compounds C and D of Example 5. (M+H)$^+$=255.

Example 8

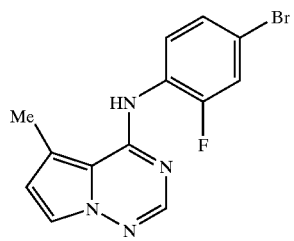

N-(4-Bromo-2-fluorophenyl)-5-methylpyrrolo[2,1-f] [1,2,4] triazin-4-amine

Example 8 was prepared as a white solid in 29% overall yield from 5-methylpyrrolo[2,1-f][1,2,4]triazin-4(3H)-one using the 2 step sequence of Compounds A and B of Example 1, using 2-fluoro-4-bromo-aniline. (M+H)$^+$=321, 323.

Example 9

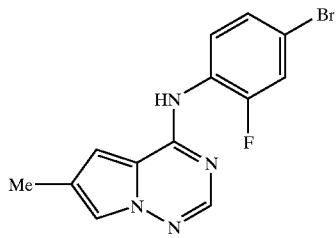

N-(4-Bromo-2-fluorophenyl)-6-methylpyrrolo[2,1-f]
[1,2,4]triazin-4-amine

Example 9 was prepared as a white solid in 20% overall yield from Compound C of Example 5 using the 2 step sequence of Compound A and Compound B of Example 1, using 2-fluoro-4-bromo-aniline. The product was purified by flash chromatography on silica gel with 10% ethyl acetate/hexanes. (M+H)$^+$=321, 323.

Example 10

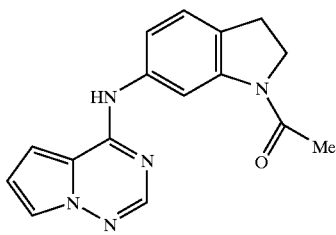

1-[2,3-Dihydro-6-(pyrrolo[2,1-f][1,2,4]triazin-4-ylamino)-1H-indol-1-yl]ethanone Example 10 was prepared as a white solid in 4% yield from Compound A of Example 1 and 1-acetyl-6-aminoindoline as described for Compound B of Example 1, using 10% isopropanol/methylene chloride for extraction, and with purification by chromatography on silica gel with ethyl acetate. (M+H)$^+$=294.

Example 11

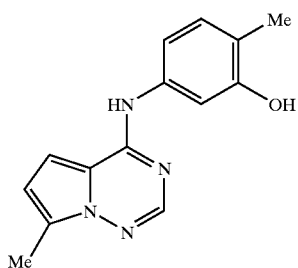

2-Methyl-5-[(7-methylpyrrolo[2,1-f][1,2,4]triazin-4-yl)amino]phenol

A. 2-Methylpyrrole

To 80 ml of a 1 M solution of lithium aluminum hydride in ether (80 mmol), at rt and under argon, was added dropwise a solution of 4.0 g (40 mmol) of 2-formylpyrrole at such a rate as to maintain gentle reflux. Reflux was continued for 6 hr. The excess hydride was hydrolyzed by the dropwise sequential addition of 3 ml of water (with cooling), 3 ml of 15% sodium hydroxide, and 9 ml of water. The resulting solids were removed by filtration and the filter cake washed well with additional ether. The filtrate was evaporated to dryness and the dark oil residue diluted with methylene chloride, dried (MgSO$_4$) and the solvent removed. The resulting dark oil was distilled (kugelrohr, 700 mm, 100° C.) to afford 1.13 g (35%) of Compound A as a clear colorless oil.

B. 2-Formyl-5-methyl-pyrrole

To 0.54 ml of DMF, with ice cooling and under argon, was added dropwise 0.64 ml of POCl$_3$. The reaction, which solidified during the addition, was warmed lightly with a warm water bath and the clear colorless solution stirred an additional 20 min after addition was completed. The mixture was diluted with 3 ml of 1,2-dichloroethane and, with cooling, a solution of 510 mg (6.3 mmol) of Compound A was added dropwise. The solution was heated at reflux for 15 min, ice cooled and a solution of 2.6 g (31.5 mmol) of sodium acetate was added with vigorous stirring. The mixture was heated at 80° C. for 20 min, cooled to rt and extracted with methylene chloride. The extracts were washed with brine, dried (MgSO$_4$) and the solvent removed to give a dark oil residue. This material was subjected to flash chromatography on silica with 10% EtOAc:hexane to afford 126 mg (18%) of Compound B as a light tan solid.

C. 1-Amino-2-cyano-5-methyl-pyrrole

A solution of 140 mg (1.28 mmol) of Compound B in 2 ml of methylene chloride, at rt and under argon, was added rapidly dropwise to a solution of 290 mg (1.35 mmol) of MSH(O-mesitylenesulfonyl-hydroxylamine) in 2 ml of methylene chloride. A deep red solution was obtained which was stirred for an additional 0.5 hr. The mixture was washed twice with sat NaHCO$_3$, dried (MgSO$_4$) and the solvent removed to give a deep red oil. A solution of this material in 5 ml of DMF was added a dropwise to a suspension of 102 mg (2.56 mmol) of sodium hydride in 5 ml of DMF, at rt and under argon. The red color was consumed and the reaction became dark yellow. Stirring was continued for an additional 0.5 hr. The mixture was ice cooled and a solution of 385 mg (1.8 mmol) of MSH in 5 ml of DMF was added. Stirring was continued for 1 hr with cooling. The dark solution was diluted with ethyl acetate and washed once with water. The aqueous layer was rextracted once with ethyl acetate. The combined organic layers were dried (MgSO$_4$) and the solvents removed. The resulting dark red oil was subjected to flash chromatography on silica with 20% EtOAc:hexane to afford 100 mg (65%) of Compound C as a yellow solid.

D. 1-Amino-2-aminocarbonyl-5-methyl-pyrrole

To a solution of 1.1 g (20 mmol) of KOH in 2.5 ml of water was added 100 mg (0.82 mmol) of Compound C. The suspension was stirred overnight at rt and heated at 50° C. for 4 hrs. The resulting precipitate was removed by filtration. The filter cake was dissolved in ethyl acetate, the solution was dried (MgSO$_4$) and the solvent removed to give 58 mg of Compound D as a yellow solid. The aqueous filtrate was extracted 3× with ethyl acetate. The combined extracts were dried (MgSO$_4$) and the solvent removed to give an additional 11 mg of Compound D as a yellow solid (total 69 mg, 60%).

E. 7-methyl-pyrrolo[2,1-f][1,2,4]triazin-4(3H)-one

A solution of 65 mg (0.47 mmol) of Compound D in 0.5 ml of formic acid was heated at 100° C. for 4 hrs. After removal of the solvent, the residue was subjected to flash chromatography on silica with 50% EtOAc:hexane to afford 53 mg (76%) of Compound E as a white solid.

F. 4-(3-Hydroxy-4-methyl-phenylamino)-7-methyl-pyrrolo[2,1-f][1,2,4]triazine Example 11 was prepared as a white solid in 30% overall yield from Compound E using the 2 step sequence of Compound A of Example 1 and Compound B of Example 1, using 3-hydroxy-4-methylaniline. The product was purified by flash chromatography on silica with 25% ethyl acetate/hexanes. (M+H)$^+$255.

Example 12

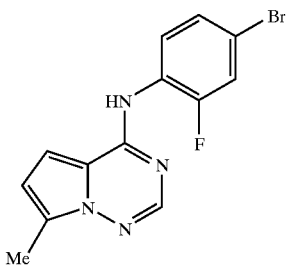

N-(4-Bromo-2-fluorophenyl)-7-methylpyrrolo[2,1-f][1,2,4]triazin-4-amine

Example 12 was prepared as a white solid in 33% overall yield from Compound E of Example 11 using the 2 step sequence of Compound A of Example 1 and Compound B of Example 1, using 2-fluoro-4-bromoaniline. The product was purified by flash chromatography on silica with 10% ethyl acetate/hexanes. (M+H)$^+$=321, 323.

Example 13

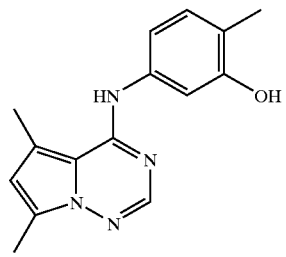

5-[(5,7-Dimethylpyrrolo[2,1-f][1,2,4]triazin-4-yl)amino]-2-methylphenol

A. 2-formyl-3,5-dimethylpyrrole

To dimethylformamide (4.5 mL, 57.8 mmol) under argon at 0° C. was added phosphorus oxychloride (57.8 mmol) dropwise over 5 min. The cooling bath was removed and after 15 min. 1,2-dichloroethane (15 mL) was added. The reaction mixture was again cooled to 0° C. and a solution of 2,4-dimethylpyrrole (52.6 mmol) in 1,2-dichloroethane (15 mL) was added dropwise over 15 min. The reaction was heated to reflux for 15 min, and then cooled to rt. A solution of sodium acetate (24 g) in water (75 mL) was added slowly to the reaction mixture and the resulting mixture was again heated to reflux for 20 min. After the reaction mixture was cooled to rt it was diluted with CH$_2$Cl$_2$, and the aqueous phase was washed with CH$_2$Cl$_2$ (2×50 mL). The combined organic fractions were washed with saturated NaHCO$_3$, dried (Na$_2$SO$_4$), and concentrated in vacuo. The crude material was purified by chromatography on silica gel eluting with 10% ethyl acetate in hexane to provide 5.2 g (80%) of the desired compound 2-formyl-3,5-dimethylpyrrole. [M+H]+=124.1, [M−H]$^-$=122.0

B. 5,7-dimethylpyrrolo[2,1-f][1,2,4]triazine-4(3H)-one

Compound B was prepared from A as described in [S. A. Patil, B. A. Otter and R. S. Klein, *J. Het. Chem.*, 31, 781–786 (1994)]. Thus, removal of formic acid after the reaction gave 5 mg (95%) of compound B. $^1$H NMR (CD$_3$OD): δ 7.40 (s, 1H), 2.15 (s, 1H), 2.28 (s, 3H), 2.19 (s, 3H)

C. 5,7-Dimethyl-4-(3-hydroxy-4-methylphenylamino)-pyrrolo[2,1-f] [1,2,4]triazine The title compound was prepared by treating compound B with 3-hydroxy-4-methylaniline as described for compound B of Example 1. Thus, after purification by preparative HPLC, 14 mg (25%) of 5,7-Dimethyl-4-(3-hydroxy-4-methylphenylamino)-pyrrolo[2,1-f][1,2,4]triazine was obtained as white solid. MS: [M+H]+=269.2, ESI [M−H]$^-$=267.0; $^1$H NMR (CDCl$_3$): δ 8.20 (br s, 1H), 7.81 (s, 1H), 7.06 (d, J=8.0 Hz, 1H), 6.99 (s, 2H), 6.69 (dd, J=8.0, 5.7 Hz, 1H), 6.25 (s, 1H), 2.58 (s, 3H), 2.43 (s, 3H), 2.07 (s, 3H)

Example 14

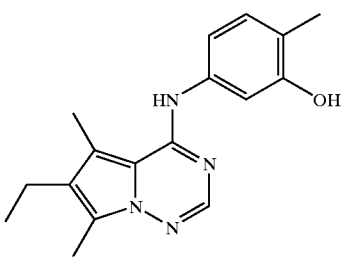

5-[(6-Ethyl-5,7-dimethylpyrrolo[2,1-f][1,2,4]triazin-4-yl)amino]-2-methylphenol

The title compound was prepared from 2,4-dimethyl-3-ethylpyrrole in a manner similar to the preparation of Example 13 from 3,5-dimethylpyrrole. Thus, after purification by preparative HPLC, 19 mg (21%) of 5,7-dimethyl-6-ethyl-4-(3-hydroxy-4-methylphenylamino)-pyrrolo[2,1-f][1,2,4]triazine was obtained as white solid. MS: [M+H]$^+$=297.3, [M−H]$^-$=295.1; $^1$H NMR (CDCl$_3$): δ 9.67 (br s, 1H), 7.81 (s, 1H), 7.10 (d, J=8.4 Hz, 1H), 6.90 (br s, 1H), 6.70 (s, 1H), 6.64 (dd, J=8.3, 5.8 Hz, H), 2.64 (q, J=7.5, 1H), 2.55 (s, 3H), 2.44 (s, 3H), 2.08 (s, 3H), 1.13 (t, J=7.5, 3H)

Example 15

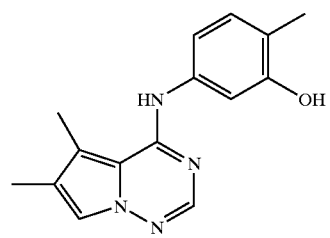

5-[(5,6-Dimethylpyrrolo[2,1-f][1,2,4]triazin-4-yl)amino]-2-methylphenol

A. Preparation of 3,4-dimethylpyrrole

To a flask containing anhydrous diethyl ether (160 mL) was added slowly a solution of LiAlH$_4$ in THF (1 M, 71.01 mmol). This mixture was stirred for 15 min. at rt. diethyl 3,4-pyrroledicarboxylate (5.0 g, 23.67 mmol) was added portion-wise as a solid to the solution over 15 min. The reaction mixture was then heated at 45° C. (reflux) overnight. The reaction mixture was cooled to 0° C. and Na$_2$SO$_4$10 H$_2$O (15 g) was slowly added. The mixture was stirred for 30 min. and 15 mL of 10% aqueous NH$_4$Cl was added slowly and the mixture stirred for an additional 15 min. The mixture was filtered and the residue was rinsed with ethyl acetate (3×20 mL). The filtrate was dried over Na$_2$SO$_4$ and purified by chromatography on silica gel eluting with a gradient of 10–20% ethyl acetate in hexanes to provide 540 mg (24%) of 3,4-dimethylpyrrole. MS: [M−H]$^-$=94.0

B. 5,6-Dimethyl-4-(3-hydroxy-4-methylphenylamino)-pyrrolo[2,1-f] [1,2,4]triazine The compound A was converted to the title compound in a manner similar to the preparation of Example 13 from 3,5-dimethylpyrrole. Thus, after purification by preparative HPLC, 19 mg (21%) of 5,6-dimethyl-4-(3-hydroxy-4-methylphenylamino)-pyrrolo[2,1-f][1,2,4]triazine was obtained as white solid. [M+H]$^+$=269.2, [M−H]$^-$=267.0; $^1$H NMR (CDCl$_3$): δ 8.30 (br s, 1H), 7.54 (s, 1H), 7.14 (s, 1H), 6.87 (d, J=7.9 Hz, 1H), 6.85 (s, 1H), 6.45 (dd, J=7.8, 1.9 Hz, 1H), 2.28 (s, 3H), 1.97 (s, 3H), 1.85 (s, 3H)

Example 16

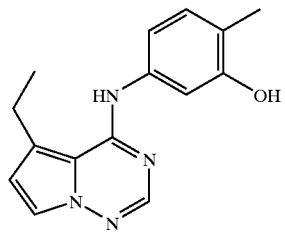

5-[(5-Ethylpyrrolo[2,1-f][1,2,4]triazin-4-yl)amino]-2-methylphenol

A. Preparation of 2-formyl-3-ethylpyrrole

3-Ethylpyrrole was converted to a mixture of Compound A and 2-formyl-41 ethylpyrrole as described in the preparation of Compound A of Example 5. [M+H]$^+$= 124.1

B. Preparation of 5-ethyl-4-(3-hydroxy-4-methylphenylamino)-pyrrolo[2,1-f][1,2,4]triazine The mixture obtained above was converted to the title compound in a manner similar to the preparation of Example 5 from compound B of Example 5. Thus, after purification by preparative HPLC, 22 mg (26%) of 5-ethyl-4-(3-hydroxy-4-methylphenylamino)-pyrrolo[2,1-f][1,2,4]triazine was obtained as white solid. MS: [M+H]$^+$=269.2, [M−H]$^-$=267.1; $^1$H NMR (CDCl$_3$):δ 8.80 (br s, 1H), 7.73 (s, 1H), 7.43 (s, 1H), 6.99–6.89 (m, 2H), 6.60 (s, 1H), 6.55 (d, J=2.7 Hz, 1H), 2.45 (s, 1H), 2.87 (q, J=7.5 Hz, 2H), 2.00 (s, 3H), 1.31 (t, J=7.5 Hz, 3H)

Example 17

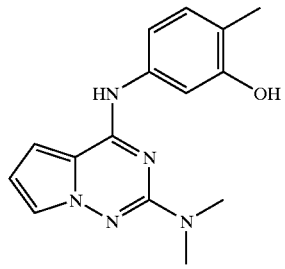

5-[[2-(Dimethylamino)pyrrolo[2,1-f][1,2,4]triazin-4-yl]amino]-2-methylphenol

To a solution of 4-chloro-2-dimethylaminopyrrolo[2,1-f][1,2,4]triazine-2-amine (50 mg, 0.26 mmol) (Tetrahedron, 3037, 52, 1996, José Ma. Quintela, María J. Moreira and Carlos Peinador) in ethanol (2.5 mL) under argon was added 5-amino-o-cresol (35 mg, 0.28 mmol). The reaction mixture was stirred overnight at 75° C. Upon cooling, a solid precipitated which was recrystallized from warm ethanol to provide 52 mg (72%) of the title compound as white solid.

MS: [M+H]⁺=284.2, ESI [M–H]⁻=282.1; ¹H NMR (CDCl₃): δ 7.52 (s, 1H), 7.13–6.98 (m, 4H), 6.58 (s, 1H), 3.15 (s, 6H), 2.19 (s, 3H).

Example 18

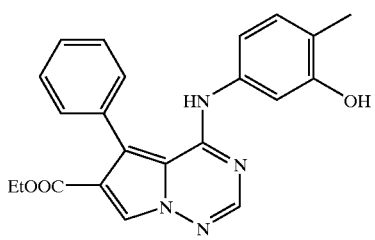

4-[(3-Hydroxy-4-methylphenyl)amino]-5-phenylpyrrolo[2,1-f][1,2,4]triazine-6-carboxylic acid ethyl ester A. 3-carboethoxy-4-phenylpyrrole To a 1.0 M solution of lithium hexamethyldisilazide in THF (41 mL, 41 mmol) at 78° C. was added dropwise over 45 min. a solution of tosylmethyl isocyanide (8.1 g, 41 mmol) in THF. After the reaction was stirred for an additional 45 min. a solution of trans-ethyl cinnamate (7.3 g, 41 mmol) in THF (40 mL) was added over 40 min. The reaction was warmed to 25° C. and stirred for 5 h. The reaction was diluted with ethyl acetate and washed with sat. aqueous NaHCO₃. The aqueous layer was extracted three times with ethyl acetate, dried (Na₂SO₄), concentrated and purified by chromatography on silica gel eluting with a gradient of 20–30% ethyl acetate in hexanes to provide 3.4 g (41%) of 3-carboethoxy-4-phenylpyrrole as an off-white solid. ¹HNMR (CDCl₃): δ 8.62 (br s, 1H), 7.5 7–7.12 (m, 6H), 6.73 (s, 1H), 4.19 (q, J=7.1 Hz, 2H), 1.23 (t, J=7.1 Hz, 3H)

B. 3-carboethoxy-4-phenyl-5-formylpyrrole

Compound A was converted to the title compound (74% yield) in a manner similar to the preparation of Compound A of Example 5 from 3-methylpyrrole. [M–H]⁻=242

C. 3-carboethoxy-4-phenyl-5-cyanopyrrole

To a solution of Compound B (0.55 g, 2.4 mmol) in pyridine (10 mL) under argon at rt was added hydroxylamine hydrochloride (0.18 g, 2.6 mmol). The reaction mixture was stirred for 2 hrs. Acetic anhydride (0.25 mL, 2.6 mmol) was added and the mixture was heated at 95° C. for 6 h. Water and ethyl acetate were added to quench the reaction and the mixture was extracted (3×) with ethyl acetate. The combined extracts were washed with brine, dried (Na₂SO₄) and purified by chromatography on silica gel eluting with a gradient of 25–50% ethyl acetate in hexanes to provide 0.1 g ((17%) of Compound C as a solid. ¹H NMR (CDCl₃): δ 9.92 (br s, 1H), 7.52-7.30 (m, 16H), 4.24 (q, J=7.1 Hz, 2H), 1.23 (t, J=7.1 Hz, 3H)

D. 1-amino-3-carboethoxy-4-phenyl-5-cyanopyrrole

To a suspension of NaH (60% in oil, 33 mg, 0.83 mmol) in DMF (5 mL) at 0° C. was added Compound C (0.1 g, 0.42 mmol) in DMF (3 mL). After 10 min. at 0° C., diphenyl phosphoryl hydroxylamine (0.19 g, 0.83 mmol) was added neat followed by DMF (3 mL). The reaction mixture was stirred for 2 hrs at 25° C. and then quenched with pH 7 phosphate buffer (15 mL). The mixture was extracted with ethyl acetate (4×20 mL). The combined extracts were dried (Na₂SO₄) and purified by chromatography on silica gel eluting with 25–50% ethyl acetate in hexanes to provide 94 mg (85%) of Compound D. ¹H NMR (CDCl₃): δ 10.2 (br s, 1H), 7.55 (s, 1H), 7.47-7.35 (m, 5H), 5.12 (s, 2H), 4.27 (q, J=7.1 Hz, 2H), 1.22 (t, J=7.1 Hz, 3H)

E. 5-Phenyl-6-carboethoxy-pyrrolo[2,1-f][1,2,4]triazin-4(3H)-one

To a solution of Compound D (94 mg, 0.4 mmol) in methanol (2 mL) and water (2 mL) was added sodium perborate tetrahydrate (0.28 g, 2 mmol). The reaction mixture was heated to 50° C. for 15 hrs and then quenched with water (5 mL). The mixture was extracted with ethyl acetate (3×10 mL). The combined organic extracts were washed with brine (10 mL), dried (Na₂SO₄), and concentrated in vacuo. The residue was heated with formic acid at 60° C. for 5 hrs. The formic acid was removed and the crude material was purified by chromatography silica gel eluting with a gradient of 25% methanol in chloroform to provide 26 mg (26%) of Compound E. [M–H]⁻=282

F. 5-phenyl-6-carboethoxy-4-(3-hydroxy-4-methylphenylamino)pyrrolo [2,1-f][1,2,4]triazine Phosphorus oxybromide (130 mg, 5 eq) was combined with Compound E (26 mg, 0.092 mmol) and heated to 60° C. for 45 min. The melt was poured into ice water and extracted with ethyl acetate (4×5 mL). The extracts were washed with sat. NaHCO₃, dried (Na₂SO₄) and concentrated in vacuo. The residue was dissolved in CH₃CN (1.0 mL) and DMF (0.2 mL) and 5-amino-o-cresol (16 mg, 0.13 mmol) was added. The reaction mixture was stirred overnight under argon at 25° C. Solvent was removed in vacuo, and the crude material was purified first by radial chromatography on a 1 mm silica gel plate eluting with a gradient of 2–5% methanol in chloroform, and then by preparative TLC (silica gel, 2% methanol in chloroform) to provide 6 mg (17%) of the title compound as yellowish solid. [M+H]⁺=389; ¹H NMR (CDCl₃): δ 8.05 (s, 1H), 7.98 (s, 1H), 7.47-7.44 (m, 5H), 7.14 (s, 1H), 6.88 (d, J=8.2 Hz, 1H), 6.87 (s, 1H), 6.28 (dd, J=8.2, 1.6 Hz, 1H), 5.47 (br s, 1H), 4.11 (q, J=7.1 Hz, 2H), 2.08 (s, 3H), 1.10 (t, J=7.1 Hz, 3H).

Example 19

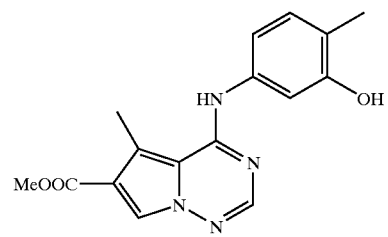

4-[(3-Hydroxy-4-methylphenyl)amino]-5-methylpyrrolo[2,1-f] [1,2,4]triazine-6-carboxylic Acid Methyl Ester

A. 3-methylpyrrole-2,4-dicarboxylic Acid Dimethyl Ester

To a suspension of aluminum chloride (106.4 g, 798 mmol) in dichloroethane (700 mL) at −40° C. under nitrogen was added dropwise trichloroacetyl chloride (89 mL, 798 mmol). A solution of 4-methylpyrrole-3-carboxylic acid methyl ester (37 g, 266 mmol, prepared by the procedure analogous to Compound A of Example 18 using methyl crotonate) in dichloroethane (200 mL) was added and the reaction mixture was gradually warmed to rt. and was stirred over the weekend (65 hr). A cold and pre-prepared aluminum chloride (53.2 g) and trichloroacetyl chloride (44.6 g) in dichloroethane (450 mL) was added to the reaction mixture. After an additional 24 hr, the mixture was care fully poured into an ice-water bath (2 L) and the pH of the solution was adjusted to 2.0. The organic layer was separated and the aqueous layer was extracted with dichloromethane. The combined organic extract was washed with 3 N HCl, brine, then dried ($Na_2SO_4$), and concentrated in vacuo to give dark oil. This oil was dissolved in methanol (400 mL), and the resulting solution was cooled 0° C. under nitrogen. To this solution was added sodium methoxide (25% in methanol) until the pH of the solution was 10. After 1 hr, the mixture was concentrated and then diluted with ice water (1 L) and the pH of the mixture was adjusted to 6. The mixture was extracted with dichlormethane (3×1 L). The combined extracts were washed with $NaHCO_3$, brine, dried ($Na_2SO_4$) and concentrated in vacuo. The brown solid obtained was purified by chromatography on silica gel eluting with ethyl acetate in hexanes to provide 44.3 g (84%) of Compound A. MS: $[M+H]^-$=196

B. 1-Amino-3-methylpyrrole-2,4-dicarboxylic Acid Dimethyl Ester

Compound B was prepared from compound A (46 g, 213 mmol) in a manner similar to Compound D of Example 18 except most of the solvent was removed prior to the addition of water. Thus, after purification by chromatography on silica gel eluting with 25–30% ethyl acetate in hexanes, 38 g (84%) of Compound B was obtained as white solid. ESI $[M+H]^+$=213.1

C. 5-Methylpyrrolo[2,1-f][1,2,4]triazin-4(3H)-one-6-carboxylic Acid Methyl Ester Compound B (38 g, 179 mmol) was combined with formamide (400 mL) and heated to 165° C. for 6 hr. The reaction was diluted with water (5 mL), extracted with ethyl acetate (3×10 mL), dried ($Na_2SO_4$) and concentrated. The crude material was purified by washing with ether/hexanes (7/3) to provide 33.4 g (90%) of Compound C as a white solid. ESI MS: $[M-H]^-$=206.0

D. 4-[(3-Hydroxy-4-methylphenyl)amino]-5-methylpyrrolo[2,1-f] [1,2,4]triazine-6-carboxylic Acid Methyl Ester The title compound was prepared in a manner similar to the preparation of compound F of example 18. Thus, after purification by preparative HPLC, 13.5 mg (42%) of the title compound was obtained as yellowish solid. ESI [M+H]$^+$=13.2; $^1$H NMR (CDCl$_3$): δ 7.97 (s, 1H), 7.92 (s, 1H), 7.36 (s, 1H), 7.12 (d, J=8.1 Hz, 1H), 6.88 (d, J=8.1 Hz, 1H), 3.86 (s, 2H), 2.90 (s, 3H), 2.21 (s, 3H).

Example 20

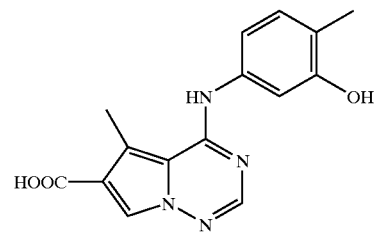

4-[(3-Hydroxy-4-methylphenyl)amino]-5-methylpyrrolo[2,1-f][1,2,4]triazine-6-carboxylic Acid A 1.0 M aqueous LiOH solution (0.16 mmol) was added to Example 19 (26 mg, 0.083 mmol) in a mixture of THF (0.6 mL), methanol (0.2 mL), and water (0.2 mL) at 0° C. The reaction mixture was warmed to 25° C. and stirred for 2 hrs. An additional solution of LiOH (0.5 mL) was added and the reaction was warmed to 50° C. for 1.25 hr. The reaction was brought to pH 7 with 5% aqueous HCl solution and extracted with ethyl acetate (4×7 mL). The organic extracts were dried (MgSO$_4$) and concentrated in vacuo to provide 16 mg (67%) of the title compound as off-white solid. MS: [M+H]$^+$ =299.2; $^1$H NMR (CD$_3$OD): δ 7.87 (s, 1H), 7.68 (s, 1H), 7.27 (s, 1H), 6.99 (d, J=8.2 Hz, 1H), 6.81 (s, 1H), 2.76 (s, 3H), 2.09 (s, 3H)

Example 21

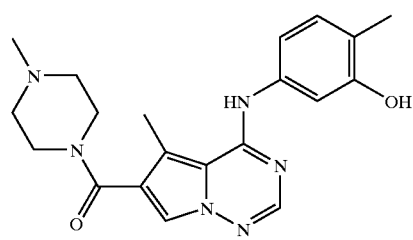

1-[[4-[(3-Hydroxy-4-methylphenyl)amino]-5-methylpyrrolo[2,1-f][1,2,4]triazin-6-yl] carbonyl]-4-methylpiperazine To a solution of Example 20 (7 mg, 0.023 mmol) in DMF (0.4 mL) at 25° C. was added N-methyl piperazine (3.5 μL, 0.03 mmol), 1-hydroxybenzotriazole (3 mg, 0.023 mmol) and 1 (3-dimethylaminopropyl)-3-ethylcarbodiimide hydrochloride (7 mg, 0.05 mmol). After 24 hrs., the mixture was concentrated, diluted with water (2 mL), and extracted with ethyl acetate (5×2 mL). The combined organic extracts were washed with saturated aqueous NaHCO$_3$ (2×5 mL). The crude material was purified by chromatography on silica gel eluting with a gradient of 5–10% methanol in chloroform to provide 6.23 mg (70%) of the title compound as white solid. MS: [M+H]$^+$=381.3; $^1$H NMR (CDCl$_3$): δ7.76 (s, 1H), 7.48

(s, 1H), 7.08 (s, 1H), 7.02 (d, J=8.2 Hz, 1H), 6.69 (d, J=8.2 Hz, 1H), 3.82-3.44 (m, 2H), 2.54 (s, 3H), 2.53-2.28 (m, 6H), 2.27 (s, 3H), 2.10 (s, 3H)

Example 22

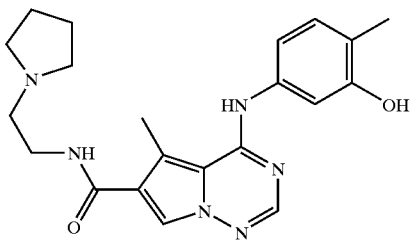

4-[(3-Hydroxy-4-methylphenyl)amino]-5-methyl-N-[2-(1-pyrrolidinyl)ethyl]pyrrolo [2,1-f][1,2,4]triazine-6-carboxamide Example 20 (7 mg, 0.023 mmol) was converted to 6 mg (65%) of the title compound as white solid in a manner similar to the preparation of Example 21 from Example 20. MS: [M+H]+=395.3; 1H NMR (DMF-d7): δ 9.56 (s, 1H), 8.40 (s, 1H), 7.42 (br s, 1H), 7.10-7.05 (m, 2H), 3.49-3.47 (m, 12H), 2.49 (s, 3H), 2.14 (s, 3H)

Example 23

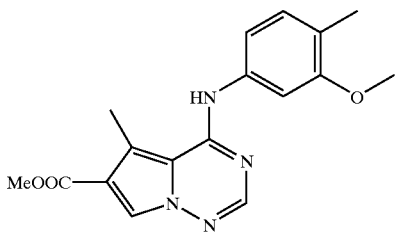

4-[(3-Methoxy-4-methylphenyl)amino]-5-methylpyrrolo[2,1-f][1,2,4]triazine-6-carboxylic Acid Methyl Ester To a solution of Example 19 (10.8 mg, 0.04 mmol) in CH3CN (0.5 mL) and methanol (0.1 mL) was added trimethylsilyl diazomethane (21 μL of 2.0 M solution in THF). After 24 hrs. TLC indicated no reaction had occurred. DMF (0.2 mL) and additional trimethylsilyl diazomethane (0.1 mL) were added and the reaction mixture was stirred for additional 24 hrs. After the addition of additional 1.1 eq. of trimethylsilyl diazomethane, LC/MS indicated the disappearance of starting alcohol. Acetic acid (2 drops) was added and the reaction mixture concentrated in vacuo. The crude material was purified first by chromatography on silica gel eluting with a gradient of 2-5% methanol in chloroform and then by preparative HPLC to provide 2.8 mg (25%) of Example 23 as white solid. [M+H]+=327.2; 1H NMR (CDCl3): δ 7.92 (s, 1H), 7.87 (s, 1H), 7.26 (s, 1H), 7.07 (d, J=8.1 Hz, 1H), 6.91 (d, J=8.1 Hz, 1H), 3.81 (s, 3H), 3.80 (s, 3H), 2.87 (s, 3H), 2.15 (s, 3H).

Example 24

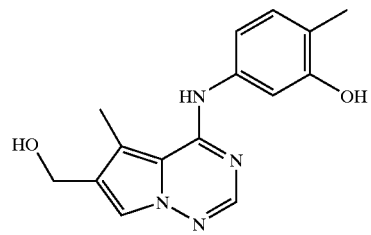

4-[(3-Hydroxy-4-methylphenyl)amino]-5-methylpyrrolo[2,1-f][1,2,4]triazine-6-methanol To a suspension of Example 19 (23 mg, 0.08 mmol) in CH2Cl2 (1 mL) at -78° C. under argon was added diisobutyl aluminum hydride (1.0 M in toluene, 0.15 mL). The reaction mixture was gradually warmed to 0° C. over 45 min. TLC indicated that starting material remained and an additional 1 equivalent of diisobutyl aluminum hydride was added at 0° C. After 20 min. the reaction mixture was poured into aqueous potassium sodium tartrate and stirred for 30 min. The mixture was extracted with CH2Cl2 (4×5 mL), dried (Na2SO4), and purified by chromatography on silica gel eluting with a gradient of 5-10% methanol in chloroform to provide 8 mg (38%) of Example 24 as a solid. MS: [M+H]+=285.2; 1H NMR (CD3OD): δ 7.70 (s, 1H), 7.56 (s, 1H), 7.19 (s, 1H), 7.08 (d, J=8.0 Hz, 1H), 6.89 (d, J=8.0 Hz, 1H), 4.68 (s, 2H), 2.62 (s, 3H), 2.20 (s, 3H)

Example 25

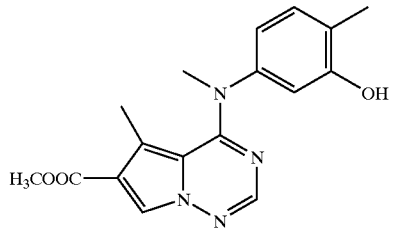

4-[(3-Hydroxy-4-methylphenyl)methylamino]-5-methylpyrrolo[2,1-f] [1,2,4]triazine-6-carboxylic Acid Methyl Ester A. 5-methyl-6-carbomethoxy-4-(3-tert-butyldimethylsilyloxy-4-methylphenylamino)-pyrrolo [2,1-f][1,2,4]triazine To a solution of Example 19 (31 mg, 0.1 mmol) in DMF (1 mL) at 25° C. under argon was added t-butyldimethylsilyl chloride (19 mg, 0.13 mmol) and imidazole (11 mg, 0.15 mmol). The reaction mixture was stirred 5 hrs at ambient temperature and then stored at -40° C. overnight. Water was added and the mixture was extracted with ethyl acetate (3×5 mL). The organic extracts were washed with brine (10 mL), dried (Na2SO4), and purified by chromatography on silica gel eluting with 25% ethyl acetate in hexanes to provide 42 mg (100%) of Compound A. MS: (M+H)+=427.4

B. 5-Methyl-6-carbomethoxy-4-(3-methoxy-4-methylphenyl-N-methylamino)-pyrrolo[2,1-f] [1,2,4]triazine To a solution of Compound A (29 mg, 68 μmol) in THF (0.7 mL) at 0° C. was added NaH (5.5 mg, 0.14 mmol). After stirring for 10 min. methyl iodide (17 μL, 0.27 mmol) was added followed by DMF (80 μL) and the reaction mixture was allowed to warm to 25° C. over 1 hr. After cooling to 0° C. the reaction was quenched with pH 7 phosphate buffer (1 mL) and extracted with ethyl acetate (3×2 mL). The combined organic extracts were dried ($Na_2SO_4$) and purified by chromatography on silica gel eluting with a gradient of 25–50% ethyl acetate in hexanes. The residue was taken up in THF (1 mL) and cooled to 0° C. Tetrabutylammonium fluoride (0.1 mL) was added and the reaction was stirred under argon at 0° C. for 45 min. The mixture was quenched with pH 7 phosphate buffer and extracted with ethyl acetate (3×2 mL). The organic extracts were dried ($Na_2SO_4$) and purified by rotary chromatography on a 1 mm silica gel plate eluting with 2% methanol in chloroform to provide 10 mg (50%) of the title compound as a white solid. MS: $[M+H]^+$=327.3; $^1H$ NMR ($CD_3OD$): δ 7.58 (s, 1H), 7.51 (s, 1H), 6.87 (d, J=7.7 Hz, 1H), 6.24 (s, 1H), 6.22 (d, J=7.7 Hz, 1H), 3.69 (s, 3H), 3.26 (s, 3H), 2.09 (s, 3H), 1.79 (s, 3H)

Example 26

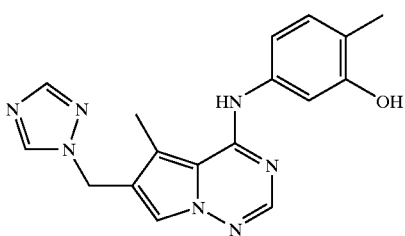

2-Methyl-5-[5-methyl-6-(1H-1,2,4-triazol-1-ylmethyl)pyrrolo[2,1-f][1,2,4]triazin-4-yl]amino]phenol

A. 5-methyl-6-hydroxymethyl-4-(3-tert-butyldimethylsilyloxy-4-methylphenylamino)-pyrrolo[2,1-f][1,2,4]triazine To a solution of Compound A of Example 24 (42 mg, 0.1 mmol) in $CH_2Cl_2$ (1 mL) at −78° C. under argon was added diisobutyl aluminum hydride (1.0 M in toluene, 0.30 mL). After 45 min. the reaction mixture was poured into aqueous potassium sodium tartrate and stirred for 40 min at 25° C. The mixture was extracted with ethyl acetate (3×5 mL). The combined organic extracts were washed with brine (10 mL), dried ($Na_2SO_4$) and concentrated to provide compound A which was used directly for the next step without further purification.

B. 5-(1,2,4-pyrazole)methyl-6-hydroxy-4-(3-methoxy-4-methylphenylamino)-pyrrolo [2,1-f][1,2,4]triazine To a solution of Compound A (20 mg, 50 μmol) in $CH_2Cl_2$ (1 mL) at 0° C. was added triethylamine (75 μmol) and methane sulfonyl chloride (55 μmol). The reaction mixture was warmed to 25° C. and stirred for 1 hr. The mixture was concentrated in vacuo. In a separate vial 1,2,4-triazole (10 mg, 0.15 mmol) was added to NaH (6 mg, 0.15 mmol) in DMF (1 mL) at 0° C. under argon. This mixture was warmed to 25° C. and stirred for 15 min. and then cooled back to 0° C. The mesylate was dissolved in 0.5 mL of DMF and added to the second vial. The reaction was warmed to 25° C. and stirred for 3 hrs. Water (2 mL) was added and the mixture was extracted with ethyl acetate (3×5 mL). The combined organic extracts were dried ($Na_2SO_4$), and purified by preparative TLC on a 1 mm silica gel plate eluting with 5% methanol in chloroform. The material obtained was dissolved in THF and cooled to 0° C. Tetrabutyl ammonium fluoride (2.0 eq) was added and the mixture was stirred under argon at 0° C. for 30 min. The material was concentrated and purified directly by preparative TLC on a 1 mm silica gel plate eluting twice with 5% methanol in chloroform to provide 2.1 mg (10%) of the title compound. MS: $[M+H]^+$=336.2; $^1H$ NMR ($CD_3OD$): δ 8.36 (s, 1H), 7.89 (s, 1H), 7.62 (s, 1H), 7.55 (s, 1H), 7.07 (s, 1H), 6.96 (d, J=7.9 Hz, 1H), 6.78 (d, J=7.9 Hz, 1H), 5.39 (s, 2H), 2.48 (s, 3H), 2.08 (s, 3H)

Example 27

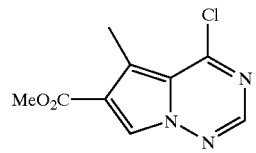

4-chloro-5-methyl-6-carbomethoxypyrrolo[2,1-f][1,2,4]triazine

Phosphorous oxychloride (2.5 mL) was combined with Compound C of Example 19 (100 mg, 0.483 mmol) and heated at 100° C. overnight. The melt was allowed to cool to rt and dissolved in ethyl acetate. The mixture was neutralized with aqueous $NaHCO_3$ and extracted twice with ethyl acetate. The combined organic washes were dried ($Na_2SO_4$) and concentrated to provide 101 mg (93%) of Example 27. MS: $(M+H)^+$226.6

Example 28

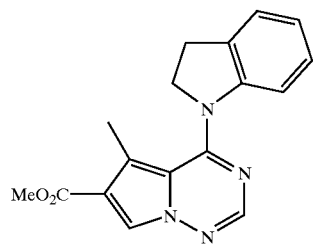

4-(2,3-Dihydro-1H-indol-1-yl)-5-methylpyrrolo[2,1-f][1,2,4]triazine-6-carboxylic Acid Methyl Ester A mixture of Example 27 (20 mg, 0.09 mmol) and indoline (21 mg, 0.177 mmol) in $CH_3CN$ (1 mL) was shaken for 4 hrs. DMF (0.2 mL) was added, and the crude mixture was purified by preparative HPLC to provide 12.2 mg (45%) of Example 28 as a white solid. [M+H]$^+$=309.2; $^1$H NMR (CDCl$_3$): δ 8.06 (s, 1H), 7.91 (s, 1H), 7.20 (m, 1H), 7.01 (m, 1H), 6.93-6.91 (m, 2H), 4.15 (t, J=7.8 Hz, 2H), 3.81 (s, 3H), 3.09 (t, J=7.8 Hz, 2H), 2.35 (s, 3H).

Example 29

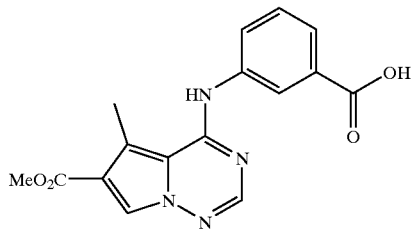

4-[(3-Carboxyphenyl)amino]-5-methylpyrrolo[2,1-f] [1,2,4]triazine-6-carboxylic Acid Methyl Ester A mixture of Example 27 (20 mg, 0.09 mmol), triethylamine (0.1 mL), and 3-amino benzoic acid (24 mg, 0.177 mmol) in CH$_3$CN (1 mL) was shaken for 4 hrs. The mixture was filtered, washing with CH$_3$CN, and the crude material was purified by preparative HPLC to provide Example 29 as a solid. [M+H]$^+$=327.1; $^1$H NMR (CDCl$_3$): δ 9.24 (br s, 1H), 8.11 (s, 1H), 7.91 (m, 1H), 7.73-7.58 (m, 4H), 3.80 (s, 3H), 2.83 (s, 3H).

Example 30

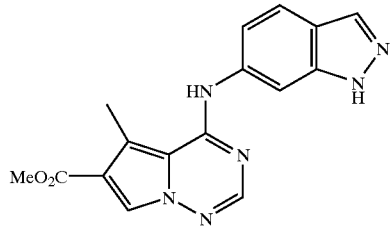

4-(1H-Indazol-6-ylamino)-5-methylpyrrolo[2,1-f][1,2,4]triazine-6-carboxylic Acid Methyl Ester A mixture of Example 27 (20 mg, 0.09 mmol) and 6-aminoindazole (18 mg, 0.13 mmol) in CH$_3$CN (1 mL) and DMSO (0.5 mL) was shaken for 4 hrs. The mixture was filtered, washed with CH$_3$CN, and the crude material was purified by preparative HPLC to provide Example 30 as a white solid (13 mg, 45%). [M+H]$^+$=323.1; $^1$H NMR (CDCl$_3$): δ 8.37 (s, 1H), 7.99 (s, 1H), 7.94 (d, J=7.4 Hz, 1H), 7.68 (d, J=4.2 Hz, 1H), 7.00 (dd, J=7.4, 4.2 Hz, 1H), 3.83 (s, 3H), 2.91 (s, 3H).

Example 31

4-[[3-Hydroxy-4-[(phenylsulfonyl)amino]phenyl] amino]-5-methylpyrrolo[2,1-f] [1,2,4]triazine-6-carboxylic Acid Methyl Ester A mixture of Example 27 (20 mg, 0.09 mmol) and 4'-amino-2'-hydroxybenzenesulfonanilide (18 mg, 0.13 mmol) in DMF (1 mL) was shaken for 4 hrs. The mixture was purified by preparative HPLC to provide Example 31 as a solid (7 mg, 18%). [M+H]$^+$=454.2; $^1$H NMR (CDCl$_3$): δ 7.92 (s, 1H), 7.76 (s, 1H), 7.69 (d, J=7.8 Hz, 1H), 7.51-7.40 (m, 6H), 6.85 (m, 2H), 6.37 (s, 1H), 3.84 (s, 3H), 2.82 (s, 3H).

Example 32

4-(2-Benzothiazolylamino)-5-methylpyrrolo[2,1-f] [1,2,4]triazine-6-carboxylic Acid Methyl Ester To a 0° C. mixture of NaH (60%, 5 mg, 0.106 mmol) in DMF (0.5 mL) was added 25 aminobenzothiazole (16 mg, 0.106 mmol). The reaction mixture was stirred for 10 min. at 0° C. Example 27 (20 mg, 0.09 mmol) was added in DMF (1 mL). The reaction mixture was stirred for 45 min. at 25° C. and then quenched with pH 7 phosphate buffer. The mixture was extracted with ethyl acetate. The combined extracts were dried (Na$_2$SO$_4$) and purified by preparative HPLC to provide Example 32 as a solid (12 mg, 40%). [M+H]$^+$=340.2; $^1$H NMR (CDCl$_3$): δ 8.41 (s, 1H), 8.28 (s, 1H), 7.28 (d, J=7.2 Hz, 1H), 7.08 (m, 2H), 6.57 (d, J=7.2 Hz, 1H), 3.82 (s, 3H), 2.38 (s, 3H).

Example 33

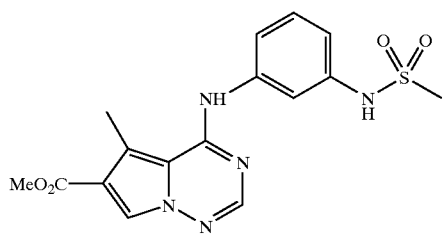

5-Methyl-4-[[3-[(methylsulfonyl)amino]phenyl] amino]pyrrolo[2,1-f][1,2,4]triazine-6-carboxylic Acid Methyl Ester Phosphorus oxychloride was combined with Example 19 (30 mg, 0.14 mmol) and heated to 100° C. for 15 hrs. The melt was cooled and concentrated to remove excess reagent, then extracted with ethyl acetate (20 mL). The extract was washed with sat aqueous NaHCO$_3$, (10 mL) dried over MgSO$_4$ and concentrated in vacuo to provide chlorinated compound Example 27. The residue was dissolved in DMF (2 mL) and 3(methylsulfonylamino)aniline (54 mg, 0.3 mmol) was added. The reaction mixture was stirred for 4 hrs under argon at 25° C. The crude reaction mixture was purified by preparative HPLC. The material obtained appeared to be a salt of the desired compound. The material was dissolved in ethyl acetate and washed with saturated aqueous NaHCO$_3$. Evaporation of the solvent gave 24 mg (40%) of Example 33. MS: [M+H]$^+$=376.2; $^1$H NMR (d-DMSO): δ 8.89 (s, 1H), 8.14 (s, 1H), 7.95 (s, 1H), 7.55 (s, 1H), 7.38 (s, 1H), 7.34-7.32 (m, 2H), 7.01 (d, J=8.0 Hz, 1H), 3.81 (s, 3H), 3.02 (s, 3H), 2.82 (s, 3H).

Example 34

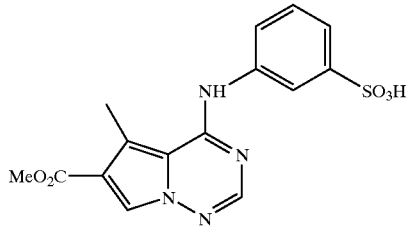

4-[[3-(Hydroxysulfonyl)phenyl]amino]-5-methylpyrrolo[2,1-f][1,2,4]triazine-6-carboxylic Acid Methyl Ester Example 27 (20 mg, 0.09 mmol) was dissolved in DMF (1 mL) and 3-aminobenzenesulfonic acid (23 mg, 0.13 mmol) was added. After 5 hr at rt, the crude reaction mixture was purified by preparative HPLC. The material obtained appeared to be a salt of the desired compound. The material was dissolved in ethyl acetate and washed with saturated aqueous NaHCO$_3$. Evaporation of the solvent gave 9.7 mg (30%) of Example 34. MS: [M+H]$^+$=363.2; $^1$H NMR (CDCl$_3$/CD$_3$OD): δ 8.04 (s, 1H), 7.82 (d, J=7.1 Hz, 1H), 7.65 (s, 1H), 7.52-7.42 (m, 1H), 7.31-7.26 (m, 2H), 3.73 (s, 3H), 2.75 (s, 3H).

Example 35

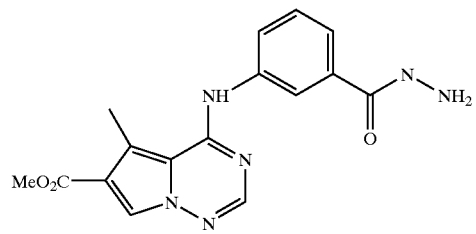

4-[[3-(Hydrazinocarbonyl)phenyl]amino]-5-methylpyrrolo[2,1-f][1,2,4]triazine-6-carboxylic Acid Methyl Ester Example 35 was prepared from 3-aminobenzhydrazide (30 mg, 0.2 mmol) and Example 27 (30 mg, 1 mmol) in a manner similar to the preparation of Example 28 to afford 6 mg (18%) of solid. MS: [M+H]$^+$=341.2; $^1$H NMR (d-DMSO): δ 7.79 (s, 1H), 7.58 (s, 1H), 7.11-7.05 (m, 3H), 6.72 (d, J=8.1 Hz, 1H), 5.23 (br s, 2H), 3.76 (s, 3H), 2.67 (s, 3H)

Example 36

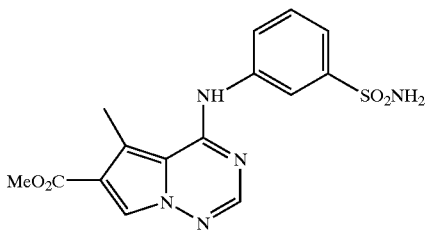

4-[[3-(Aminosulfonyl)phenyl]amino]-5-methylpyrrolo[2,1-f][1,2,4]triazine-6-carboxylic Acid Methyl Ester Example 27 (20 mg, 0.09 mmol) was treated with 3-aminobenzenesulfonamide (23 mg, 0.13 mmol) in a manner similar to that described for Example 31. Evaporation of the extracting solvent gave 18.6 mg (58%) of solid. MS: [M+H]$^+$=362; $^1$H NMR (d-DMSO): δ 9.08 (s, 1H), 8.18 (s, 2H), 7.98 (s, 1H), 7.91-7.89 (m, 1H), 7.62-7.58 (m, 2H), 7.42 (s, 2H), 3.81 (s, 3H), 2.84 (s, 3H)

Example 37

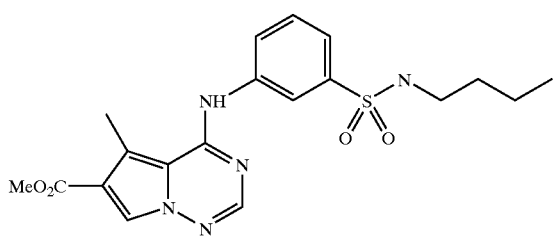

4-[[3-[(Butylamino)sulfonyl]phenyl]amino]-5-methylpyrrolo[2,1-f][1,2,4]triazine-6-carboxylic Acid Methyl Ester Example 27 (20 mg, 0.09 mmol) was treated with N-butyl-3-amino-benzenesulfonamide (30 mg, 0.13 mmol) in a manner similar to that described for Example 31. Evaporation of the extracting solvent gave 31 mg (89%) of solid. MS: [M+H]$^+$= 418.2; $^1$H NMR (CDCl$_3$): δ 8.07 (s, 1H), 7.97 (s, 1H), 7.85 (s, 1H), 7.84-7.82 (m, 1H), 7.58 (d, J=8.0 Hz, 1H), 7.49-7.45 (m, 2H), 3.82 (s, 3H), 2.93-2.89 (m, 2H), 2.81 (s, 3H), 1.44-1.18 (m, 4H), 0.84 (t, J=7.4 Hz, 3H)

Example 38

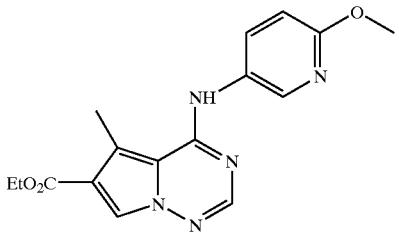

4-[(6-Methoxy-3-pyridinyl)amino]-5-methylpyrrolo[2,1-f][1,2,4]triazine-6-carboxylic Acid Ethyl Ester Example 27 (20 mg, 0.09 mmol) was dissolved in DMF (1 mL) and 5-amino-2-methoxypyridine (16 mg, 0.13 mmol) was added. The reaction mixture was stirred for 2.5 hrs under argon at 25° C. The crude reaction mixture was concentrated and purified directly by chromatography on silica gel eluting with a gradient of 25–50% ethyl acetate in hexanes. The material obtained was dissolved in ethanol (2 mL) and sodium ethoxide (20%, 0.3 g, 10 eq) was added. The mixture was stirred at 75° C. for 3 hrs. The crude material was purified directly by preparative HPLC to provide 4.3 mg (15%) of an off-white solid. MS: [M+H]$^+$=314.2; $^1$H NMR (CDCl$_3$): δ 8.25 (d, J=2.7 Hz, 1H), 7.93 (s, 1H), 7.85 (d, J=8.8 Hz, 1H), 7.82 (s, 1H), 7.09 (br s, 1H), 6.74 (d, J=8.8 Hz, 1H), 3.89 (s, 3H), 3.82 (s, 3H), 2.86 (s, 3H)

Example 39

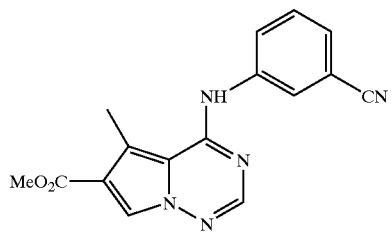

4-[1(3-Cyanophenyl)amino]-5-methylpyrrolo[12,1-f][1,2,4]triazine-6-carboxylic Acid Methyl Ester The title compound was prepared from Example 27 (20 mg, 0.09 mmol) and 3-aminobenzonitrile (21 mg, 0.177 mmol) by the procedure analogous to Example 28. MS: [M+H]$^+$=308.2; $^1$H NMR (CDCl$_3$): δ8.23 (s, 1H), 7.97 (s, 1H), 7.93 (s, 1H), 7.75 (d, J=6.3 Hz, 1H), 7.46-7.36 (m, 3H), 3.82 (s, 3H), 2.89 (s, 3H)

Example 40

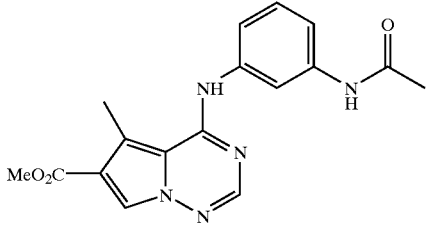

4-[3-(Acetylamino)phenyl]amino]-5-methylpyrrolo[2,1-f][1,2,4]triazine-6-carboxylic Acid Methyl Ester The title compound was prepared from Example 27 (20 mg, 0.09 mmol) and 3'-aminoacetanilide (27 mg, 0.177 mmol) by the procedure analogous to Example 28. MS: [M+H]$^+$=340.2; $^1$H NMR (CDCl$_3$): δ 7.81 (s, 1H), 7.75 (s, 1H), 7.51 (s, 1H), 7.20-7.07 (m, 3H), 3.80 (s, 3H), 2.84 (s, 3H), 1.90 (s, 3H)

Example 41

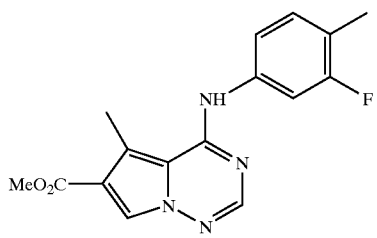

4-[(3-Fluoro-4-methylphenyl)amino]-5-methylpyrrolo[2,1-f][1,2,4]triazine-6-carboxylic Acid Methyl Ester The title compound was prepared from Example 27 (20 mg, 0.09 mmol) and 3-fluoro-4-methylaniline (17 mg, 0.13 mmol) by the procedure analogous to Example 28. MS: [M+H]$^+$=315.2; $^1$H NMR (CDCl$_3$): δ 7.92 (s, 1H), 7.87 (s, 1H), 7.57 (d, J=2.8 Hz, 1H), 7.19-7.09 (m, 3H), 3.81 (s, 3H), 2.87 (s, 3H), 2.20 (s, 3H)

Example 42

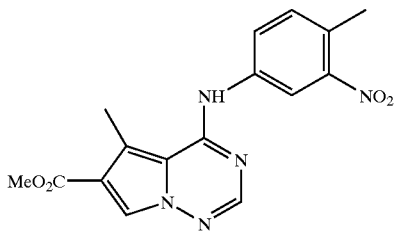

5-Methyl-4-[(4-methyl-3-nitrophenyl)amino]pyrrolo[2,1-f][1,2,4]triazine-620 carboxylic Acid Methyl Ester The title compound was prepared from Example 27 (20 mg, 0.09 mmol) and 3-nitro-4-methylaniline (20 mg, 0.13 mmol) by the procedure analogous to Example 28. MS: [M+H]$^+$=342.2; $^1$H NMR (CDCl$_3$): δ 8.39 (s, 1H), 7.96 (s, 1H), 7.91 (s, 1H), 7.30 (d, J=6.5 Hz, 1H), 7.19 (d, J=6.5 Hz, 1H), 3.83 (s, 3H), 2.89 (s, 3H), 2.54 (s, 3H)

Example 43

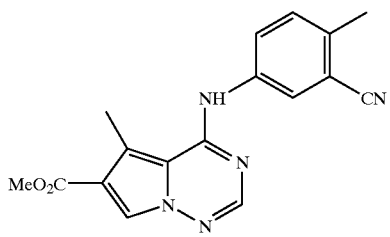

4-[(3-Cyano-4-methylphenyl)amino]-5-methylpyrrolo[2,1-f][1,2,4]triazine-6-carboxylic Acid Methyl Ester The title compound was prepared from Example 27 (20 mg, 0.09 mmol) and 3-cyano-4-methylaniline (18 mg, 0.13 mmol) by the procedure analogous to Example 28. MS: [M+H]$^+$=323.2; $^1$H NMR (CDCl$_3$): δ 8.08 (s, 1H), 7.96 (s, 1H), 7.90 (s, 1H), 7.61 (d, J=8.2 Hz, 1H), 7.28 (d, J=8.2 Hz, 1H), 3.82 (s, 3H), 2.87 (s, 3H), 2.48 (s, 3H)

Example 44

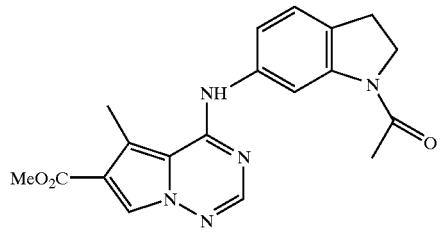

4-[1(1-Acetyl-2,3-dihydro-1H-indol-6-yl)amino]-5-methylpyrrolo[2,1-f] [1,2,4]-triazine-6-carboxylic Acid Methyl Ester The title compound was prepared from Example 27 (20 mg, 0.09 mmol) and 1-acetyl-6-aminoindoline (23 mg, 0.13 mmol) by the procedure analogous to Example 28. MS: [M+H]$^+$=366.2; $^1$H NMR (CDCl$_3$): δ 8.14 (d, J=8.6 Hz, 1H), 7.95 (s, 1H), 7.82 (s, 1H), 7.51 (s, 1H), 7.12 (d, J=8.6 Hz, 1H), 4.03 (t, J=7.8 Hz, 2H), 3.81 (s, 3H), 3.18 (t, J=7.8 Hz, 2H), 2.67 (s, 3H), 2.19 (s, 3H)

Example 45

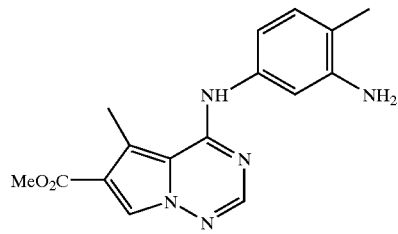

4-[(3-Amino-4-methylphenyl)amino]-5-methylpyrrolo[2,1-f][1,2,4]triazine-6-carboxylic Acid Methyl Ester The title compound was prepared from Example 27 (20 mg, 0.09 mmol) and 3-amino-4-methylaniline (16 mg, 0.13 mmol) by the procedure analogous to Example 28. MS: [M+H]$^+$=312.2; $^1$H NMR (CDCl$_3$): δ 7.92 (s, 1H), 7.90 (s, 1H), 7.11 (s, 1H), 6.96 (d, J=8.2 Hz, 1H), 6.74 (d, J=8.2 Hz, 1H), 3.81 (s, 3H), 2.85 (s, 2H), 2.18 (s, 3H)

Example 46

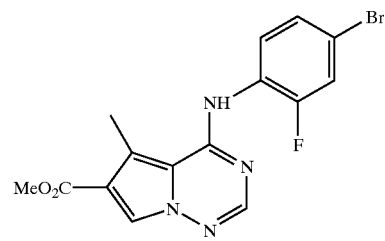

4-[(4-Bromo-2-fluorophenyl)amino]-5-methylpyrrolo[2,1-f][1,2,4]triazine-6-carboxylic Acid Methyl Ester The title compound was prepared from Example 27 (20 mg, 0.09 mmol) and 2-fluoro-4-bromoaniline (25.1 mg, 0.13 mmol) by the procedure analogous to Example 28. MS: [M+H]$^+$=379.1; $^1$H NMR (CDCl$_3$): δ 8.52 (t, J=8.8 Hz, 1H), 7.95 (s, 1H), 7.92 (s, 1H), 7.60 (br s, 1H), 7.30 (m, 2H), 3.82 (s, 3H), 2.86 (s, 3H)

Example 47

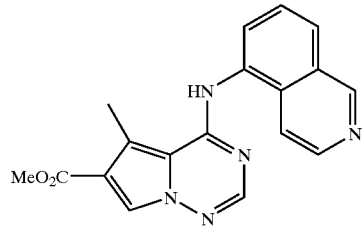

4-(5-isoquinolinylamino)-5-Methylpyrrolo[2,1-f][1,2,4]triazine-6-carboxylic Acid Methyl Ester The title compound was prepared from Example 27 (20 mg, 0.09 mmol) and 5-amino isoquinoline (19 mg, 0.13 mmol) by the procedure analogous to Example 28. MS: [M+H]$^+$=334.2; $^1$H NMR (CDCl$_3$): δ 8.12 (s, 1H), 8.09 (s, 1H), 7.10 (t, J=7.6 Hz, 1H), 6.83 (d, J=7.6 Hz, 1H), 6.70 (d, J=7.6 Hz, 1H), 6.59 (dd, J=7.7, 4.2 Hz, 1H), 6.01 (d, J=8.2 Hz, 1H), 3.82 (s, 3H), 2.71 (s, 3H)

Example 48

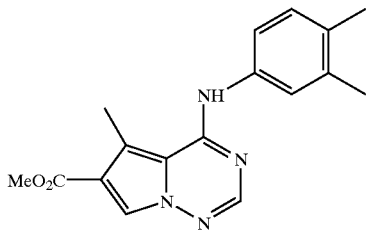

4-[(3,4-Dimethylphenyl)amino]-5-methylpyrrolo[2,1-f][1,2,4]triazine-6-carboxylic Acid Methyl Ester The title compound was prepared from Example 27 (20 mg, 0.09 mmol) and 3,4-dimethylaniline (16 mg, 0.13 mmol) by the procedure analogous to Example 28. MS: [M+H]$^+$=310.2; $^1$H NMR (CDCl$_3$): δ 7.90 (s, 1H), 7.84 (s, 1H), 7.31 (s, 1H), 7.20 (d, J=8.1 Hz, 1H), 7.08 (d, J=8.1 Hz, 1H), 3.80 (s, 3H), 2.84 (s, 3H), 2.22 (s, 3H), 2.18 (s, 3H)

Example 49

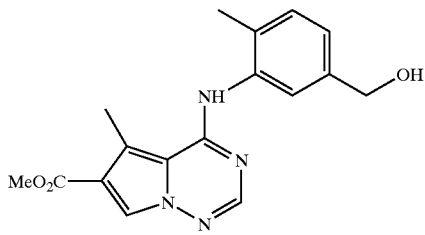

4-[[5-(Hydroxymethyl)-2-methylphenyl]amino]-5-methylpyrrolo[2,1-f] [1,2,41]triazine-6-carboxylic Acid Methyl Ester The title compound was prepared from Example 27 (20 mg, 0.09 mmol) and 3-amino-5-(hydroxymethyl)-2-methylaniline(18 mg, 0.13 mmol) by the procedure analogous to Example 28. MS: [M+H]$^+$=327.2; $^1$H NMR (CDCl$_3$): δ 7.93 (s, 1H), 7.87 (s, 1H), 7.83 (s, 1H), 7.36-7.21 (m, 3H), 4.65 (s, 2H), 3.80 (s, 3H), 2.87 (s, 3H), 2.28 (s, 3H)

Example 50

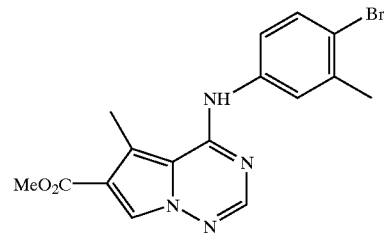

4-[(4-Bromo-3-methylphenyl)amino]-5-methylpyrrolo[2,1-f][1,2,4]triazine-6-carboxylic Acid Methyl Ester The title compound was prepared from Example 27 (20 mg, 0.09 mmol) and 4-bromo-3-methylaniline (25 mg, 0.13 mmol) by the procedure analogous to Example 28. MS: [M+H]$^+$=376.2; $^1$H NMR (CDCl$_3$): δ 7.91 (s, 1H), 7.89 (s, 1H), 7.45 (m, 1H), 7.34 (m, 1H), 7.20 (m, 1H), 3.81 (s, 3H), 2.84 (s, 3H), 2.35 (s, 3H)

Example 51

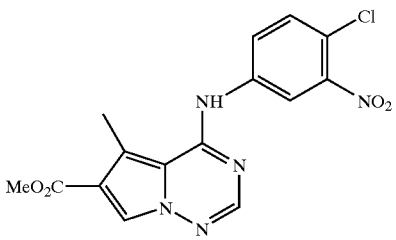

4-[(4-Chloro-3-nitrophenyl)amino]-5-methylpyrrolo[2,1-f][1,2,4]triazine-6-carboxylic Acid Methyl Ester The title compound was prepared from Example 27 (20 mg, 0.09 mmol) and 4-chloro-3-nitroaniline (23 mg, 0.13 mmol) by the procedure analogous to Example 28. MS: [M+H]$^+$=362.7; $^1$H NMR (CDCl$_3$): δ 8.48 (s, 1H), 8.00 (s, 1H), 7.94 (s, 1H), 7.75 (dd, J=8.7, 2.5 Hz, 1H), 7.48 (d, J=8.6 Hz, 1H), 7.38 (s, 1H), 3.83 (s, 3H), 2.89 (s, 3H)

Example 52

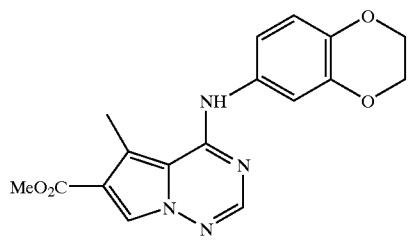

4-[(2,3-Dihydro-1,4-benzodioxin-6-yl)amino]-5-methylpyrrolo[2,1-f] [1,2,4]triazine-6-carboxylic Acid Methyl Ester The title compound was prepared from Example 27 (20 mg, 0.09 mmol) and (2,3-dihydro-1,4-benzodioxin-6-yl) amine (20 mg, 0.13 mmol) by the procedure analogous to Example 28. MS: [M+H]+=340.3; $^1$H NMR (CDCl$_3$): δ 7.90 (s, 1H), 7.84 (s, 1H), 7.24 (s, 1H), 7.14 (s, 1H), 6.91 (d, J=8.4 Hz, 1H), 6.81 (dd, J=8.4, 2.4 Hz, 1H), 4.20 (m, 4H), 3.80 (s, 3H), 2.83 (s, 3H)

Example 53

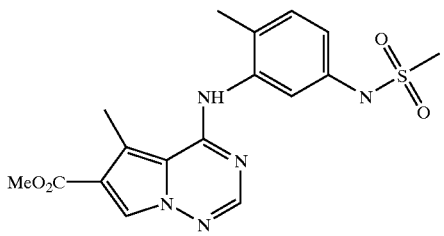

5-Methyl-4-[[2-methyl-5-[(methylsulfonyl)amino]phenyl]amino] pyrrolo[2,1-f] [1,2,4]triazine-6-carboxylic Acid Methyl Ester The title compound was prepared from Example 27 (20 mg, 0.09 mmol) and 2-methyl-5-(methylsulfonyl)aniline (27 mg, 0.13 mmol) by the procedure analogous to Example 28. MS: [M+H]$^+$=390.2; $^1$H NMR (CDCl$_3$): δ 8.04 (br s, 1H), 7.95 (s, 1H), 7.87 (s, 1H), 7.09-6.99 (m, 2H), 3.82 (s, 3H), 3.00 (s, 3H), 2.89 (s, 3H), 2.28 (s, 3H)

Example 54

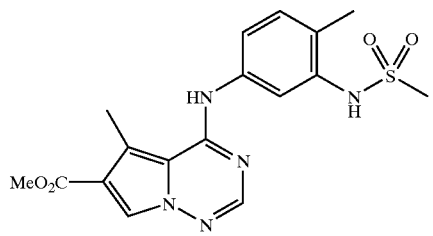

5-Methyl-4-[[4-methyl-3-[(methylsulfonyl)amino]phenyl]amino]pyrrolo[2,1][1,2,4]triazine-6-carboxylic Acid Methyl Ester To a solution of Example 53 (16 mg, 51 μmol) in pyridine (1 mL) at 0° C. was added 4-methyl-3-[(methylsulfonyl)aniline (4.4 μL, 87 μmol). The reaction mixture was stirred for 1 hr at 0° C. and then warmed to 25° C. and stirred for 4 hrs. Water (5 mL) was added and the mixture was extracted with ethyl acetate (3×5 mL). The combined organic extracts were washed with water (10 mL) and brine (10 mL) and dried (Na$_2$SO$_4$). The crude material was purified by chromatography on silica gel eluting with 2% methanol in chloroform to provide 6.9 mg (30%) of solid. MS: [M+H]$^+$= 390.2; $^1$H NMR (CDCl$_3$): δ 7.93 (s, 1H), 7.86 (s, 1H), 7.77 (s, 1H), 7.35 (d, J=8.2 Hz, 1H), 7.27 (s, 1H), 7.18 (d, J=8.2 Hz, 1H), 6.25 (s, 1H), 3.82 (s, 3H), 3.03 (s, 3H), 2.86 (s, 3H), 2.24 (s, 3H)

Example 55

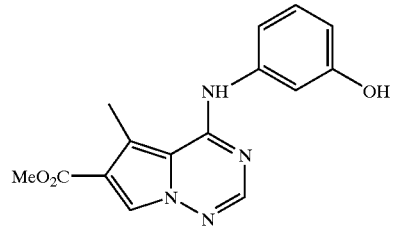

4-[(3-Hydroxyphenyl)amino]-5-methylpyrrolo[2,1-f] [1,2,4]triazine-6-carboxylic Acid Methyl Ester The title compound was prepared from Example 27 (20 mg, 0.09 mmol) and 3-hydroxyaniline (14 mg, 0.13 mmol) by the procedure analogous to Example 28. MS: [M+H]$^+$=299.1; $^1$H NMR (CDCl$_3$): δ 7.93 (s, 1H), 7.88 (s, 1H), 7.70 (s, 1H), 7.30 (br s, 1H), 6.97 (d, J=8.5 Hz, 1H), 6.60 (dd, J=8.4, 2.3 Hz, 1H), 3.82 (s, 3H), 2.68 (s, 3H).

Example 56

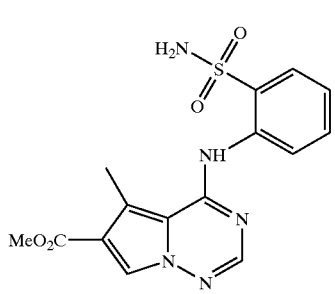

4-[2-(Aminosulfonyl)phenyl]amino]-5-methylpyrrolo[2,1-f][1,2,4]triazine-6-carboxylic Acid Methyl Ester The title compound was prepared from Example 27 (20 mg, 0.09 mmol) and 3-(aminosulfonyl)aniline (23 mg, 0.13 mmol) by the procedure analogous to Example 28. MS: [M+H]$^+$=362.1; $^1$H NMR (CDCl$_3$): δ 8.97 (s, 1H), 8.10 (d, J=8.1 Hz, 1H), 7.92 (d, J=8.1 Hz, 1H), 7.80 (s, 1H), 7.77 (s, 1H), 7.56 (t, J=8.2 Hz, 1H), 7.52 (t, J=8.2 Hz, 1H), 5.53 (s, 2H), 3.80 (s, 3H), 2.73 (s, 3H)

Example 57

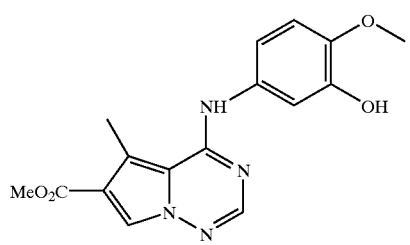

4-[(3-Hydroxy-4-methoxyphenyl)amino]-5-methylpyrrolo[2,1-f][1,2,4]triazine-6-carboxylic Acid Methyl Ester The title compound was prepared from Example 27 (28 mg, 0.124 mmol) and 5-amino-2-methoxy-phenol (20 mg, 0.148 mmol) by the procedure analogous to Example 28. MS: [M+H]$^+$=329.2; $^1$H NMR (CDCl$_3$): δ 7.90 (s, 1H), 7.84 (s, 1H), 7.19 (d, J=8.1 Hz, 1H), 7.18 (s, 1H), 7.02 (d, J=8.1 Hz, 1H), 5.73 (s, 1H), 3.83 (s, 3H), 3.78 (s, 3H), 2.84 (s, 3H).

Example 58

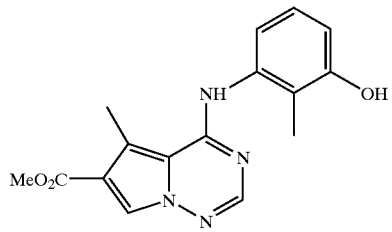

4-[(3-Hydroxy-2-methylphenyl)amino]-5-methylpyrrolo[2,1-f][1,2,4]triazine-6-carboxylic Acid Methyl Ester The title compound was prepared from Example 27 (28 mg, 0.124 mmol) and 3-amino-2-methylphenol (18 mg, 0.148 mmol) by the procedure analogous to Example 28. MS: [M+H]$^+$=313.2; $^1$H NMR (CD$_3$OD): δ 7.90 (s, 1H), 7.76 (s, 1H), 6.97 (t, J= 7.6 Hz, 1H), 6.80 (d, J=7.4 Hz, 1H), 6.68 (d, J=7.4 Hz, 1H), 3.80 (s, 3H), 2.66 (s, 3H), 2.55 (s, 3H).

Example 59

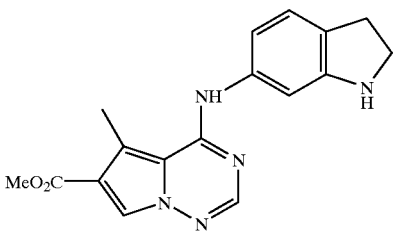

4-[(2,3-Dihydro-1H-indol-6-yl)amino]-5-methylpyrrolo[2,1-f][1,2,4]triazine-6-carboxylic Acid Methyl Ester The title compound was prepared from Example 27 (20 mg, 0.09 mmol) and (2,3-dihydro-1H-indol-6-yl)amine (27 mg, 0.13 mmol) by the procedure analogous to Example 29. MS: [M+H]$^+$=324.2; $^1$H NMR (CDCl$_3$): δ 8.05 (s, 1H), 7.91 (s, 1H), 6.97 (d, J=7.8 Hz, 1H), 6.31 (s, 1H), 6.23 (d, J=7.8 Hz, 1H), 4.22 (t, J=7.7 Hz, 2H), 3.84 (s, 3H), 2.84 (t, J=7.7 Hz, 2H), 2.55 (s, 3H).

Example 60

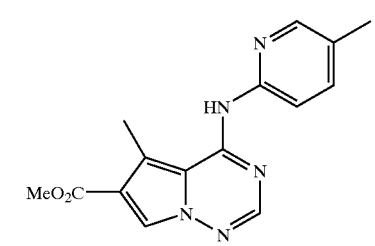

5-Methyl-4-[(5-methyl-2-pyridinyl)amino]pyrrolo[2,1-f][1,2,4]triazine-6-carboxylic Acid Methyl Ester The title compound was prepared from Example 27 (20 mg, 0.09 mmol) and (5-methyl-2-pyridinyl)amine (14 mg, 0.13 mmol) by the procedure analogous to Example 30. MS: [M+H]$^+$=298.2; $^1$H NMR (CDCl$_3$): δ 8.33 (s, 1H), 8.22 (s, 1H), 6.75 (d, J=8.7 Hz, 1H), 6.68 (s, 1H), 6.37 (d, J=8.7 Hz, 1H), 3.81 (s, 3H), 2.44 (s, 3H), 1.92 (s, 3H)

Example 61

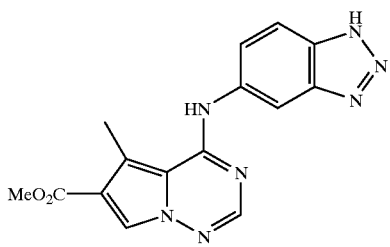

4-[(1H-Benzotriazol-5-yl)amino]-5-methylpyrrolo[2,1-f][1,2,4]triazine-6-carboxylic Acid Methyl Ester The title compound was prepared from Example 27 (20 mg, 0.09 mmol) and (1H-Benzotriazol-5-yl)amine (114 mg, 0.13 mmol) by the procedure analogous to Example 30. MS: [M+H]$^+$=324.2; $^1$H NMR (CDCl$_3$): δ 8.61 (s, 1H), 7.97 (s, 1H), 7.76 (s, 1H), 7.67 (d, J=8.1 Hz, 1H), 7.54 (s, 1H), 7.46 (d, J=8.1 Hz, 1H), 3.85 (s, 3H), 2.49 (s, 3H).

Example 62

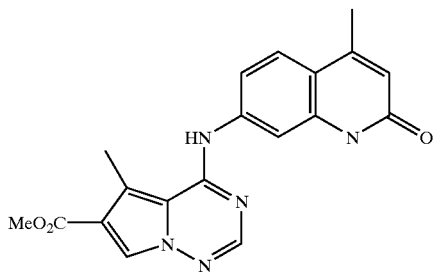

4-[(1,2-Dihydro-4-methyl-2-oxo-7-quinolinyl)amino]-5-methylpyrrolo[2,1-f][1,2,4]triazine-6-carboxylic Acid Methyl Ester The title compound was prepared from Example 27 (20 mg, 0.09 mmol) and (1,2-dihydro-4-methyl-2-oxo-7-quinolinyl)amine (14 mg, 0.13 mmol) by the procedure analogous to Example 30. MS: [M+H]$^+$=314.2; $^1$H NMR (d-DMSO): δ 8.09 (br s, 1H), 7.84 (s, 1H), 7.71 (s, 1H), 7.55 (m, 2H), 7.47 (s, 1H), 3.81 (s, 3H), 2.56 (s, 3H), 2.44 (s, 3H).

Example 63

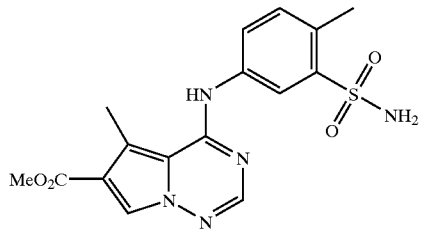

4-[[3-(Aminosulfonyl)-4-methylphenyl]amino]-5-methylpyrrolo[2,1-f][1,2,4]triazine-6-carboxylic Acid Methyl Ester The title compound was prepared from Example 27 (20 mg, 0.09 mmol) and [3-(aminosulfonyl)-4-methylphenyl]amine (14 mg, 0.13 mmol) by the procedure analogous to Example 31. MS: [M+H]$^+$=376.2; $^1$H NMR (CDCl$_3$): δ 8.05 (s, 1H), 7.91 (s, 1H), 6.97 (d, J=7.8 Hz, 1H), 6.31 (s, 1H), 6.23 (d, J=7.8 Hz, 1H), 4.22 (t, J=7.7 Hz, 2H), 3.84 (s, 3H), 2.84 (t, J=7.7 Hz, 2H), 2.55 (s, 3H).

Example 64

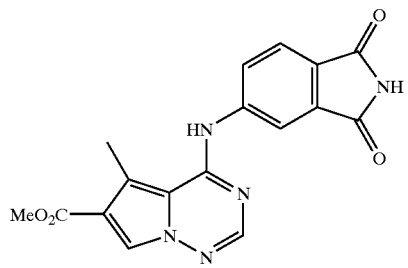

4-[(2,3-Dihydro-1,3-dioxo-1H-isoindol-5-yl)amino]-5-methylpyrrolo[2,1-f][1,2,4]triazine-6-carboxylic Acid Methyl Ester The title compound was prepared from Example 27 (20 mg, 0.09 mmol) and (2,3-dihydro-1,3-dioxo-1H-isoindol-5-yl)amine (16 mg, 0.1 mmol) by the procedure analogous to Example 31. MS: [M+H]$^+$=352.1; $^1$H NMR (CDCl$_3$): δ 8.38 (s, 1H), 8.18-8.04 (m, 3H), 7.94 (d, J=7.4 Hz, 1H), 3.88 (s, 3H), 2.84 (s, 3H).

Example 65

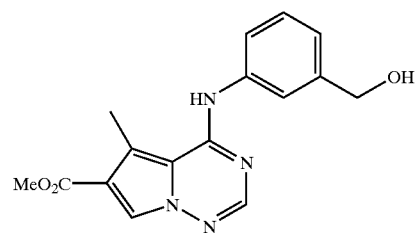

4-[[3-(Hydroxymethyl)phenyl]amino]-5-methylpyrrolo[2,1-f][1,2,4]triazine-6-carboxylic Acid Methyl Ester The title compound was prepared from Example 27 (18 mg, 0.08 mmol) and [3-(hydroxymethyl)phenyl]amine (12 mg, 0.1 mmol) by the procedure analogous to Example 31. MS: [M+H]$^+$=313.1; $^1$H NMR (CDCl$_3$): δ 7.91 (s, 1H), 7.86 (s, 1H), 7.61 (s, 1H), 7.53 (d, J=7.9 Hz, 1H), 7.32 (t, J=7.9 Hz, 1H), 7.10 (d, J=7.9 Hz, 1H), 4.67 (s, 2H), 3.81 (s, 3H), 2.88 (s, 3H).

Example 66

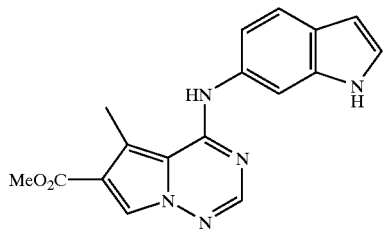

4-(1H-Indol-6-ylamino)-5-methylpyrrolo[2,1-f][1,2,4]triazine-6-carboxylic Acid Methyl Ester The title compound was prepared from Example 27 (18 mg, 0.08 mmol) and 1H-indol-6-ylamine (13 mg, 0.1 mmol) by the procedure analogous to Example 31. MS: [M+H]$^+$=322.1; $^1$H NMR (CD$_3$OD): δ 8.00 (s, 1H), 7.76 (d, J=3.0 Hz, 2H), 7.74 (s, 1H), 7.59 (d, J=8.4 Hz, 2H), 7.29 (d, J=3.0 Hz, 1H), 6.48 (d, J=8.4 Hz, 1H), 3.83 (s, 3H), 2.72 (s, 3H).

Example 67

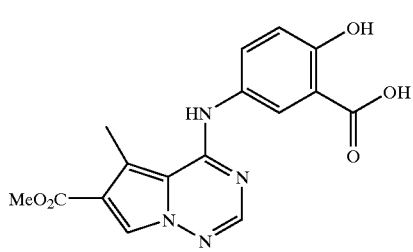

4-[(3-Carboxy-4-hydroxyphenyl)amino]-5-methylpyrrolo[2,1-f][1,2,4]triazine-6-carboxylic Acid Methyl Ester The title compound was prepared from Example 27 (22 mg, 0.1 mmol), 5-aminosalicylic acid (23 mg, 0.15 mmol) and 1 drop of triethylamine by the procedure analogous to Example 31. MS: [M+H]$^+$=343.1; $^1$H NMR (d-DMSO): δ 8.80 (s, 1H), 8.10-8.03 (m, 3H), 7.90 (s, 1H), 7.75 (m, 2H), 6.90 (d, J=8.9 Hz, 1H), 3.79 (s, 3H), 2.82 (s, 3H).

Example 68

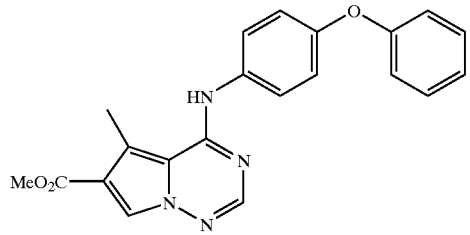

5-Methyl-4-[(4-phenoxyphenyl)amino]pyrrolo[2,1-f][1,2,4]triazine-6-carboxylic Acid Methyl Ester The title compound was prepared from Example 27 (22 mg, 0.1 mmol) and 5-aminosalicylic acid (28 mg, 0.15 mmol) by the procedure analogous to Example 31. MS: [M+H]$^+$=322.1; $^1$H NMR (CDCl$_3$): δ 7.92 (s, 1H), 7.86 (s, 2H), 7.53 (d, J=8.4 Hz, 2H), 7.31-7.26 (m, 3H), 7.19-6.95 (m, 5H), 3.82 (s, 3H), 2.85 (s, 3H).

Example 69

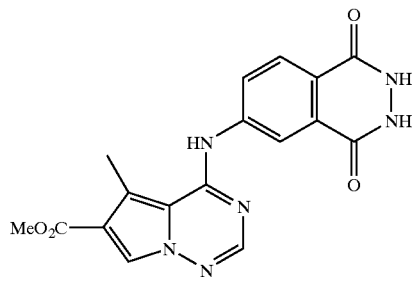

5-Methyl-4-[(1,2,3,4-tetrahydro-1,4-dioxo-6-phthalazinyl)amino]pyrrolo[2,1-f] [1,2,4]triazine-6-carboxylic Acid Methyl Ester The title compound was prepared from Example 27 (22 mg, 0.1 mmol) and (1,2,3,4-tetrahydro-1,4-dioxo-6-phthalazinyl)amine (27 mg, 0.15 mmol) by the procedure analogous to Example 31. MS: (M−H)$^-$=365$^-$

Example 70

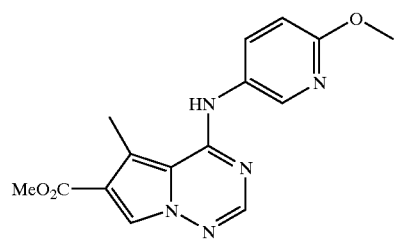

4-[(6-Methoxy-3-pyridinyl)amino]-5-methylpyrrolo[2,1-f][1,2,4]triazine-6-carboxylic Acid Methyl Ester The title compound was prepared from Example 27 (22 mg, 0.1 mmol) and (1,2,3,4-tetrahydro-1,4-dioxo-6-phthalazinyl)amine (19 mg, 0.15 mmol) by the procedure analogous to Example 31. MS: [M+H]$^+$=342.2; $^1$H NMR (CDCl$_3$): δ 8.25 (s, 1H), 7.94 (s, 1H), 7.85 (dd, J=8.6, 2.6 Hz, 1H), 7.82 (s, 1H), 6.79 (d, J=8.9 Hz, 1H), 3.89 (s, 3H), 3.82 (s, 3H), 2.84 (s, 3H).

Example 71

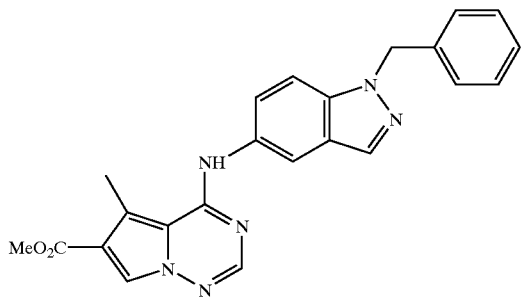

5-Methyl-4-[[1-(phenylmethyl)-1H-indazol-5-yl]amino]pyrrolo[2,1-f] [1,2,4]triazine-6-carboxylic Acid Methyl Ester The title compound was prepared from Example 27 (10 mg, 0.044 mmol) and [1-(phenylmethyl)-1H-indazol-5-yl]amine (20 mg) by the procedure analogous to Example 31 to provide 9.1 mg (50%) of solid. MS: [M+H]$^+$=413.2; $^1$H NMR (CDCl$_3$): δ 8.00 (m, 3H), 7.92 (s, 1H), 7.84 (s, 1H), 7.35-7.25 (m, 7H), 5.54 (s, 2H), 3.93 (s, 3H), 2.80 (s, 3H).

Example 72

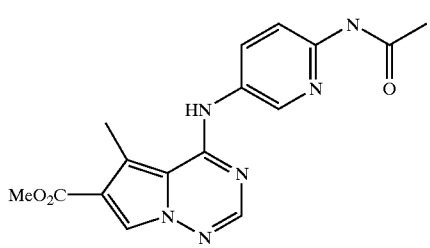

4-[[6-(Acetylamino)-3-pyridinyl]amino]-5-methylpyrrolo[2,1-f][1,2,4]triazine-6-carboxylic Acid Methyl Ester The title compound was prepared from Example 27 (10 mg, 0.044 mmol) and [6-(acetylamino)-3-pyridinyl]amine (14 mg, 0.09 mmol) by the procedure analogous to Example 31. MS: [M+H]$^+$=341.2; $^1$H NMR (d-DMSO): δ 10.51 (s, 1H), 8.87 (s, 1H), 8.53 (s, 1H), 8.14-8.01 (m, 3H), 7.93 (s, 1H), 3.80 (s, 3H), 2.83 (s, 3H), 2.32 (s, 3H).

Example 73

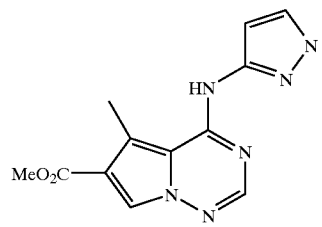

5-Methyl-4-(1H-pyrazol-3-ylamino)pyrrolo[2,1-f][1,2,4]triazine-6-carboxylic Acid Methyl Ester The title compound was prepared from Example 27 (10 mg, 0.044 mmol) and 1H-pyrazol-3-ylamine (7 mg, 0.09 mmol) by the procedure analogous to Example 31. MS: [M+H]$^+$=273.2; $^1$H NMR (CDCl$_3$): δ 7.94 (d, J=7.2 Hz, 2H), 7.77 (s, 1H), 7.69 (s, 1H), 6.45 (br s, 1H), 3.84 (s, 3H), 2.85 (s, 3H)

Example 74

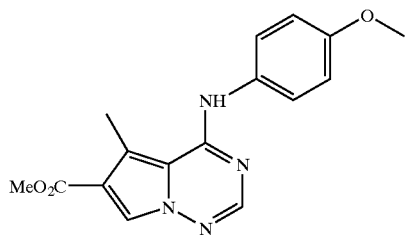

4-[(4-Methoxyphenyl)amino]-5-methylpyrrolo[2,1-f][1,2,4]triazine-6-carboxylic Acid Methyl Ester The title compound was prepared from Example 27 (10 mg, 0.044 mmol) and 4-methoxyaniline (11 mg, 0.09 mmol) by the procedure analogous to Example 31. MS: [M+H]$^+$=313.2; $^1$H NMR (CDCl$_3$): δ 7.91 (s, 1H), 7.83 (s, 1H), 7.44 (d, J=6.9 Hz, 2H), 6.89 (d, J=7.6 Hz, 2H), 3.81 (s, 3H), 3.76 (s, 3H)

Example 75

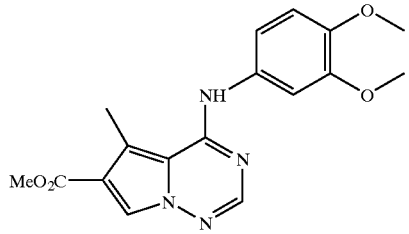

4-[(3,4-Dimethoxyphenyl)amino]-5-methylpyrrolo[2,1-f][1,2,4]triazine-6-carboxylic Acid Methyl Ester The title compound was prepared from Example 27 (10 mg, 0.044 mmol) and 3,4-dimethoxyaniline (14 mg, 0.09 mmol) by the procedure analogous to Example 31. MS: [M+H]$^+$=343.2; $^1$H NMR (CDCl$_3$): δ 7.91 (s, 1H), 7.85 (s, 1H), 7.21 (s, 1H), 7.00 (dd, J=8.6, 2.8 Hz, 1H), 6.82 (d, J=8.6 Hz, 1H), 3.84-3.82 (3s, 9H), 2.88 (s, 3H)

Example 76

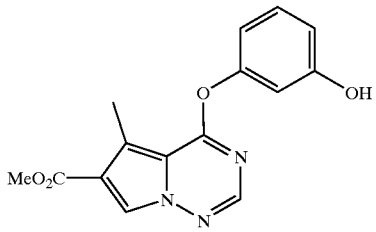

The title compound was prepared from Example 27 (23 mg, 0.10 mmol) and 1,3 dihydroxybenzene (117 mg, 0.15 mmol) by the procedure analogous to Example 32. MS: [M+H]$^+$=300; $^1$H NMR (CD$_3$OD): δ 8.38 (s, 1H), 7.92 (s, 2H), 7.28 (t, J=8.2 Hz, 1H), 6.78-6.70 (m, 2H), 3.86 (s, 3H), 2.82 (s, 3H).

Example 77

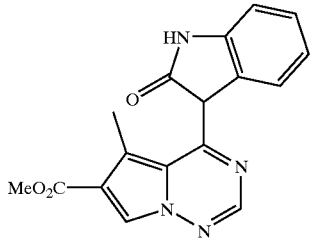

4-(2,3-Dihydro-2-oxo-1H-indol-3-yl)-5-methylpyrrolo[2,1-f][1,2,4]triazine-6-carboxylic Acid Methyl Ester The solution of oxindole (5.32 g, 40 mmol) in THF (150 ml) and DMF (35 ml) was deoxygenated by purging with argon. To this mixture in ice bath, sodium hydride (60% in oil, 1.7 g, 42 mmol) was added. After 30 min, Example 27 (3.38 g, 15 mmol) was added. After 1 hr. at rt, the resulting mixture was neutralized with acetic acid. The solvent was removed in vacuo. The residue was dissolved in dichloromethane, washed with brine, and dried (MgSO$_4$). The solution was concentrated to a solid residue which was triturated with dichloromethane and diethyl ether to afford the title compound as an orange solid (3.5 g, 72%). MS: [M+H]$^+$=323.1; $^1$H NMR (CDCl$_3$): δ 7.86 (s, 1H), 7.74 (s, 1H), 7.37 (s, 1H), 7.19 (d, J=7.6 Hz, 1H), 7.11 (t, J=7.6 Hz, 1H), 7.10 (t, J=7.6 Hz, 1H), 7.06 (d, J=7.6 Hz, 1H), 3.84 (s, 3H), 2.34 (s, 3H)

Example 78

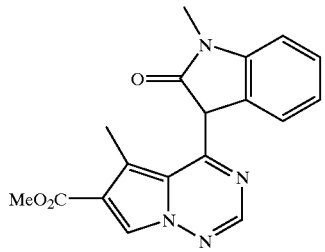

4-(2,3-Dihydro-1-methyl-2-oxo-1H-indol-3-yl)-5-methylpyrrolo[2,1-f][1,2,4]triazine-6-carboxylic Acid Methyl Ester The title compound was prepared as a yellow solid from Example 27 (22 mg, 0.10 mmol) and N-methyloxindole (22 mg, 0.15 mmol) by the procedure analogous to Example 32. MS: [M+H]$^+$=337.2; $^1$H NMR (CDCl$_3$): δ 7.90 (s, 1H), 7.40 (s, 1H), 7.16 (m, 2H), 7.02 (t, J=7.6 Hz, 1H), 6.90 (d, J=7.6 Hz, 1H), 5.28 (s, 1H), 3.86 (s, 3H), 3.36 (s, 3H), 2.37 (s, 3H).

Example 79

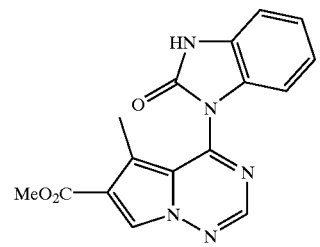

4-(2,3-Dihydro-2-oxo-1H-benzimidazol-1-yl)-5-methylpyrrolo[2,1-f] [1,2,4]triazine-6-carboxylic Acid Methyl Ester The title compound was prepared as a pale yellow solid (12 mg, 37%) from Example 27 (23 mg, 0.1 mmol) and 2,3-Dihydro-2-oxo-1H-benzimidazol (40.2 mg, 0.3 mmol). by the procedure analogous to Example 32. $^1$H NMR (CDCl$_3$): δ 8.37 (s, 1H), 8.32 (s, 1H), 7.95 (br, s, 1H), 7.21-7.10 (m, 4H), 3.88 (s, 3H), 2.51 (s, 3H).

Example 80

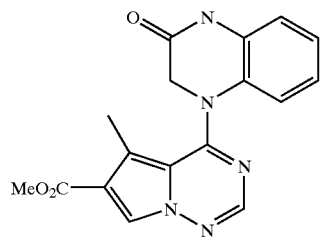

5-Methyl-4-(1,2,3,4-tetrahydro-3-oxo-1-quinoxalinyl)pyrrolo[2,1-f][1,2,4]triazine-6-carboxylic Acid Methyl Ester Example 27 (23 mg, 0.1 mmol) was stirred with 1,2,3,4-tetrahydroquinoxalin-2-one (44.4 mg, 0.3 mmol) in DMF (0.5 mL) for 1 hr at 50° C. Water was added and the resulting solid material was collected, washed with water and dried. The material was triturated with methanol, filtered, and dried again to provide 20 mg (59%) of a white solid. $^1$H NMR (d-DMSO): δ 8.30-8.25 (m, 2H), 7.12-7.03 (m, 2H), 6.83 (br s, 2H), 4.38 (s, 2H), 3.73 (s, 3H), 2.49 (s, 3H), 1.72 (s, 3H).

Example 81

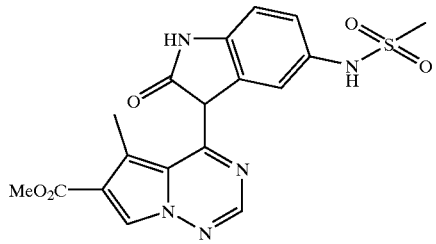

4-[2,3-Dihydro-5-[(methylsulfonyl)amino]-2-oxo-1H-indol-3-yl]-5-methylpyrrolo[2,1-f][1,2,4]triazine-6-carboxylic Acid Methyl Ester The title compound was prepared from Example 27 (24 mg, 0.1 mmol) and (methylsulfonyl)amino]-2-oxo-1H-indole (90 mg, 0.4 mmol) by the procedure analogous to Example 32. After purification directly by preparative HPLC, the desired material was collected, concentrated, and neutralized with aqueous NaHCO$_3$. The solid was collected and dried to provide a yellow solid (6 mg, 14%). $^1$H NMR (CD$_3$OD): δ 7.99 (s, 1H), 7.69 (s, 1H), 7.04-7.02 (m, 2H), 6.92 (d, J=8.8 Hz, 1H), 3.86 (s, 3H), 2.87 (s, 3H), 2.39 (s, 3H).

Example 82

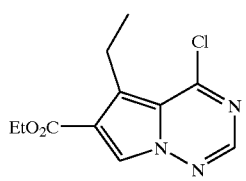

4-Chloro-5-ethyl pyrrolo[2,1-f][1,2,4]triazine-6-carboxylic Acid Ethyl Ester A. 4-Ethylpyrrole-3-carboxylic Acid Ethyl Ester Compound A was prepared from ethyl-trans-2-pentenoate by the procedure analogous to the preparation of Compound A of Example 18.

B. 5-Ethylpyrrolo[2,1-f][1,2,4]triazin-4(3H)-one-6-carboxylic Acid Ethyl Ester

Prepared from Compound A above by the procedure analogous to the preparation of Compound C of Example 19 from Compound A of Example 19.

C. 4-Chloro-5-ethylpyrrolo[2,1-f][1,2,4]triazine-6-carboxylic Acid Ethyl Ester

Prepared from Compound B by the procedure analogous to the preparation of Example 27. MS: (M+H)$^+$=254.6

Example 83

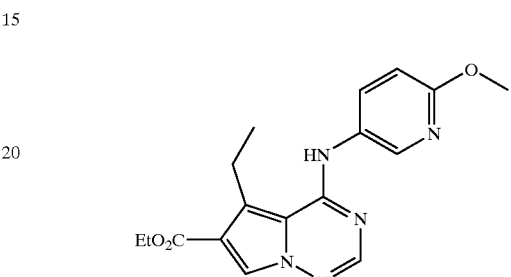

5-Ethyl-4-[(6-methoxy-3-pyridinyl)amino]pyrrolo[2,1-f][1,2,4]triazine-6-carboxylic Acid Ethyl Ester The title compound (369 mg, 88%) was obtained from Example 82 (290 mg, 1.23 mmol) and 5-amino-2-methoxy pyridine (229 mg, 1.85 mmol) by the procedure analogous to Example 31. MS: [M+H]$^+$=342.2; $^1$H NMR (CDCl$_3$): δ 8.26 (s, 1H), 7.97 (s, 1H), 7.87 (d, J=8.4 Hz, 1H), 7.82 (s, 1H), 6.80 (d, J=8.9 Hz, 1H), 4.28 (q, J= 7.1 Hz, 2H), 3.84 (s, 3H), 3.25 (q, J=7.6 Hz, 2H), 1.32 (s, 6H)

Example 84

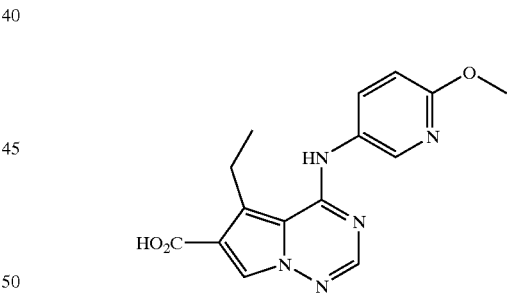

5-Ethyl-4-[(6-methoxy-3-pyridinyl)amino]pyrrolo[2,1-f][1,2,4]triazine-6-carboxylic Acid To a solution of Example 83 (7 mg, 0.02 mmol) in methanol (2 mL) was added 2.0 M aqueous sodium hydroxide (0.2 mL, 0.4 mmol). The reaction mixture was warmed to 70° C. and stirred for 3 hrs. The methanol was removed in vacuo and the residue was brought to pH 1 with 1 N aqueous HCl solution. The mixture was extracted with CH$_2$Cl$_2$. The combined organic extracts were dried (Na$_2$SO$_4$) and concentrated in vacuo to provide 4 mg (65%) of white solid. MS: [M+H]$^+$=314.1; $^1$H NMR (CDCl$_3$): δ 8.05 (s, 1H), 8.03 (s, 1H), 7.88 (m, 2H), 6.88 (d, J=8.7 Hz, 1H), 3.90 (s, 1H), 3.26 (q, J=7.2 Hz, 2H), 1.28 (t, J=7.2 Hz, 3H)

Example 85

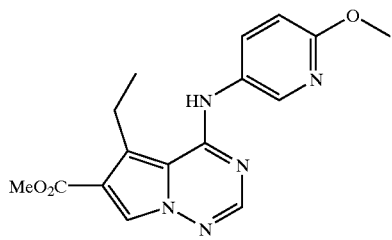

5-Ethyl-4-[(6-methoxy-3-pyridinyl)amino]pyrrolo[2,1-f][1,2,4]triazine-6-carboxylic Acid Methyl Ester To a solution of Example 84 (3 mg, 0.01 mmol) in methanol (0.3 mL) and toluene (0.7 mL) was added trimethylsilyl diazomethane (100 μL of 2.0 M solution in THF). After 30 min. acetic acid and methanol were added and the reaction mixture was concentrated in vacuo. The crude material was purified by chromatography on silica gel eluting with 20% ethyl acetate in hexanes to provide 3 mg of white solid. MS: [M+H]$^+$=328.1; $^1$H NMR (CDCl$_3$): δ 8.30 (s, 1H), 7.94-7.90 (m, 3H), 7.01 (s, 1H), –6.81 (d, J=8.8 Hz, 1H), 3.96 (s, 3H), 3.88 (s, 3H), 3.32 (q, J=7.6 Hz, 2H), 1.56 (t, J= 7.6 Hz, 3H).

Example 86

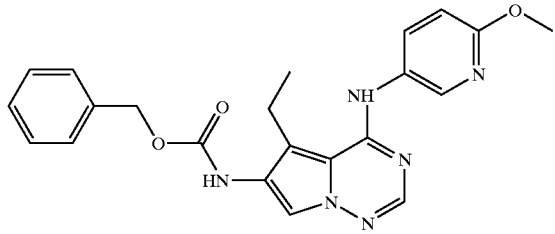

[4-[(6-Methoxy-3-pyridinyl)amino]-5-ethylpyrrolo[2,1-f][1,2,4]triazin-6-yl]carbamic Acid Phenylmethyl Ester To a suspension of Example 84 (36 mg, 0.12 mmol) in 1,4-dioxane (1.4 mL) under argon with powdered 4 Å molecular sieves was added triethylamine (19 μL, 0.14 mmol, 1.2 eq) and diphenylphosphoryl azide (30 μL, 0.14 mmol). The mixture was heated at 85° C. for 1 hr and then benzyl alcohol (24 μL, 0.23 mmol) was added. The reaction mixture was warmed at 85° C. for 15 hrs. The mixture was filtered, concentrated in vacuo, and purified directly by rotary chromatography directly on a 1 mm silica gel plate eluting with 2% methanol in chloroform to provide 29 mg (60%) of yellow oil. MS: [M+H]$^+$=419.2; $^1$H NMR (CDCl$_3$): δ 8.27 (d, J=2.7 Hz, 1H), 7.98 (s, 1H), 7.95 (dd, J=8.8, 2.7 Hz, 1H), 7.90 (s, 1H), 7.43-7.35 (m, 5H), 6.81 (d, J=8.8 Hz, 1H), 6.46 (br s, 1H), 5.24 (s, 2H), 3.96 (s, 3H), 2.82 (q, J=7.7 Hz, 2H), 1.34 (t, J=7.7 Hz, 3H).

Example 87

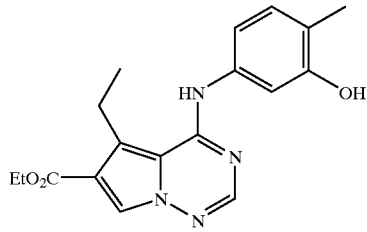

5-Ethyl-4-[(3-hydroxy-4-methylphenyl)amino]pyrrolo[2,1-f][1,2,4]triazine-6-carboxylic Acid Ethyl Ester The title compound was obtained as a solid from Example 82 (24 mg, 0.095 mmol) and 3-hydroxy-4-methylaniline (17 mg, 0.14 mmol) by the procedure analogous to Example 31. MS: [M+H]$^+$=339.1; $^1$H NMR (CDCl$_3$): δ 8.00 (s, 1H), 7.59 (s, 1H), 7.10 (s, 1H), 6.88 (d, J=8.4 Hz, 1H), 6.52 (d, J=8.4 Hz, 1H), 4.33 (q, J=7.6 Hz, 2H), 3.20 (m, 2H), 2.11 (s, 3H), 1.34 (t, J=7.6 Hz, 3H), 1.11 (t, J=7.4 Hz, 3H)

Example 88

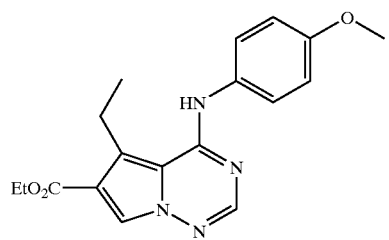

5-Ethyl-4-[(4-methoxyphenyl)amino]pyrrolo[2,1-f][1,2,4]triazine-6-carboxylic Acid Ethyl Ester The title compound was obtained as a solid from Example 82 (15 mg, 0.06 mmol) and 4-methoxy aniline (11 mg, 0.09 mmol) by the procedure analogous to example 31. MS: [M+H]$^+$=341.2; $^1$H NMR (CDCl$_3$): δ 8.02 (s, 1H), 7.81 (s, 1H), 7.32 (d, J=8.9 Hz, 1H), 6.91 (d, J=8.8 Hz, 1H), 4.30 (q, J=7.1 Hz, 2H), 3.77 (s, 3H), 3.11 (m, 2H), 1.33 (q, J=7.1 Hz, 3H), 1.26 (m, 3H).

Example 89

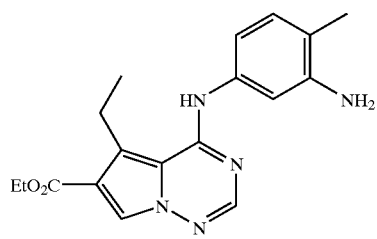

4-[(3-Amino-4-methylphenyl)amino]-5-ethylpyrrolo[2,1-f][1,2,4]triazine-6-carboxylic Acid Ethyl Ester The title compound was obtained as a solid from Example 82 (15 mg, 0.06 mmol) and 1,3-diamino-4-methyl benzene (19 mg, 0.09 mmol) by the procedure analogous to example 31. MS: [M+H]$^+$=340.2; $^1$H NMR (CDCl$_3$): δ 7.93 (br s, 2H), 7.91 (s, 1H), 7.13 (s, 1H), 7.00 (d, J=6.4 Hz, 1H), 6.76 (d, J=6.4 Hz, 1H), 4.30 (q, J=7.1 Hz, 2H), 3.20 (q, J=7.6 Hz, 2H), 2.18 (s, 3H), 1.32-1.23 (m, 6H)

Example 90

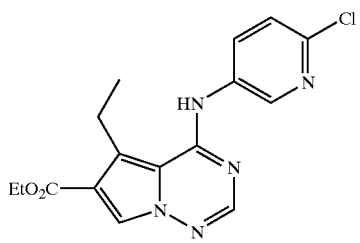

4-[(6-Chloro-3-pyridinyl)amino]-5-ethylpyrrolo[2,1-f][1,2,4]triazine-6-carboxylic Acid Ethyl Ester The title compound was obtained as a solid from Example 82 (10 mg, 0.044 mmol) and 5-amino-2-chloro-pyridine (12 mg, 0.088 mmol) by the procedure analogous to example 31. MS: ESI [M+H]$^+$=346.3; $^1$H NMR (CDCl$_3$): δ 8.47 (s, 1H), 8.25 (d, J=8.2 Hz, 1H), 7.98 (s, 1H), 7.90 (s, 1H), 7.31 (d, J=8.2 Hz, 1H), 4.28 (q, J=7.2 Hz, 2H), 3.28 (q, J=7.6 Hz, 2H), 1.31-1.15 (m, 6H).

Example 91

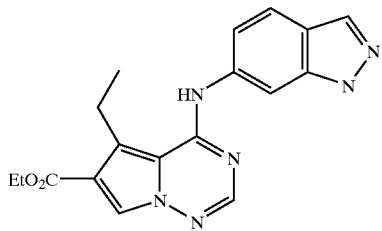

5-Ethyl-4-(1H-indazol-6-ylamino)pyrrolo[2,1-f][1,2,4]triazine-6-carboxylic Acid Ethyl Ester The title compound was obtained as a solid from Example 82 (10 mg, 0.044 mmol) and 6-aminoindazole (10 mg, 0.088 mmol) by the procedure analogous to example 31. MS: [M+H]$^+$=351.2; $^1$H NMR (CDCl$_3$): δ 8.39 (s, 1H), 7.97 (m, 3H), 7.68 (d, J=8.6 Hz, 1H), 7.46 (s, 1H), 6.98 (d, J=8.6 Hz, 1H), 4.29 (q, J=7.1 Hz, 2H), 3.30 (q, J=7.6 Hz, 2H), 1.34 (t, J=7.1 Hz, 3H), 1.31 (t, J=7.6 Hz, 3H)

Example 92

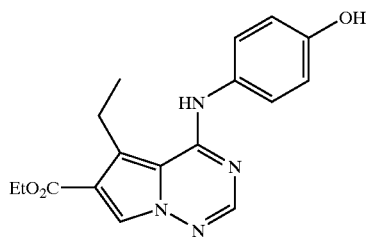

5-Ethyl-4-[(4-hydroxyphenyl)amino]pyrrolo[2,1-f][1,2,4]triazine-6-carboxylic Acid Ethyl Ester The title compound was obtained as a solid from Example 82 (10 mg, 0.04 mmol) and 4-aminophenol (9 mg, 0.08 mmol) by the procedure analogous to example 31. MS: [M+H]$^+$=327.2; $^1$H NMR (CDCl$_3$): δ 7.93 (s, 1H), 7.84 (s, 1H), 7.34 (m, 1H), 7.13 (s, 1H), 6.77 (m, 2H), 4.24 (q, J=7.2 Hz, 2H), 3.22 (q, J=7.6 Hz, 2H), 1.34-1.25 (m, 6H).

Example 93

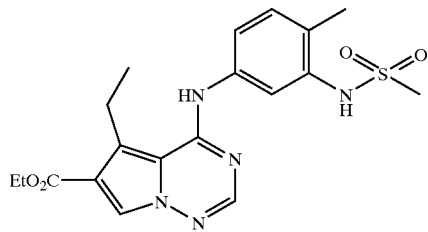

5-Ethyl-4-[[4-methyl-3-[(methylsulfonyl)amino]phenyl]amino]pyrrolo[2,1-f] [1,2,41-triazine-6-carboxylic Acid Ethyl Ester To a solution of Example 89 (12 mg, 0.035 mmol) in pyridine (0.35 mL) and CH$_2$Cl$_2$ (0.7 mL) at 0° C. was added methane sulfonyl chloride (4.8 mg, 0.04 mmol). The reaction mixture was warmed to 25° C. and stirred for 4 hrs. CH$_2$Cl$_2$ was added and the reaction mixture was washed with aqueous NaHCO$_3$ and dried (Na$_2$SO$_4$). The crude material was purified by chromatography on silica gel eluting with a gradient of 30–50% ethyl acetate in hexanes to provide a solid. MS: [M+H]$^+$=318.2; $^1$H NMR (CDCl$_3$): δ 8.03 (s, 1H), 7.96 (s, 1H), 7.91 (d, J=2.8 Hz, 1H), 7.38 (d, J=8.1 Hz, 1H), 7.28 (dd, J=8.0, 2.8 Hz, 1H), 6.35 (s, 1H), 4.31 (q, J=7.4 Hz, 3H), 3.38 (q, J=7.6 Hz, 2H), 3.21 (s, 3H), 2.38 (s, 3H), 1.40 (m, 6H).

Example 94

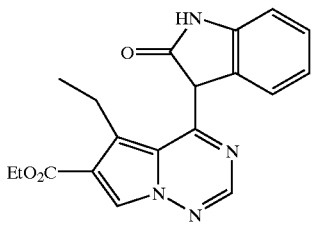

4-(2,3-Dihydro-2-oxo-1H-indol-3-yl)-5-ethylpyrrolo[2,1-f][1,2,4]triazine-6-carboxylic Acid Ethyl Ester The title compound was obtained as a yellow solid from Example 82 (24 mg, 0.1 mmol) was reacted with oxindole (17 mg, 0.14 mmol) by the procedure analogous to the procedure F of Example 77. MS: [M+H]$^+$=351.2; $^1$H NMR (CDCl$_3$): δ 9.05 (s, 1H), 8.21 (s, 1H), 8.07 (s, 1H), 7.53 (d, J=8.6 Hz, 1H), 7.28 (m, 2H), 4.39 (q, J=7.6 Hz, 2H), 2.81 (m, 2H), 1.45 (t, J=7.6 Hz, 3H), 1.00 (t, J=7.5 Hz, 3H).

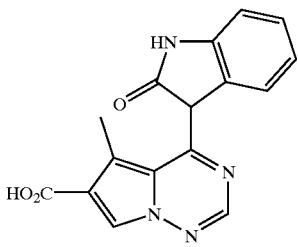

4-(2,3-Dihydro-2-oxo-1H-indol-3-yl)-5-methylpyrrolo[2,1-f][1,2,4]triazine-6-carboxylic Acid To a solution of Example 77 (3.3 g, 10.2 mmol) in methanol (600 mL) was added potassium hydroxide (1N aqueous solution, 200 mL) and the mixture was deoxygenated by purging with argon. The reaction mixture was heated to 60° C. for 20 hrs. The reaction mixture was cooled and concentrated to about 50 mL and the residue was acidified with concentrated HCl to pH 4. The yellow solid was collected, washed with water, and dried in vacuo to afford the title compound (2.9 g, 92%). MS: [M+H]$^+$ =307.1; $^1$H NMR (CD$_3$OD): δ 7.94 (s, 1H), 7.71 (s, 1H), 7.18-7.10 (m, 2H), 6.94-6.86 (m, 2H), 2.45 (s, 3H).

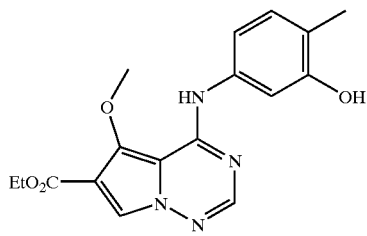

4-[(3-Hydroxy-4-methylphenyl)amino]-5-methoxy-pyrrolo[2,1-f][1,2,4]triazine-6-carboxylic Acid Ethyl Ester A. [[(2-Ethoxy-2-oxoethyl)(phenylmethyl)amino]methylene]propanedioic Acid Diethyl Ester N-benzylglycine ethyl ester (5.79 g, 30 mmol) was combined with diethyl ethoxymethylene malonate (6.48 g, 30 mmol) and stirred at 120° C. for 1 hr. The crude material was used directly for the next reaction.

B. 1-Phenylmethyl-3-hydroxypyrrole-2,4-dicarboxylic Acid Diethyl Ester

To a suspension of NaH (60% in oil, washed with hexanes, 500 mg, 12.5 mmol) in toluene (10 mL) was added Compound A (3.63 g, 10 mmol) in toluene (30 mL) dropwise at 50° C. After 2 hr. the mixture was poured into ice water, and acidified with 1 N aqueous HCl. The mixture was extracted three times with ethyl acetate and the combined organic extracts were dried (MgSO4) and concentrated in vacuo. The crude material was purified by chromatography on silica gel eluting with 50% ethyl acetate in hexanes to provide 2.70 g (85%) of Compound B as a pink oil.

C. 1-Phenylmethyl-3-methoxypyrrole-2,4-dicarboxylic Acid Diethyl Ester

Compound B (634 mg, 2 mmol) was stirred in acetone for 10 hrs at rt with methyl iodide (300 mg, 2.1 mmol) and potassium carbonate (500 mg). The mixture was filtered, concentrated, and purified by chromatography on silica gel eluting with 33% ethyl acetate in hexanes to provide 470 mg (71%) of Compound C as a gel.

D. 3-methoxypyrrole-2,4-dicarboxylic Acid Diethyl

Compound C (27 g, 81.5 mmol) in ethanol (1 L) was mixed with palladium on carbon (10%, 4 g) and ammonium formate (28 g) and hydrogenated at 40 psi at 90° C. for 18 hrs. The reaction mixture was cooled to rt, filtered, and concentrated. The crude material (brown oil) was purified by chromatography on silica gel eluting with 25% ethyl acetate in hexanes to provide 13 g (66%) of tan solid.

E. 1-Amino-3-methoxypyrrole-2,4-dicarboxylic Acid Diethyl Ester

To a stirred suspension of NaH (60% in oil, 1.76 g, 70 mmol) in DMF (350 mL) under nitrogen at 0° C. was added dropwise a solution of Compound D (13 g, 54 mmol) in DMF (200 mL). After 30 min. the mixture was diluted with DMF (750 mL) and diphenyl phosphoryl hydroxylamine (15.7 g, 67.4 mmol) was added one portion and the reaction mixture was allowed to warm to rt. After 6 hrs the mixture was concentrated and the residue was diluted with water (1 L), extracted with ethyl acetate (3×1 L). The combined organic extracts were dried (MgSO$_4$), concentrated and purified by chromatography on silica gel eluting with 20% ethyl acetate in hexanes to provide 13 g (93%) of solid.

F. 4-Hydroxy-5-methoxypyrrolo[2,1-f][1,2,4]triazine-6-carboxylic Acid Ethyl Ester Compound E (100 mg, 0.39 mmol) was combined with formamide (1 mL) and heated at 180° C. for 6 hrs. The reaction mixture was cooled to rt. And diluted with water (5 mL). The solid which formed was collected, washed with water, and dried to provide 70 mg (76%) of Compound F.

G. 4-Chloro-5-methoxypyrrolo[2,1-f][1,2,4]triazine-6-carboxylic Acid Ethyl Ester Phosphorous oxychloride (1 mL) was combined with Compound F (23.7 mg, 0.1 mmol) and heated at reflux for 2 hrs. The melt was allowed to cool to rt and phosphorous oxychloride was removed on rotary evaporator. The crude material was used directly for coupling reactions.

H. 4-[(3-Hydroxy-4-methylphenyl)amino]-5-methoxypyrrolo[2,1-f] [1,2,4]triazine-6-carboxylic Acid Ethyl Ester To a solution of Compound G (0.1 mmol, crude) in acetonitrile (2 mL) was added 5-amino-o-cresol (24.6 mg, 0.2 mmol) and the mixture was stirred for 1 hr. The resulting thick slurry was dissolved in methanol and purified by preparative HPLC. The desired fractions were collected, concentrated, and neutralized with aqueous NaHCO$_3$. The resulting solid material was collected and dried to provide 11.0 mg (32%) of the title compound. MS: [M+H]$^+$=343; $^1$H NMR (CD$_3$OD): δ 7.84 (s, 1H), 7.81 (s, 1H), 7.33 (s, 1H), 7.07 (d, J=8.0 Hz, 1H), 6.95 (d, J=8.0 Hz, 1H), 4.36 (q, J=7.0 Hz, 2H), 4.13 (s, 3H), 2.18 (s, 3H), 1.38 (t, J=7.0 Hz, 3H).

Example 97

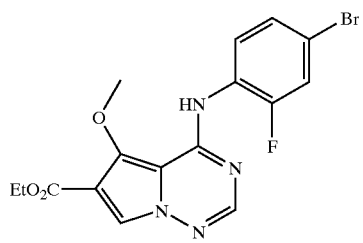

4-[(4-Bromo-2-fluorophenyl)amino]-5-methoxypyrrolo[2,1-f][1,2,4]triazine-6-carboxylic Acid Ethyl Ester The title compound was prepared from Compound G of Example 96 (0.2 mmol) and 4-bromo-2-fluoro-aniline (76 mg, 0.3 mmol) by the procedure analogous with the preparation of Compound H of Example 96. Thus, when the reaction was complete it was concentrated and washed with 1 N aqueous HCl to provide a solid which was triturated with aqueous NaHCO$_3$ and water and then dried to provide 58 mg (70.9%) white solid. MS: [M+H]$^+$=409,411 (1:1); $^1$H NMR (d-DMSO): δ 8.83 (s, 1H), 7.97-7.93 (m, 2H), 7.90 (s, 1H), 7.66 (d, J=8.4 Hz, 1H), 7.43 (d, J=8.4 Hz, 1H), 4.24 (q, J=7.5 Hz, 2H), 3.97 (s, 3H), 1.26 (t, J=7.0 Hz, 3H).

Example 98

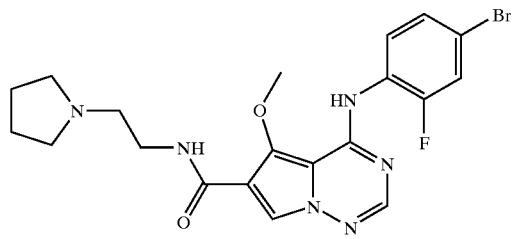

4-[(4-Bromo-2-fluorophenyl)amino]-5-methoxy-N-[2-(pyrrolidinyl)ethyl] pyrrolo[2,1-f][1,2,4]triazine-6-carboxamide

A. 4-[(4-Bromo-2-fluorophenyl)amino]-5-methoxy-N-[2-(pyrrolidinyl) ethyl]pyrrolo[2,1-f][1,2,4]triazine-6-carboxylic acid Example 97 (40.9 mg, 0.1 mmol) in methanol (2 mL) was stirred 72 hrs with 2 N aqueous NaOH (1 mL). The mixture was then heated at reflux for 2 hrs. The mixture was concentrated, acidified with 1 N aqueous HCl, and the resulting solid was washed with water and dried to provide 38 mg (100%) of solid.

B. 4-[(4-Bromo-2-fluorophenyl)amino]-5-methoxy-N-[2-(pyrrolidinyl)ethyl] pyrrolo[2,1-f][1,2,4]triazine-6-carboxamide To a solution of Compound A (14 mg, 0.037 mmol) in DMF (0.2 mL) at 25° C. was added 1-(2-aminoethyl)-pyrrolidine (10 mg, 0.088 mmol), 1-hydroxybenzotriazole (10 mg, 0.063 mmol) and 1-(3-dimethylaminopropyl)-3-ethylcarbodiimide hydrochloride (20 mg, 0.105 mmol). The reaction mixture was stirred 24 hrs. The crude material was purified by preparative HPLC, the product was collected and converted to its HCl salt and lyophilized to provide 9.5 mg (50%) of the title compound. MS: [M+H]$^+$=477, 479 (1:1); $^1$H NMR (CD$_3$OD): δ 8.33 (s, 1H), 7.86 (s, 1H), 7.73 (d, J=9.7 Hz, 1H), 7.65-7.57 (m, 2H), 4.18 (s, 3H), 3.84-3.78 (m, 4H), 3.48-3.45 (m, 2H), 3.19-3.13 (m, 2H), 2.21-2.05 (m, 4H).

Example 99

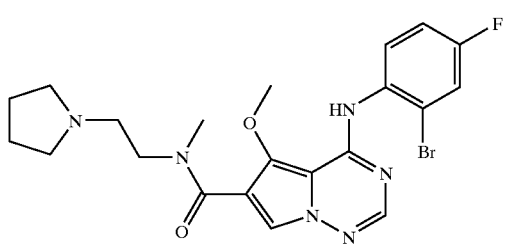

4-[(4-Bromo-2-fluorophenyl)amno]-5-methoxy-N-methyl-N-[2-(1-pyrrolidinyl)ethyl] pyrrolo[2,1-f][1,2,4]triazine-6-carboxamide To a solution of Compound A of Example 98 (20 mg, 0.052 mmol) in DMF (1 mL) was added 1-(2-methylaminoethyl)-pyrrolidine (10 mg, 0.078 mmol) and benzotriazol-1-yloxy-tris(dimethylamino)phosphonium hexafluorophosphate (25 mg, 0.056 mmol). After 1 hr at 25° C. the mixture was purified directly by preparative HPLC, the product was collected, converted to its HCl salt and lyophilized to provide 22 mg (80%) of the title compound. MS: [M+H]$^+$=491,493 (1:1); $^1$H NMR (CD$_3$OD): δ 8.27 (s, 1H), 7.83 (s, 1H), 7.73 (d, J=7.9 Hz, 1H), 7.65-7.55 (m, 2H), 4.09 (s, 3H), 3.99-3.96 (m, 4H), 3.85 (br s, 2H), 3.58-3.51 (m, 2H), 3.29-3.15 (m, 5H), 2.19-2.07 (m, 4H).

Example 100

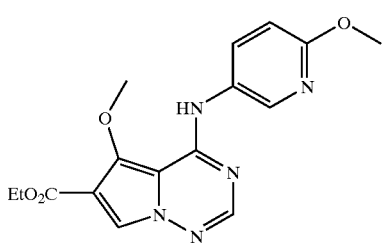

5-Methoxy-4-[(6-methoxy-3-pyridinyl)amino]pyrrolo[2,1-f][1,2,4]triazine-6-carboxylic Acid Ethyl Ester Compound G of Example 96 (0.1 mmol) and 5-amino-2-methoxypyridine (62 mg, 0.5 mmol) in CH$_3$CN (0.5 mL) was stirred for 2 hrs. The crude mixture was purified by preparative HPLC. The desired material was collected, concentrated, and neutralized with aqueous NaHCO$_3$. The solid was collected, washed with water, and dried to provide 12.5 mg (36%) of red solid. MS: [M+H]$^+$=344; $^1$H NMR (CDCl$_3$): δ 8.30 (s, 1H), 7.95 (d, J=8.8 Hz, 1H), 7.78 (d, J=7.9 Hz, 2H), 6.77 (d, J=8.8 Hz, 1H), 4.30 (q, J=7.0 Hz, 2H), 4.11 (s, 3H), 3.89 (s, 3H), 1.33 (t, J=7.0 Hz, 3H).

Example 101

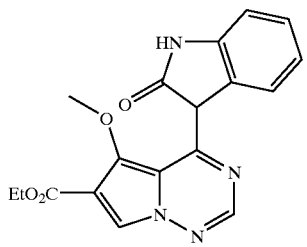

4-(2,3-Dihydro-2-oxo-1H-indol-3-yl)-5-methoxypyrrolo[2,1-f][1,2,4]triazine-6-carboxylic Acid Ethyl Ester To a suspension of NaH (60%, 44 mg, 1.1 mmol) in THF (1 mL) was added oxindole (133 mg, 1 mmol). The reaction mixture was stirred for 20 min. at rt. Compound G of example 96 (0.1 mmol) was added. The reaction was stirred for 2 hrs at 25° C. The crude material was purified by preparative HPLC followed by chromatography on silica gel eluting with ethyl acetate to provide 5.5 mg (16%) of a yellow solid. MS: [M+H]+=353; $^1$H NMR (CDCl$_3$): δ 8.42 (s, 0.4H), 8.10 (s, 0.6H), 7.79 (s, 1H), 7.75-6.88 (m, 4H), 4.33 (m, 2H), 3.57 (s, 3H), 1.37 (m, 3H).

Example 102

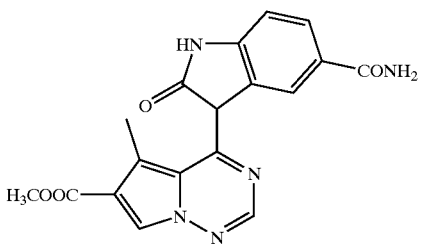

4-[5-(Aminocarbonyl)-2,3-dihydro-2-oxo-1H-indol-3-yl]-5-methylpyrrolo[2,1-f] [1,2,4]triazine-6-carboxylic Acid Methyl Ester The title compound was prepared from Example 27 (10 mg, 0.05 mmol) and 5-aminocarbonylindoline (23 mg, 0.14 mmol) by the procedure analogous to Example 73. MS: [M+H]$^+$=366.2; $^1$H NMR (CDCl$_3$/CD$_3$OH): δ 7.92 (s, 1H), 7.76 (s, 1H), 7.48 (d, J=8.0 Hz, 1H), 7.25 (s, 1H), 7.05 (d, J=8.0 Hz, 1H), 3.82 (s, 3H), 2.25 (s, 3H).

Example 103

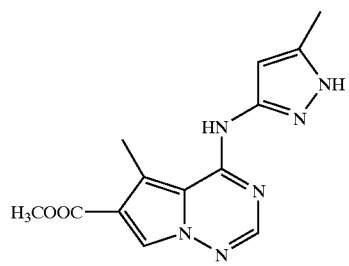

5-Methyl-4-[(5-methyl-1H-pyrazol-3-yl)amino]pyrrolo[2,1-f][1,2,4]triazine-6-carboxylic Acid Methyl Ester The title compound was prepared as a white solid (2.5 mg, 18%) from Example 27 (11 mg, 0.05 mmol) and 3-amino-5-methylpyrazole (7 mg, 0.07 mmol) by the procedure analogous to Example 31. MS: [M+H]$^+$=287.2; $^1$H NMR (CDCl$_3$ with 1 drop of CD$_3$OD): δ 7.92 (s, 1H), 7.89 (s, 1H), 6.59 (s, 1H), 3.81 (s, 3H), 2.84 (s, 3H), 2.13 (s, 3H).

Example 104

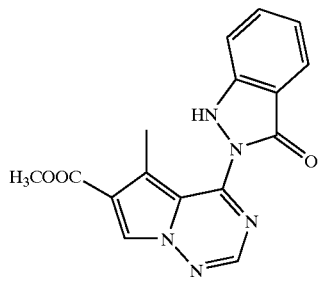

4-(2,3-Dihydro-3-oxo-1H-indazol-2-yl)-5-methylpyrrolo[2,1-f][1,2,4]triazine-6-carboxylic Acid Methyl Ester The title compound was prepared as a white solid (4.6 mg, 26%) from Example 27 (13 mg, 0.06 mmol) and 3-indazolinone (12 mg, 0.09 mmol) by the procedure analogous to Example 31. MS: [M+H]$^+$=324.2; $^1$H NMR (CDCl$_3$): δ 9.65 (s, 1H), 8.14 (s, 1H), 7.85 (s, 1H), 7.48 (d, J=8.2 Hz, 1H), 7.42-7.37 (m, 2H), 7.14-7.12 (m, 1H), 3.86 (s, 3H), 2.84 (s, 3H).

Example 105

4-(2,3-Dihydro-3-oxo-1H-indazol-1-yl)-5-methylpyrrolo[2,1-f][1,2,4]triazine-6-carboxylic Acid Methyl Ester The title compound was prepared as a white solid (4.1 mg, 20%) from Example 27 (16 mg, 0.07 mmol) and 3-indazolinone (14 mg, 0.11 mmol) by the procedure analogous to Example 77. [M+H]$^+$=324; $^1$H NMR (CDCl$_3$): δ 8.16 (s, 1H), 8.02-7.99 (m, 2H), 7.83-7.81 (m, 1H), 7.58-7.54 (m, 1H), 7.46 (s, 1H), 3.87 (s, 3H), 2.66 (s, 3H)

Example 106

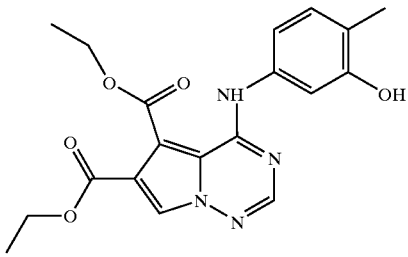

4-[(3-Hydroxy-4-methylphenyl)amino]pyrrolo[2,1-f][1,2,4]triazine-5,6-dicarboxylic Acid Diethyl Ester The title compound was made from pyrrolo-3,4-dicarboxylic acid diethyl ester in an analogous manner to that of the preparation of Example 13 from 2,4-dimethylpyrrole. MS: [M+H]$^+$=404.2; $^1$H NMR (CDCl$_3$): δ 8.03 (s, 1H), 7.69 (s, 1H), 7.47 (s, 1H), 7.08 (d, J=8.1 Hz, 1H), 7.06 (d, J=8.1 Hz, 1H), 4.34-4.28 (m, 4H), 2.17 (s, 3H), 1.32 (t, J=7.1 Hz, 6H).

Example 107

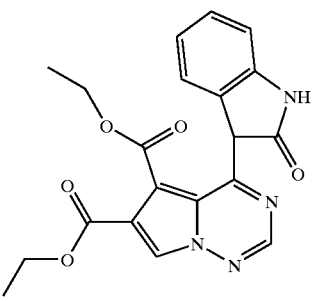

4-(2,3-Dihydro-2-oxo-1H-indol-3-yl)pyrrolo[2,1-f][1,2,4]triazine-5,6-dicarboxylic Acid Diethyl Ester The title compound was made from pyrrolo-3,4-dicarboxylic acid diethyl ester in an analogous manner to that of the preparation of Example 106 except the last step was carried out as described in Example 77 with a mixture of THF and DMF as the solvent. MS: [M+H]$^+$=395.2; $^1$H NMR (CD$_3$OD): δ 7.83 (s, 1H), 7.76 (s, 1H), 7.55 (d, J=8.5 Hz, 1H), 7.18-7.16 (m, 1H), 7.01-6.76 (m, 2H), 4.24 (q, J=7.1 Hz, 2H), 3.50 (q, J=7.2 Hz, 2H), 1.30 (t, J=7.1 Hz, 3H), 0.86 (t, J=7.2 Hz, 3H).

Example 108

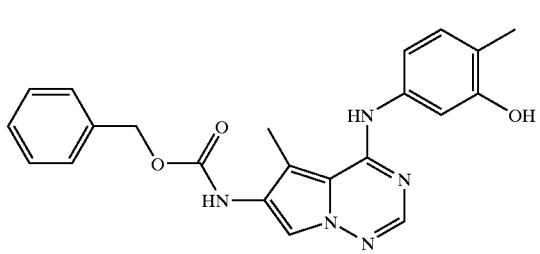

[4-[(3-Hydroxy-4-methylphenyl)amino]-5-methylpyrrolo[2,1-f][1,2,4]triazin-6-yl]carbamic Acid Phenylmethyl Ester A.
5-methylpyrrolo[2,1-f][1,2,4]triazin-6-yl]carbamic Acid Phenylmethyl Ester To a solution of Example 20 (11.5 mg, 60 μmol) in 1,4-dioxane (0.6 mL) under argon with powdered 4 Å molecular sieves was added triethylamine (10 μL, 71 μmol), diphenylphosphoryl azide (15 μL, 71 μmol) and benzyl alcohol (12 μL, 0.12 mmol). The reaction was warmed at 50° C. for 15 hrs. The mixture was concentrated in vacuo and chromatographed directly on silica gel eluting with a gradient of 2–5% methanol in chloroform to provide 8 mg (50%) of white solid. (M+H)$^+$=299.2

B. [4-[(3-Hydroxy-4-methylphenyl)amino]-5-methylpyrrolo[2,1-f][1,2,4]triazin-6-yl]carbamic Acid Phenylmethyl Ester Phosphorous oxybromide (5 eq.) was combined with Compound A (16 mg, 0.054 mmol) and heated to 60° C. for 20 min. The melt was poured into ice water and extracted with ethyl acetate (4×5 mL). The extracts were washed with aqueous NaHCO$_3$, dried (Na$_2$SO$_4$) and concentrated in vacuo. The residue was dissolved in a mixture of CH$_3$CN (0.5 mL) and DMF (0.1 mL) and 5-amino-o-cresol (10 mg, 0.081 mmol) was added. The reaction mixture was stirred overnight under argon at 25° C. Solvent was removed in vacuo, and the crude material was purified by rotary chromatography on a 1 mm silica gel plate eluting with 2% methanol in chloroform to provide 3.8 mg (20%) of white solid. MS: [M+H]$^+$=404.2; $^1$H NMR (CD$_3$OD): δ 7.79 (s, 1H), 7.70 (s, 1H), 7.44-7.31 (m, 5H), 7.16 (s, 1H), 7.05 (d, J=7.7 Hz, 1H), 6.87 (d, J=7.7 Hz, 1H), 5.19 (s, 2H), 2.48 (s, 3H), 2.16 (s, 3H).

Example 109

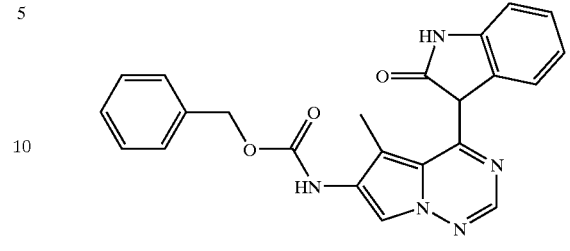

[4-(2,3-Dihydro-2-oxo-1H-indol-3-yl)-5-methylpyrrolo[2,1-f][1,2,4]triazin-6-yl]carbamic Acid Phenylmethyl Ester Example 95 (29 mg, 0.09 mmol) was converted to the title compound in an analogous manner to the preparation of Example 108 to afford the title compound as yellow oil (5 mg, 13%). MS: [M+H]+=414; $^1$H NMR (CDCl$_3$): δ 7.94 (s, 1H), 7.82 (s, 1H), 7.41-7.34 (m, 5H), 7.17-7.14 (m, 1H), 7.04-7.02 (m, 1H), 6.93-6.90 (m, 2H), 6.44 (s, 1H), 5.23 (s, 2H), 2.12 (s, 3H).

Example 110

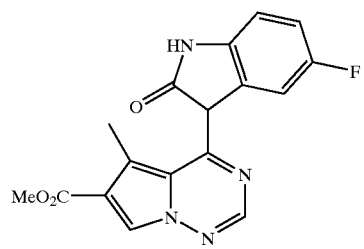

4-(5-Fluoro-2,3-dihydro-2-oxo-1H-indol-3-yl)-5-methylpyrrolo[2,11][1,2,4]triazine-6-carboxylic Acid Methyl Ester The title compound was prepared as a yellow solid (9 mg, 28%) from Example 27 (20 mg, 0.09 mmol) and 5-fluorooxindole (27 mg, 0.18 mmol) by the procedure analogous to that of Example 32. MS: [M+H]$^+$=341.2; $^1$H NMR (CDCl$_3$): δ 7.99 (s, 1H), 7.92 (br s, 1H), 7.48 (s, 1H), 6.87 (m, 3H), 3.91 (s, 3H), 2.44 (s, 3H).

Example 111

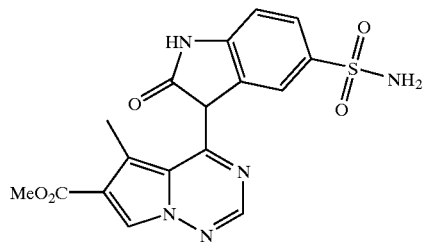

4-[5-(Aminosulfonyl)-2,3-dihydro-2-oxo-1H-indol-3-yl]-5-methylpyrrolo[2,1-f][1,2,4]triazine-6-carboxylic Acid Methyl Ester The title compound was prepared as a yellow solid (10 mg, 28%) from Example 27 (20 mg, 0.09 mmol) and 5-aminosulfonyloxindole (38 mg, 0.18 mmol) by the procedure analogous to Example 32. MS: [M−H]⁻=400.1; ¹H NMR (CD₃OD): δ 8.05 (s, 1H), 7.83 (s, 1H), 7.65 (d, J=8.2 Hz, 1H), 7.07 (d, J=8.3 Hz, 2H), 3.84 (s, 3H), 2.28 (s, 3H).

Example 112

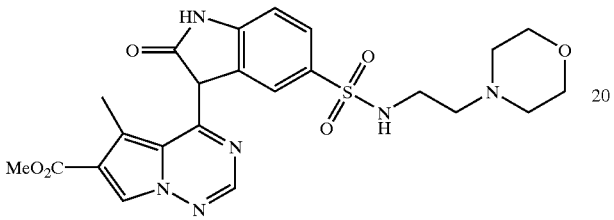

4-[2,3-Dihydro-5-[[[2-(4-morpholinyl)ethyl]amino]sulfonyl]-2-oxo-1H-indol-3-yl]-5-methylpyrrolo[2,1-f][1,2,4]triazine-6-carboxylic Acid Methyl Ester The title compound was prepared as a yellow solid (8 mg, 10%) from Example 27 (20 mg, 0.09 mmol) and 5-(2-morpholinylethylamino)sulfonyloxindole (59 mg, 0.18 mmol) by the procedure analogous to Example 32. MS: [M+H]⁺=515.2; ¹H NMR (CD₃OD): δ 8.07 (s, 1H), 7.79 (s, 1H), 7.62 (m, 2H), 7.14 (d, J=8.2 Hz, 1H), 4.20 (m, 2H), 3.84 (s, 3H), 3.80 (m, 2H), 3.30-3.12 (m, 8H), 2.30 (s, 3H).

Example 113

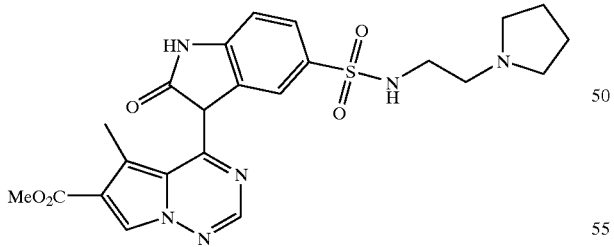

4-[2,3-Dihydro-2-oxo-5-[[[2-(1-pyrrolidinyl)ethyl]amino]sulfonyl]-1H-indol-3-yl]-5-methylpyrrolo[2,1-f][1,2,4]triazine-6-carboxylic Acid Methyl Ester The title compound was prepared as a yellow solid (12 mg, 52%) from Example 27 (10 mg, 0.05 mmol) and 5-(2-pyrrolidinylethylamino)sulfonyloxindole (27 mg, 0.09 mmol) by the procedure analogous to Example 32. MS: [M+H]⁺=499.2; ¹H NMR (CD₃OD): δ 8.06 (s, 1H), 7.79 (s, 1H), 7.64 (m, 2H), 7.14 (d, J=8.1 Hz, 1H), 3.86 (s, 3H), 3.74 (m, 2H), 3.33 (m, 4H), 3.30 (m, 2H), 2.40 (s, 3H), 2.17-2.24 (m, 4H).

Example 114

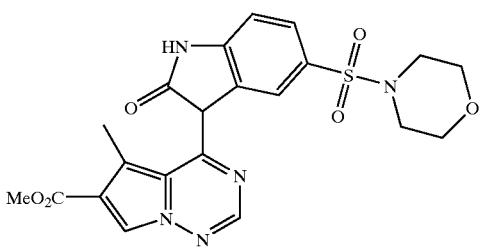

4-[2,3-Dihydro-5-(4-morpholinylsulfonyl)-2-oxo-1H-indol-3-yl]-5-methylpyrrolo[2,1-f][1,2,4]triazine-6-carboxylic Acid Methyl Ester The title compound was prepared as a yellow solid (10 mg, 47%) from Example 27 (10 mg, 0.05 mmol) and 5-morpholinylsulfonyloxindole (26 mg, 0.09 mmol) by the procedure analogous to Example 32. MS: [M+H]⁺=472.2; ¹H NMR (CD₃OD): δ 8.04 (s, 1H), 7.88 (m, 2H), 7.66 (d, J=7.8 Hz, 1H), 7.14 (d, J=7.9 Hz, 1H), 3.88 (s, 3H), 3.74-3.70 (m, 4H), 3.36-3.30 (m, 4H), 2.41 (s, 3H).

Example 115

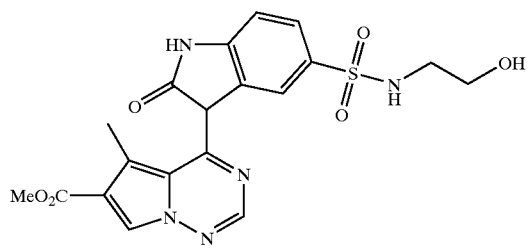

4-[2,3-Dihydro-5-[[(2-hydroxyethyl)amino]sulfonyl]-2-oxo-1H-indol-3-yl]-5-methylpyrrolo[2,1-f][1,2,4]triazine-6-carboxylic Acid Methyl Ester The title compound was prepared as a yellow solid (14 mg, 60% overall) from Example 27 (10 mg, 0.05 mmol) and 5-(2-tert-butyldimethylsilyloxy ethyl)sulfonyloxindole (34 mg, 0.1 mmol) by the procedure analogous to Example 32 followed by desilylation by tetrabutylammonium fluoride. MS: [M+H]⁺=446.2; ¹H NMR (CDCl₃/CD₃OH): δ 7.84 (s, 1H), 7.55 (s, 1H), 7.28 (d, J=8.6 Hz, 1H), 7.20 (s, 1H), 6.78 (d, J=8.6 Hz, 1H), 3.78 (s, 3H), 3.60 (t, J=7.4 Hz, 2H), 2.77 (t, J=7.4 Hz, 2H), 2.20 (s, 3H).

Example 116

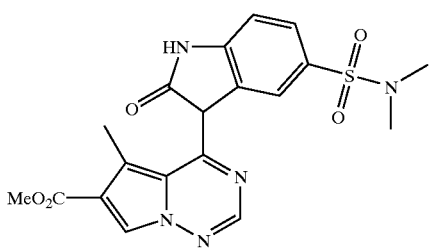

4-[5-[(Dimethylamino)sulfonyl]-2,3-dihydro-2-oxo-1H-indol-3-yl]-5-methylpyrrolo[2,1-f][1,2,4]triazine-6-carboxylic Acid Methyl Ester The title compound was prepared as a yellow solid (9 mg, 47%) from Example 27 (10 mg, 0.05 mmol) and 5-dimethylaminosulfonyl oxindole (22 mg, 0.09 mmol) by the procedure analogous to Example 32. MS: [M+H]$^+$=430. $^1$H NMR (CDCl$_3$): δ 9.56 (s, 1H), 8.05 (s, 1H), 7.65-7.54 (m, 3H), 7.15 (d, J=8.2 Hz, 1H), 3.87 (s, 3H), 2.73 (s, 6H), 2.43 (3H, s).

Example 117

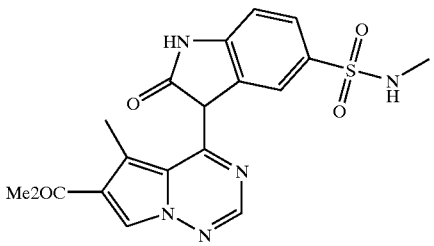

4-[2,3-Dihydro-5-[(methylamino)sulfonyl]-2-oxo-1H-indol-3-yl]-5-methylpyrrolo[2,1-f][1,2,4]triazine-6-carboxylic Acid Methyl Ester The title compound was prepared as a yellow solid (2 mg, 10%) from Example 27 (10 mg, 0.05 mmol) and 5-methylaminosulfonyl oxindole (22 mg, 0.09 mmol) by the procedure analogous to Example 32. MS: [M–H]$^-$=414. $^1$H NMR (CDCl$_3$/CD$_3$OH): δ 7.98 (s, 1H), 7.76 (s, 1H), 7.54 (s, 1H), 7.31 (d, J=7.6 Hz, 1H), 6.85 (d, J=7.6 Hz, 1H), 3.82 (s, 3H), 2.28 (s, 3H), 2.21 (s, 3H).

Example 118

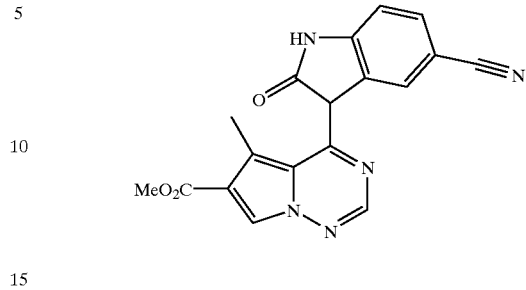

4-(5-Cyano-2,3-dihydro-2-oxo-1H-indol-3-yl)-5-methylpyrrolo[2,1-f] [1,2,4]triazine-6-carboxylic Acid Methyl Ester The title compound was prepared as a yellow solid (10 mg, 65%) from Example 27 (10 mg, 0.05 mmol) and 5-cyanooxindole (16 mg, 0.1 mmol) by the procedure analogous to Example 32. ESI [M+H]$^+$=348.2; $^1$H NMR (d-DMSO): δ 8.20 (s, 1H), 7.91 (s, 1H), 7.48 (d, J=8.1 Hz, 1H), 7.24 (s, 1H), 7.02 (d, J=8.1 Hz, 1H), 3.81 (s, 3H), 2.24 (s, 3H).

Example 119

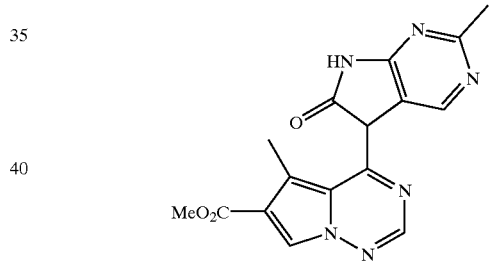

4-(2,3-Dihydro-6-methyl-2-oxo-1H-pyrazolo[2,3-d]pyrimidin-3-yl)-5-

A) 6-methyl-5,7-diazaoxindole

To a solution of ethyl (4-amino-2-methylpyrimidin-5-yl)acetate (WO 99/10349, 0.975 g, 5 mmol) in THF (30 ml), was slowly added potassium t-butoxide (1 M in THF, 5 mL). After one hour, the mixture was neutralized with acetic acid to pH 5. The volatiles were removed in vacuo and the residue was purified by flash column chromatography (silica gel, 5–8% MeOH in dichloromethane) to afford a yellow solid (680 mg, 91%).

B) Methylpyrrolo[2,1-f][1,2,4]triazine-6-carboxylic Acid Methyl Ester

To a solution of 6-methyl-5,7-diazaoxindole (67 mg, 0.45 mmol) in DMF (2 ml) and THF (1 ml) was added sodium hydride (60% in oil, 20 mg, 0.5 mmol). After stirring for 20 min, Example 27 (34 mg, 0.15 mmol) was added and the mixture was stirred at rt overnight. The mixture was neutralized with acetic acid. Dichloromethane (10 ml) was added to the mixture and the resulting precipitate was collected and washed with small amount of dichloromethane, water, and dried in vacuo to give orange solid (32 mg, 63%). MS: (M+H) 359

Example 120

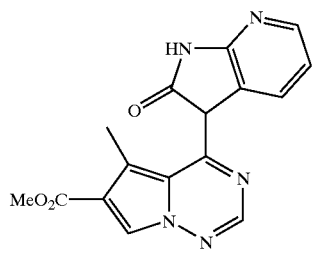

4-(2,3-Dihydro-2-oxo-1H-pyrazolo[2,3-b]pyridin-3-yl)-5-methylpyrrolo[2,1-f] [1,2,4]triazine-6-carboxylic Acid Methyl Ester To a solution of 7-azaoxindole (Tetrahedron.Lett. 1987, 28, 4027) (60 mg, 0.45 mmol) in DMF (2 mL) and THF (1 mL) was added sodium hydride (60% in oil, 20 mg, 0.5 mmol). After stirring for 20 min, Example 27 (34 mg, 0.15 mmol) was added and the mixture was stirred at rt overnight. The solution was neutralized with acetic acid and dichloromethane (10 ml) was added to the mixture. The resulting solid was collected, washed with small amount of dichloromethane and water, and dried in vacuo to give a yellow solid (35 mg, 72%). LC-MS: (M+H)$^+$=324.

Example 121

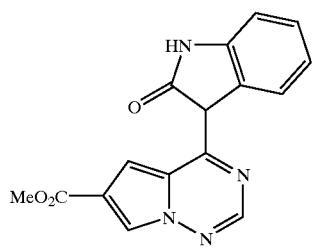

4-(2,3-Dihydro-2-oxo-1H-indol-3-yl)pyrrolo[2,1-f] [1,2,4]triazine-6-carboxylic acid methyl ester A)
4-Chloro-6-carbomethoxypyrrolo[2,1-f][1,2,4]triazine Prepared according to the procedure described for Example 27 except using 2-methoxycarbonyl pyrrole as the starting pyrrole.

B) 4-(2,3-Dihydro-2-oxo-1H-indol-3-yl)pyrrolo[2,1-f][1,2,4]triazine-6-carboxylic acid methyl ester Compound A was converted to the title compound using a procedure similar to that used for the preparation of Example 120.

Examples 122 to 125 were prepared by a procedure analogous to the preparation of Example 120 using appropriate reagents known in the literature (WO 97/42187).

Example 122

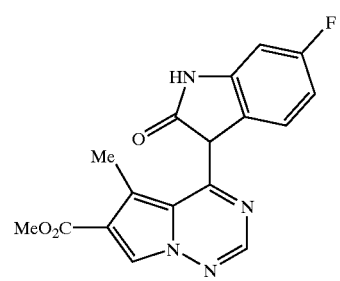

4-[6-Fluoro-2-hydroxy-1H-indol-3-yl]-5-methylpyrrolo[2,1-f][1,2,4]triazine-6-carboxylic Acid Methyl Ester Example 123

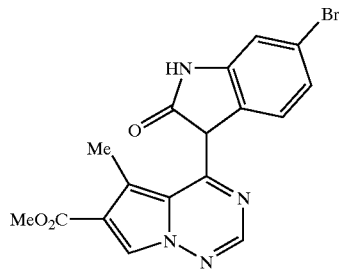

4-[6-Bromo-2-hydroxy-1H-indol-3-yl]-5-methylpyrrolo[2,1-f][1,2,4]triazine-6-carboxylic Acid Methyl Ester Example 124

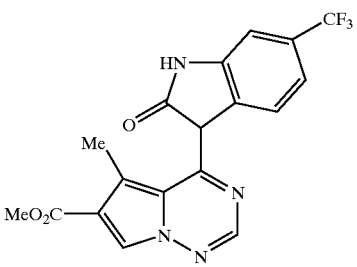

4-[2,3-Dihydro-2-oxo-6-(trifluoromethyl)-1H-indol-3-yl]-5-methylpyrrolo[2,1-f] [1,2,4]triazine-6-carboxylic Acid Methyl Ester Example 125

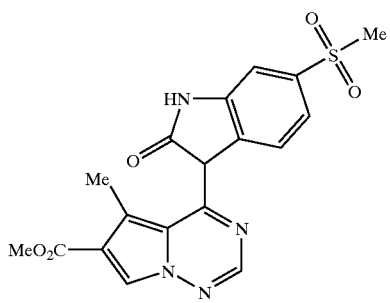

4-[2,3-Dihydro-6-(methylsulfonyl)-2-oxo-1H-indol-3-yl]-5-methylpyrrolo[2,1-f][1,2,4]triazine-6-carboxylic Acid Methyl Ester Example 126

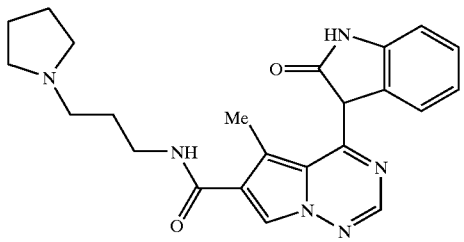

4-(2,3-Dihydro-2-oxo-1H-indol-3-yl)-5-methyl-N-[3-(1-pyrrolidinyl)propyl] pyrrolo[2,1-f][1,2,4]triazine-6-carboxamide To a solution of Example 95 (50 mg, 0.16 mmol) in DMF (1 mL), dichloromethane (0.5 mL) were added PyBrop (113 mg, 0.24 mmol) and diisopropylethyl amine (0.08 mL, 0.5 mL). After 10 min, 1-(3-aminopropyl)pyrrolidine (61 mg, 0.48 mmol) was added. After 15 h, the reaction mixture was purified by preparative RP HPLC. The yellow oil obtained was converted to the HCl salt and lyophilized to afford a red orange solid (25 mg, 34%). MS: $(M+H)^+=419$.

The compounds named in Example 127 were prepared from Example 95 and appropriate amines by using the procedure described for Example 126.

Example 127

4-(2,3-Dihydro-2-oxo-1H-indol-3-yl)-N,5-dimethyl-N-[2-(1 pyrrolidinyl)ethyl]pyrrolo[2, 1-f][1,2,4]triazine-6-carboxamide;
4-(2,3-Dihydro-2-oxo-1H-indol-3-yl)-5-methyl-N-[2-(1 pyrrolidinyl)ethyl]pyrrolo[2, 1-f][1,2,4]triazine-6-carboxamide;
4-(2,3-Dihydro-2-oxo-1H-indol-3-yl)-5-methyl-N-[3-(4-morpholinyl)propyl]pyrrolo[2, 1-f][1,2,4]triazine-6-carboxamide;
4-(2,3-Dihydro-2-oxo-1H-indol-3-yl)-5-methyl-N-[2-(4-morpholinyl)ethyl]pyrrolo[2,1-f][1,2,4]triazine-6-carboxamide;
4-(2,3-Dihydro-2-oxo-1H-indol-3-yl)-5-methyl-N-[3-(4-methyl-1-piperazinyl)propyl]pyrrolo[2,1-f][1,2,4]triazine-6-carboxamide;
4-(2,3-Dihydro-2-oxo-1H-indol-3-yl)-5-methyl-N-[3-(1H-1,2,3-triazol-1-yl)propyl]pyrrolo[2,1-f][1,2,4]triazine-6-carboxamide;
4-(2,3-Dihydro-2-oxo-1H-indol-3-yl)-5-methyl-N-[3-(2H-1,2,3-triazol-2-yl)propyl]pyrrolo[2, 1-f][1,2,4]triazine-6-carboxamide;
4-(2,3-Dihydro-2-oxo-1H-indol-3-yl)-5-methyl-N-[3-(1H-1,2,4-triazol-1-yl)propyl]pyrrolo[2, 1-f][1,2,4]triazine-6-carboxamide;
4-(2,3-Dihydro-2-oxo-1H-indol-3-yl)-5-methyl-N-[3-(2-methyl-1H-imidazol-1-yl)propyl]pyrrolo[2,1-f][1,2,4]triazine-6-carboxamide;
4-(2,3-Dihydro-2-oxo-1H-indol-3-yl)-5-methyl-N-[4-(4-morpholinyl)butyl]pyrrolo[2,1-f][1,2,4]triazine-6-carboxamide;
4-(2,3-Dihydro-2-oxo-1H-indol-3-yl)-N,5-dimethyl-N-[3-(4-morpholinyl)propyl]pyrrolo[2, 1-f][1,2,4]triazine-6-carboxamide;
4-(2,3-Dihydro-2-oxo-1H-indol-3-yl)-5-methylpyrrolo[2,1-f][1,2,4]triazine-61 carboxamide;
4-(2,3-Dihydro-2-oxo-1H-indol-3-yl)-N,5-dimethylpyrrolo[2,1-f][1,2,4]triazine-6-carboxamide;

Example 128

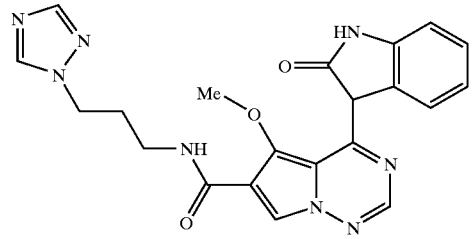

4-(2,3-Dihydro-2-oxo-1H-indol-3-yl)-5-methoxy-N-[3-(1H-1,2,4-triazol-1-yl)propyl] pyrrolo [2,1-f][1,2,4]triazine-6-carboxamide A) 4-(2,3-Dihydro-2-oxo-1H-indol-3-yl)-5-methoxy-pyrrolo[2,1-f] [1,2,4]triazine-6-carboxylic acid Example 101 was hydrolyzed by treatment with aqueous 1N KOH in methanol at 55° C. for 2 h. The reaction mixture was adjusted to pH=3 by addition of aqueous HCl. Partial concentration in vacuo precipitated a yellow solid which was filtered and triturated with water followed by ether to afford the acid (80% yield). MS: $(M+H)^+= 325$.

B) 4-(2,3-Dihydro-2-oxo-1H-indol-3-yl)-5-methoxy-N-[3-(1H-1,2,4-triazol-1-yl)propyl]pyrrolo[2,1-f][1,2,4]triazine-6-carboxamide Procedure same as that for Example 126 except N-[3-(1H-1,2,4-triazol-1-yl)propylamine was used. MS: $(M+H)^+=433$.

Example 129

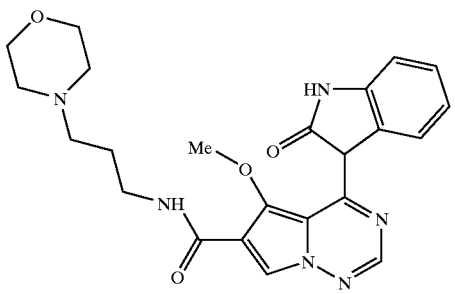

4-(2,3-Dihydro-2-oxo-1H-indol-3-yl)-5-methoxy-N-[3-(4-morpholinyl)propyl] pyrrolo[2,1-f][1,2,4]triazine-6-carboxamide Compound A of Example 128 was converted to the title compound by the procedure same as that for Example 126 except N-[3-(4-morpholinyl)propylamine was used. MS: (M+H)$^+$=451.

Example 130

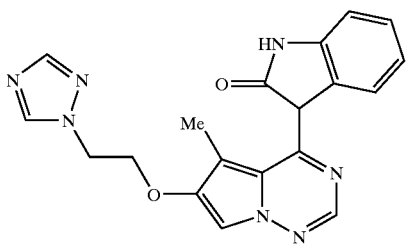

1,3-Dihydro-3-[5-methyl-6-[2-(1H-1,2,4-triazol-1-yl)ethoxy]pyrrolo[2,1-f] [1,2,4]triazin-4-yl]-2H-indol-2-one

A) 4-Phenoxy-5-methyl-6-carbomethoxypyrrolo[2,1-f][1,2,4]triazine

To a solution of phenol (705 mg, 7.5 mmol) in a mixture of THF (10 mL) and DMF (10 mL), was added NaH (60% in oil, 300 mg, 7.5 mmol). After 30 min, Example 27 (675 mg, 3.0 mmol) was added. After 1 h, the solvent was removed and the residue was poured into 5% aqueous K$_2$CO$_3$ solution. The precipitate was collected, washed with water, and dried in vacuo to afford Compound A as white solid (800 mg, 94%). MS: (M+H)$^+$=284

B) 4-Phenoxy-5-methyl-6-hydroxymethylpyrrolo[2,1-f][1,2,4]triazine

To a solution of Compound A (700 mg, 2.47 mmol) in toluene (20 mL) at −60° C., was added DIBAL (1.5 M in toluene, 6 mmol). After stirring at 0° C. for 1 h, aqueous 1N HCl (30 mL) was added and the mixture was stirred for 30 min. The mixture was then diluted with dichloromethane (DCM). The organic layer was separated, dried (MgSO$_4$) and concentrated. The residue was purified by flash column chromatography (silica gel, 2% MeOH in DCM) to afford Compound B as a solid (610 mg, 96%). MS: (M+H)$^+$=256

C) 4-Phenoxy-5-methylpyrrolo[2,1-f][1,2,4]triazine-6-carboxaldehyde

A mixture of Compound B (500 mg, 1.96 mmol) and MnO$_2$ (3.0 g) in toluene (30 mL) was heated at 60° C. for 1 h. After cooling to rt, the mixture was filtered through a pad of silica gel and washed with ethyl acetate. After concentration in vacuo, Compound C was obtained as a white solid (420 mg, 85%). MS: (M+H)$^+$=254

D) 4-Phenoxy-5-methyl-6-hydroxypyrrolo[2,1-f][1,2,4]triazine

A mixture of Compound C (708 mg, 2.8 mmol) and m-CPBA (55–85% pure, 800 mg) in dichloroethane (50 mL) was stirred at rt for 15 hrs. Another portion of m-CPBA (250 mg) was added. After 4 h, the mixture was diluted with DCM and washed with aqueous NaHCO$_3$ solution. The organic layer was concentrated and the residue was diluted with MeOH and stirred with K$_2$CO$_3$ (250 mg) for 1 h. The mixture was concentrated and the residue was diluted with DCM, washed with 2% aqueous citric acid, dried (MgSO$_4$). The product was purified by flash column chromatography (4% MeOH in DCM) to afford Compound D (245 mg, 36%) as white solid and Compound C (300 mg, 42%) was recovered. MS: (M+H)$^+$=242

E) 4-Phenoxy-5-methyl-6-[2-(1H-1,2,4-triazol-1-yl)ethoxy]pyrrolo[2,1-f] [1,2,4]triazine The solution of Compound D (40 mg, 0.16 mmol) in a mixture of DMF (2 mL) and THF (1 mL) was treated with NaH (60% in oil, 0.18 mmol). After 20 min, 2-(1H-1,2,-triazol-1-yl)ethyl mesylate (80 mg, 0.27 mmol) was added. The mixture was stirred at rt for 1 h, and at 80° C. for 2 hr. The mixture was then cooled, diluted with DCM, washed with aqueous NaH$_2$PO$_4$ solution, dried (MgSO$_4$) and concentrated. The residue was purified by flash column chromatography (silica gel, 100% DCM to 5% MeOH in DCM) to yield Compound E (17 mg, 32%) as white solid. MS: (M+H)$^+$=337

F) 5-Methyl-6-[2-(1H-1,2,4-triazol-1-yl)ethoxy]pyrrolo[2,1-f] [1,2,4]triazin-4(3H)-one A mixture of Compound E (15 mg, 0.045 mmol) in ethanol (10 mL) and HCl (1N, 5 mL) was heated at 80° C. in a sealed tube for 4 h. The mixture was cooled and the volatiles were removed in vacuo. The residue was purified by flash column chromatography (5% MeOH in DCM) to give a white solid (10 mg, 86%). MS: (M+H)$^+$=261.

G) 4-Chloro-5-methyl-6-[2-(1H-1,2,4-triazol-1-yl)ethoxy]pyrrolo[2,1-f] [1,2,4]triazine A mixture of Compound F (10 mg, 0.04 mmol) and POCl$_3$ and DIPEA (8 mL) was heated at 90° C. in a sealed tube for 1 h. The volatiles were removed in vacuo. The residue was diluted with DCM, washed with ice-cold aqueous NaHCO$_3$ solution, dried (MgSO$_4$) and concentrated. After removal of solvent, Compound G was obtained as a yellow solid 10 (10 mg, 100%). It was used without further purification.

H) 1,3-Dihydro-3-[5-methyl-6-[2-(1H-1,2,4-triazol-lyl)ethoxy] pyrrolo[2,1-f][1,2,4]triazin-4-yl]-2H-indol-2-one A solution of oxindole (65 mg, 0.5 mmol) in DMF (2 mL) was purged with argon. NaH (60% in oil, 20 mg, 0.5 mmol) followed by Compound G (10 mg, 0.04 mmol) were added to the reaction mixture. After 2 h, acetic acid (50 mL) was added to quench the reaction. The volatiles were removed in vacuo and the residue was purified by flash column chromatography (silica gel, 5% MeOH in DCM) to give the title compound as an orange solid (6 mg, 42%). MS: (M+H)$^+$=376.

Example 131

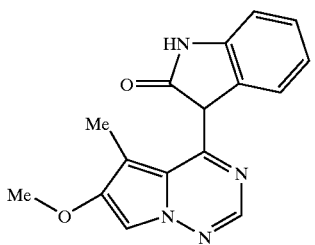

Procedure described for Example 130 was used except in Step E, iodomethane was used and the reaction mixture was stirred at rt. MS: (M+H)$^+$=295.

Example 132

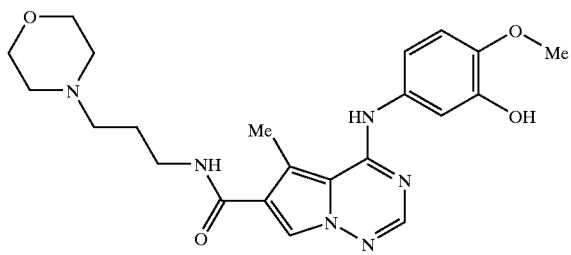

4-(3-Hydroxy-4-methoxyphenyl)-5-methyl-N-[3-(4-morpholinyl)propyl] pyrrolo[2,1-][1,2,4]triazine-6-carboxamide A) 5-Methylpyrrolo[2,1-f][2,4]triazin-4(3H)-one-6-carboxylic Acid To a solution of the Compound C of Example 19 (1.035 g, 5.00 mmol) in a mixture of tetrahydrofuran/methanol/water (50 mL, 3:1:1) was added lithium hydroxide (2.062 g, 49.1 mmol). The reaction mixture was stirred at 55° C. for 12 h, then cooled to 0° C. and neutralized by 3N HCl. The organic solvents were removed and the aqueous solution brought to pH 4 with 1 N HCl. The resulting precipitate was filtered, rinsed with cold water and air dried to afford the Compound A as an off-white solid (0.965 g, 100%).

B) 4-Chloro-5-methyl-N-[3-(4-morpholinyl)propyl] pyrrolo[2,1-f] [1,2,4]triazine-6-carboxamide A suspension of Compound A (2.00 g, 10.4 mmol) in phosphorous oxychloride (8 mL) was stirred at 100° C. over 4 h. The solvent was removed in vacuo using toluene to assist in the removal. The resulting green solid was suspended in acetonitrile (20 mL) at 0° C. and treated with sufficient triethylamine (5 mL) to bring the solution to pH 10. 4-(3-aminopropyl)morpholine (1.5 mL, 10.3 mmol) was added and the solution was allowed to stir at ambient temperature over 1 h. The reaction mixture was poured into saturated sodium bicarbonate solution and extracted with ethyl acetate. The organic layer was dried (MgSO$_4$) and the volatiles were removed in vacuo to afford Compound B as a yellow solid (1.75 g, 50%). It was used without further purification.

C) 4-(3-Hydroxy-4-methoxyphenyl)-5-methyl-N-[3-(4-morpholinyl)propyl] pyrrolo[2,1-f][1,2,4]triazine-6-carboxamide To a solution of Compound B (25.5 mg, 0.075 mmol) in DMF (1 mL) was added 5-amino-2-methoxyphenol (21 mg, 0.15 mmol). After 4 h at rt the volatiles were removed in vacuo. Chromatography on silica gel eluting with a gradient of 2 to 10% methanol in dichloromethane yielded a white solid. This material was suspended in acetonitrile (1 mL) and dichloromethane (1 mL) and treated with 1 N hydrogen chloride in diethyl ether to afford the HCl salt of the title compound as a grey solid (21 mg, 58%). MS: (M+H)$^+$=441.

Example 133

The following two compounds were prepared by treatment of compound B of Example 132 and appropriate amine using the procedure described for the synthesis of Example 132.
4-[(3-Hydroxy-4-methylphenyl)amino]-5-methyl-N-[3-(4-morpholinyl)propyl]pyrrolo[2, 1-f][1,2,4]triazine-6-carboxamide;
4-[(4-Bromophenyl)amino]-5-methyl-N-[3-(4-morpholinyl)propyl]pyrrolo[2, 1 f][ 1,2,4]triazine-6-carboxamide.

Example 134

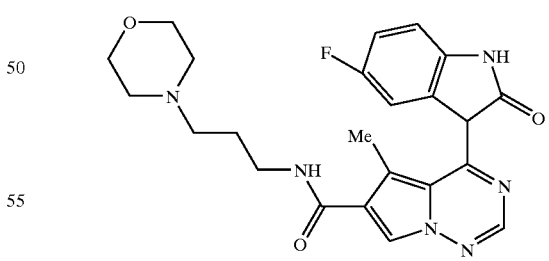

4-(5-Fluoro-2,3-dihydro-2-oxo-1H-indol-3-yl)-5-methyl-N-[3-(4-morpholinyl)propyl] pyrrolo[2,1-f] [1,2,4]triazine-6-carboxamide To a solution of 5-fluoro oxindole (36 mg, 0.24 mmol) in DMF (1 mL) was added NaH (5.9 mg, 0.23 mmol). After 30 min at rt, a solution of Compound B of Example 132 (24 mg, 0.072 mmol) in DMF (1 mL) was added and the resulting mixture was stirred at ambient temperature over 1 h. The solvent was removed in vacuo and the mixture was purified by RP HPLC. The methanol in the desired HPLC fractions was removed in vacuo and the resulting aqueous solution neutralized using saturated sodium bicarbonate solution, then extracted with ethyl acetate. The organic layer was dried (MgSO$_4$) and the volatiles were removed in vacuo. The solid obtained was dissolved in acetonitrile/MeOH and treated with 1 N HCl in diethyl ether. The mixture was stirred at ambient temperature over 1 h and the solvents removed in vacuo. The HCl salt of the title compound was obtained as an orange solid (18 mg, 51%). MS: (M+H)$^+$=453.

Example 135

The following two compounds were prepared by treatment of compound B of Example 132 with appropriately substituted oxindole using the procedure described for the synthesis of Example 134.
4-(6-Fluoro-2,3-dihydro-2-oxo-1H-indol-3-yl)-5-methyl-N-[3-(4-morpholinyl)propyl]pyrrolo[2,1-f] [1,2,4]triazine-6-carboxamide;
4-[5-(Aminosulfonyl)-2,3-dihydro-2-oxo-1H-indol-3-yl]-5-methyl-N-[3-(4-morpholinyl)propyl]pyrrolo[2, 1-f][1,2, 4]triazine-6-carboxamide.

Example 136

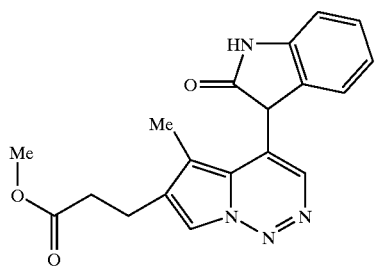

4-(2,3-Dihydro-2-oxo-1H-indol-3-yl)-5-methylpyrrolo[2,1-f][1,2,4]triazine-6-propanoic Acid Methyl Ester A) 4-Phenoxy-5-methylpyrrolo[2,1-f][1,2,4]triazine-6-propenoic Acid Methyl Ester DBU (1.42 mL, 9.49 mmol) was added to a solution of the Compound C of Example 130 (600 mg, 2.37 mmol) and methyl diethylphosphonoacetate (1.74 mL, 9.49 mmol) in 1,2-dichloroethane (20 mL). After stirring at rt overnight, the reaction mixture was diluted with dichloromethane and washed with aqueous 2% citric acid, brine, dried (MgSO$_4$), and concentrated. The organic extract was concentrated and the residue was purified by chromatography on silica gel and elution with 20% ethyl acetate (EtOAc)/DCM to afford a white solid (710 mg. 97%). MS: (M+H)$^+$=310.

B) 4-Hydroxy-5-methylpyrrolo[2,1-f][1,2,4]triazine-6-propanoic Acid Methyl Ester Pd/C (10%, 70 mg) was added to a solution of the Compound A (710 mg, 2.30 mmol) in a solvent mixture EtOAc/MeOH/THF/AcOH (100 mL/100 mL/20 mL/2 mL). The suspension was stirred under hydrogen for 2h. The reaction mixture was passed through Celite, the Celite was washed with MeOH and the filtrate was concentrated in vacuo to give crude product. Trituration with hexanes afforded Compound B as a white solid (430 mg, 88%). MS:(M+H)$^+$=236.

C) 4-Chloro-5-methylpyrrolo[2,1-f][1,2,4]triazine-6-propanoic Acid Methyl Ester

A mixture of diisopropylethylamine (0.24 mL, 1.4 mmol), Compound B (220 mg, 0.94 mmol) and POCl$_3$ (3 mL) was heated in a sealed bottle at 80° C. After 2 h, the mixture was cooled down to rt and concentrated in vacuo to give a residue. The residue was partitioned between DCM and aqueous NaHCO$_3$ solution. The DCM layer was separated, dried (MgSO$_4$) and concentrated in vacuo to give a dark green solid. Purification by chromatography on silica gel and elution with 20% EtOAc/DCM afforded yellow solid (220 mg, 92%). MS: (M+H)$^+$=254.

D) 4-(2,3-Dihydro-2-oxo-1H-indol-3-yl)-5-methylpyrrolo[2,1-f][1,2,4]triazine-6-propanoic Acid Methyl Ester NaH (60% in oil, 28 mg, 0.71 mmol) was added to a solution of oxindole (94 mg, 0.71 mmol) in DMF (2 mL) under argon and the mixture was stirred for 10 min. Compound C (60 mg, 0.24 mmol) was added to the solution. After 1 h at rt, the reaction was quenched by the addition of acetic acid and diluted with DCM. The organic solution was washed with water, dried (MgSO$_4$), and concentrated in vacuo to give crude product. Purification by chromatography on silica gel and elution with 20% EtOAc/DCM afforded the title compound as a pure yellow solid (78 mg, 94%). MS: (M+H)$^+$=351.

Example 137

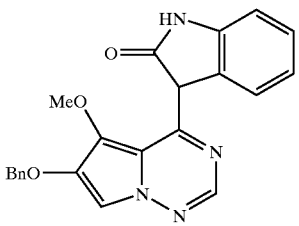

1,3-Dihydro-3-[5-methoxy-6-(phenylmethoxy)pyrrolo[2,1-f][1,2,41 triazin-4-yl]-2H-indol-2-one A) 4-Hydroxy-5-methoxypyrrolo[2,1-f][1,2,4]triazine-6-methanol Compound F of Example 96 (3.56 g, 15 mmol) was combined with lithium tri-tert-butoxyaluminohydride (1 M solution in THF, 60 mL, 60 mmol) and heated at reflux overnight. The reaction mixture was allowed to cool to rt and quenched with 1 N aqueous HCl. The mixture was concentrated to remove volatiles and the remaining material was combined with 100 g of silica gel and applied to a flash silica gel column which was eluted with ethyl acetate to provide 2.65 g (90%) of compound A. MS: [M+H]$^+$=196.

B) 2,2-Dimethylpropanoic acid [6-(hydroxymethyl)-5-methoxy-4-oxopyrrolo[2,1-f][1,2,4]triazin-3(4H)-yl]methyl Ester Compound A (195 mg, 1 mmol) was dissolved in 1.5 mL of N,N-dimethylformamide. Sodium hydride (60% in oil, 48 mg, 1.2 mmol) was added and the reaction mixture was stirred at rt for 0.5 hr. Chloromethyl pivalate (1181 mg, 1.2 mmol) was added and the mixture was stirred for 1 hr. Water was added and the mixture was extracted with ethyl acetate (3×10 mL). The combined extracts were dried ($Na_2SO_4$), concentrated in vacuo and purified by flash column chromatography on silica gel eluting with 33% ethyl acetate in hexanes to provide 260 mg (84%) of compound B as a solid. MS: $[M+H]^+=310$.

C) 2,2-Dimethylpropanoic acid[6-formyl-5-methoxy-4-oxopyrrolo[2,1-f] [1,2,4]triazin-3(4H)-yl] methyl Ester Compound B (740 mg, 2.39 mmol) was suspended in toluene (10 mL) with manganese dioxide (835 mg, 9.6 mmol) and heated at 100° C. for 3 hr. The reaction mixture was cooled to rt, filtered, and the precipitate was washed with ethyl acetate. The filtrate was concentrated in vacuo to provide 660 mg (90%) of compound C as a solid. MS: $[M+H]^+=308$.

D) 2,2-Dimethylpropanoic acid[6-formyloxy-5-methoxy-4-oxopyrrolo[2,1-f] [1,2,4]triazin-3(4H)-yl]methyl Ester

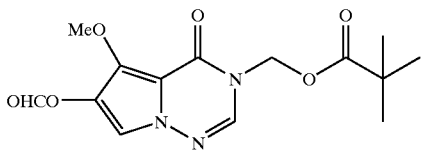

Compound C (660 mg, 2.15 mmol) was dissolved in $CH_2Cl_2$ (10 mL) and m-chloroperoxybenzoic acid (57%, 745 mg, 2.46 mmol) was added with $MgSO_4$ (2.0 g) and the reaction mixture was stirred at rt for 5 hr. The mixture was filtered and the filtrate was washed with aqueous $NaHCO_3$ solution twice, dried ($MgSO_4$), and concentrated to provide 680 mg (98%) of compound D as a solid. MS: $[M+H]^+=324$.

E) 2,2-Dimethylpropanoic acid[5-methoxy-4-oxo-6-(phenylmethoxy)pyrrolo[2,1-f][1,2,4]triazin-3(4H)-yl]methyl Ester Compound D (680 mg, 2.10 mmol, 1 eq) was dissolved in acetone (10 mL) foloowed by the addition of benzyl bromide (430 mg, 2.5 mmol) and $K_2CO_3$ (1.0 g, 7.25 mmol). The reaction mixture was stirred at 60° C. for 10 hr, cooled to rt, and filtered. The filtrate was concentrated and purified by flash silica gel chromatography eluting with 25% ethyl acetate in hexanes to provide 485 mg (60%) of E as a gel. MS: $[M+H]^+= 386$;

F) 5-Methoxy-6-(phenylmethoxy)pyrrolo[2,1-f][1,2,4]triazin-4(3H)-one

Compound E (65 mg, 0.17 mmol) was stirred at rt in a mixture of methanol (1 mL) and ammonium hydroxide (0.2 mL) for 6 hrs. The mixture was concentrated in vacuo, dissolved in $CH_2Cl_2$, and purified by flash silica gel chromatography eluting with 33% ethyl acetate in hexanes to provide 45 mg (97%) of compound F as a solid. MS: $[M+H]^+=272$.

G) 4-Chloro-5-methoxy-6-(phenylmethoxy)pyrrolo[2,1-f][1,2,4]triazine

Compound F (44 mg, 0.16 mmol) was stirred with $POCl_3$ (0.5 mL) at 60° C. for 3 hr. The mixture was concentrated in vacuo, dissolved in $CH_2Cl_2$ (2 mL), and stirred with solid $NaHCO_3$ for 10 min. The mixture was filtered and concentrated to provide 46 mg (99%) of compound G as a solid. MS: $[M+H]^+=286$ (replacement of Cl by $OCH_3$ upon standing in methanol); R.T.=3.265 min (YMC S5 ODS column 4.6×50 mm, 10-90% aqueous methanol over 4 minutes containing 0.2% phosphoric acid, 4 mL/min, monitoring at 220 nm); $^1H$ NMR ($CDCl_3$): δ 8.01 (s, 1H), 7.45-7.30 (m, 6H), 5.15 (s, 2H), 4.03 (s, 3H).

H) 1,3-Dihydro-3-[5-methoxy-6-(phenylmethoxy)pyrrolo[2,1-f] [1,2,4]triazin-4-yl]-2H-indol-2-one To a suspension of NaH (60% in oil, 19.2 mg, 0.48 mmol) in of N,N-dimethylformamide (0.5 mL) was added oxindole (63.4 mg, 0.48 mmol). The reaction mixture was stirred for 1 hr at rt. Compound G (38 mg, 0.16 mmol, 1 eq) was added, and the mixture was stirred for 1 hr more. The mixture was diluted with water and filtered. The resulting solid material was triturated with methanol and dried to provide 38 mg (62%) of the title compound. MS: $[M+H]^+=387$; $^1H$ NMR (d-DMSO): δ 12.83 (br s, 1H), 10.64 (br s, 1H), 7.78 (s, 1H), 7.60 (s, 1H), 7.50-7.31 (m, 6H), 7.02-6.94 (m, 1H), 6.89-6.82 (m, 2H), 5.10 (s, 2H), 3.55 (s, 3H).

Example 138

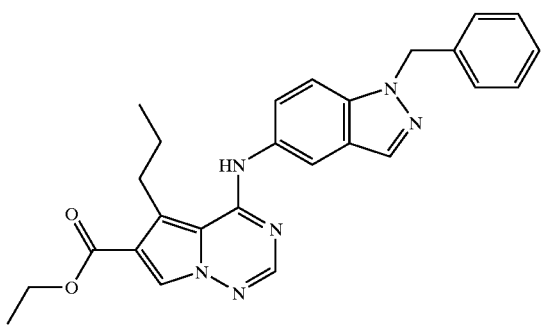

4-[1'-(Phenylmethyl)-1H-indazol-5-yl]amino]-5-propylpyrrolo[2,1-f] [1,2,4]triazine-6-carboxylic acid ethyl ester

A) 3-Propylpyrrole-2,4-dicarboxylic Acid Diethyl Ester

Ethyl isocyanoacetate (4.52 g, 40.0 mmol) was combined with 1,8-diazabicyclo[5.4.0]undec-7-ene (6.09 g, 40.0 mmol) in THF (120 mL). The mixture was warmed to 45° C. and butyraldehyde (1.44 g, 20.0 mmol) was added in THF (120 mL) over 30 min. The reaction mixture was stirred at 50° C. for 1.5 hr and then was allowed to cool to rt overnight. The solvent was removed in vacuo and the resulting brown oil was dissolved in of ethyl acetate (100 mL) and washed with of water (75 mL). The aqueous layer was extracted with ethyl acetate (2×100 mL). The combined organic extracts were washed with 0.1 N aqueous HCl (2×100 mL) and water (75 mL), dried (Na$_2$SO$_4$)and concentrated in vacuo to provide 4.270 g (84%) of compound A as a brown oil which was used without further purification. $^1$H NMR (CDCl$_3$): δ 9.17 (br s, 1H), 7.47 (s, 1H), 4.33 (q, J=7.1 Hz, 2H), 4.27 (q, J=7.1 Hz, 2H), 3.07-3.04 (m, 2H), 1.85-1.78 (m, 2H), 1.39-1.26 (m, 6H), 0.98-0.95 (m, 3H).

B) 1-Amino-3-propylpyrrole-2,4-dicarboxylic Acid Diethyl Ester

To a suspension of NaH (60% in oil, 0.96 g, 24 mmol) in N,N-dimethylformamide (100 mL) was added compound A (3.06 g, 12 mmol). After 20 min at rt, diphenyl phosphoryl hydroxylamine (5.56 g, 24 mmol) was added, and the mixture was stirred for additional 3 hr. The solvent was removed in vacuo, and the residue was dissolved in ethyl acetate and washed with pH 7 phosphate buffer. The organic extracts were dried (Na$_2$SO$_4$) and purified by flash chromatography on silica gel eluting with 20% ethyl acetate in hexanes to provide 2 g (63%) of compound B. MS: [M+H]$^+$=269.2.

C) 5-Propylpyrrolo[2,1-f][1,2,4]triazin-4(3H)-one-6-carboxylic Acid Ethyl Ester

Compound B (2 g, 7 mmol) was combined with formamide (4.53 g, 100 mmol) and stirred at 160° C. for 7 hr. The reaction mixture was allowed to cool to rt. Ice was added to the mixture and the resulting precipitate was filtered off and dried to afford 1.6 g (86%) of compound C. MS: [M−H]$^-$=247.9.

D) 4-[[1-(Phenylmethyl)-1H-indazol-5-yl]amino]-5-propylpyrrolo[2,1-f] [1,2,4]triazine-6-carboxylic Acid Ethyl Ester Compound C (19 mg, 0.076 mmol) was stirred with POCl$_3$ (0.5 mL) at 100° C. for 4 hr under Argon. The reaction mixture was concentrated in vacuo. CH$_3$CN (2.50 mL) was added followed by 5-amino-1-benzyl-1H-indazole (25 mg, 0.114 mmol). After 16 hr at rt the mixture was diluted with of ethyl acetate (50 mL) and washed with saturated aqueous NaHCO$_3$. The combined organic washes were dried (Na$_2$SO$_4$), concentrated in vacuo, and purified by flash chromatography on silica gel eluting with 40% ethyl acetate in hexanes to provide 20 mg (58%) of the title compound as a yellow-brown oil. MS: [M+H]$^+$=455.2; $^1$H NMR (CDCl$_3$): δ 8.11 (s, 1H), 8.07 (s, 1H), 8.02 (s, 1H), 7.94 (s, 1H), 7.45-7.19 (m, 7H), 5.61 (s, 2H), 4.35 (q, J=7.2 Hz, 2H), 3.29 (t, J=8.2 Hz, 2H), 1.85-1.78 (m, 2H), 1.39 (t, J=7.2 Hz, 3H), 1.11 (t, J=7.2 Hz, 3H).

Example 139

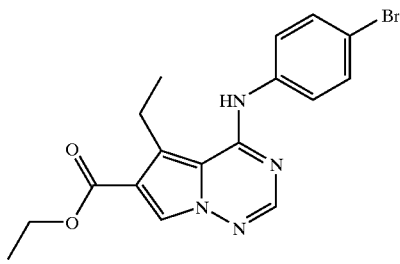

4-[(4-Bromophenyl)amino]-5-ethylpyrrolo[2,1-f][1,2,4]triazine-6-carboxylic acid ethyl ester A) 3-Ethylpyrrole-2,4-dicarboxylic Acid Diethyl Ester Ethyl isocyanoacetate (50.67 g, 0.448 mol, 2 eq) was combined with 1,8-diazabicyclo[5.4.0]undec-7-ene (68.2 g, 0.45 mol) in 1.0 L of tetrahydrofuran. The mixture was warmed to 50° C. and propanal (13 g, 0.224 mol, 1 eq) was added in 250 mL of tetrahydrofuran. The reaction was stirred at 50° C. for 2 hrs. The mixture was allowed to cool to rt and stirred overnight. The solvent was removed in vacuo. The resulting brown oil began to crystallize upon standing. The material was triturated with ether, and the resulting solid was collected by filtration and dried to provide (14.0 g, 26%) of compound A as a brown solid. Additional material (18.3 g, 34%) was obtained upon concentration of the mother liquor. MS: [M+H]$^+$=240.

B) 5-Ethylpyrrolo[2,1-f][1,2,4]triazin-4(3H)-one-6-carboxylic Acid Ethyl Ester

Compound A (13.8 g, 57.8 mmol) was converted to compound B (8 g, 58%) as a pale yellow solid using the procedure described for the preparation of compound C from compound A in Example 138. MS: [M+H]$^+$=235.0

C) 4-[(4-Bromophenyl)amino]-5-ethylpyrrolo[2,1-f] [1,2,4]triazine-6-carboxylic Acid Ethyl Ester Compound B (210 mg, 0.893 mmol) was stirred with POCl$_3$ (5 mL) at 100° C. for 5.5 hr under Argon. The reaction mixture was concentrated in vacuo. Toluene (5 mL) was added to the residue and then removed in vacuo. CH$_3$CN (5 mL) was then added followed by 4-bromoaniline (460 mg, 2.68 mmol). After 14 hr at rt the reaction mixture was poured into saturated aqueous NaHCO$_3$ and extracted with ethyl acetate (3×75 mL). The combined organic washes were dried (Na$_2$SO$_4$), concentrated in vacuo, and purified by flash chromatography on silica gel eluting with 40% ethyl acetate in hexanes to provide 320 mg (92%) of the title compound as a white crystalline solid. MS: [M+H]$^+$=389.1; $^1$H NMR (CDCl$_3$): δ 7.99 (s, 1H), 7.94 (s, 1H), 7.58 (d, J=8.8 Hz, 1H), 7.49 (d, J=8.8 Hz, 1H), 4.35 (q, J=7.0 Hz, 2H), 3.29 (t, J=7.9 Hz, 2H), 1.41-1.37 (m, 6H).

Example 140

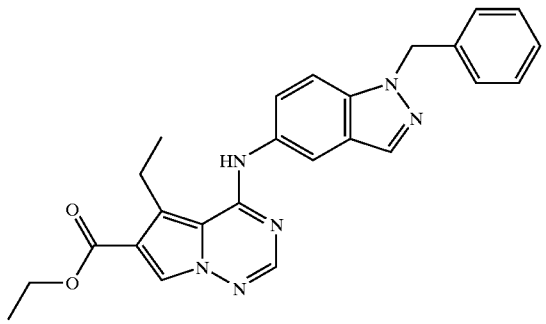

4-[[1-(Phenylmethyl)-1H-indazol-5-yl]amino]-5-ethylpyrrolo[2,1-f] [1,2,4]triazine-6-carboxylic Acid Ethyl Ester The title compound was prepared from compound B of Example 139 using the process described for the preparation of example 139 except 5-amino-1-benzyl-1H-indazole was used to add to the chloroimidate. MS: $(M+H)^+=441.24$

Example 141

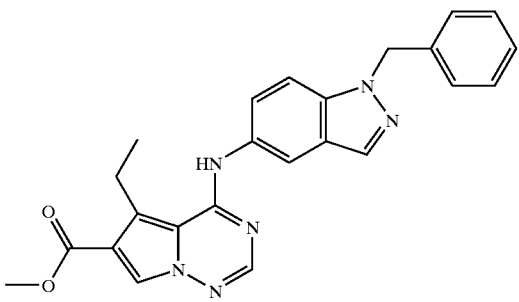

5-Ethyl-4-[[1-(phenylmethyl)-1H-indazol-5-yl]amino]pyrrolo[2,1-f] [1,2,4]triazine-6-carboxylic Acid Methyl Ester Sodium methoxide was generated by addition of NaH (0.163 g, 6.8 mmol) to anhydrous methanol (115 mL) under Argon at 0° C. The mixture was stirred at 0° C. for 20 min. Example 140 (30 mg, 0.068 mmol) was added in one portion and the resulting mixture was stirred at rt for 18 hr. The reaction mixture was poured into 50 mL pH 7 phosphate buffer. The aqueous phase was extracted with ethyl acetate (2×75 mL). The combined organic washes were dried (Na$_2$SO$_4$), concentrated in vacuo, and purified by flash chromatography on silica gel eluting with 40% ethyl acetate in hexanes to provide 17.8 mg (61%) of the title compound as a white solid. MS: $[M+H]^+=427.2$; $^1$H NMR (CDCl$_3$): 8.09 (s, 1H), 8.06 (s, 1H), 8.00 (s, 1H), 7.94 (s, 1H), 7.46-7.19 (m, 7H), 5.61 (s, 2H), 3.89 (s, 3H), 3.33 (q, J=7.7 Hz, 2H), 1.42 (t, J=7.7 Hz, 6H).

Example 142

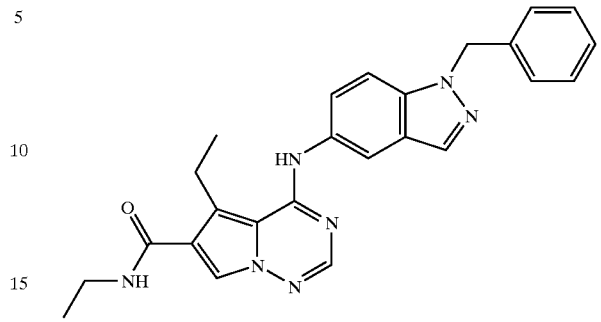

N,5-Diethyl-4-[[1-(phenylmethyl)-1H-indazol-5-yl] amino]pyrrolo[2,1-f] [1,2,4]triazine-6-carboxamide A. 5-Ethyl-4-[[1-(phenylmethyl)-1H-indazol-5-yl] amino]pyrrolo[2,1-f] [1,2,4]triazine-6-carboxylic Acid Example 140 (320 mg, 0.726 mmol) was dissolved in a mixture of THF (6 mL), methanol (2 mL), and water (2 mL). LiOH (305 mg, 7.26 mmol) was added and the reaction mixture was stirred at 50° C. for 24 hr. The mixture was poured into 125 mL pH 4 phosphate buffer and extracted with ethyl acetate (3×125 mL). The combined organic washes were dried (Na$_2$SO$_4$)and concentrated in vacuo to provide a quantitative yield of compound A as a white solid. MS: $[M+H]^+=413$.

B. N,5-Diethyl-4-[[1-(phenylmethyl)-1H-indazol-5-yl] amino]pyrrolo[2,1-f][1,2,4]triazine-6-carboxamide Compound A (31 mg, 0.075 mmol) was dissolved under Argon in a mixture of N,N-dimethylformamide (1.5 µL) and CH$_3$CN (1.5 mL). Ethylamine (2.0 M in THF, 38 µL, 0.075 mmol) and 1-[3-dimethylamino)propyl]-3-ethylcarbodiimide hydrochloride (14 mg, 0.075 mmol) were added, and the reaction was stirred at rt for 18 hr. The mixture was poured into 50 mL of water and extracted with ethyl acetate (2×75 mL). The combined organic washes were dried (Na$_2$SO$_4$), concentrated in vacuo, and purified by flash chromatography on silica gel eluting with 75% ethyl acetate in hexanes to provide 11 mg (33%) of the title compound as a white film. MS: $[M+H]^+=440.2$; $^1$H NMR (CDCl$_3$): δ 8.10 (s, 1H), 8.06 (s, 1H), 7.93 (s, 1H), 7.71 (s, 1H), 7.46-7.19 (m, 7H), 5.87 (br s, 1H), 5.61 (s, 2H), 3.52-3.45 (m, 2H), 3.30 (q, J=7.5 Hz, 2H), 1.44 (t, J=7.5 Hz, 3H), 1.25 (t, J=7.5 Hz, 3H).

The compounds named in Example 143 were prepared using methods analogous to the procedures described hereinbefore.

Example 143

4-(2,3-Dihydro-2-oxo-1H-indol-3-yl)-N-[[[3(dimethylamino)propyl]amino]carbonyl]-N-ethyl-5-methylpyrrolo[2,1-f] [1,2,4]triazine-6-carboxamide;

4-[(3-Bromophenyl)amino]-5-ethylpyrrolo[2,1-f][1,2,4]triazine-6-carboxylic acid ethyl ester;

5-Ethyl-4-[(4-phenoxyphenyl)amino]pyrrolo[2,1-f][1,2,4] triazine-6-carboxylic acid ethyl ester;

5-Ethyl-4-[[1-(phenylmethyl)-1H-indazol-4-yl]amino]pyrrolo[2,1-f][1,2,4]triazine-6-carboxylic acid ethyl ester;

4-(2,3-Dihydro-2-oxo-1H-indol-3-yl)-5-methyl-N-[3-(4-morpholinyl)propyl]pyrrolo[2,1-f][1,2,4]triazine-6-carboxamide;

4-(2,3-Dihydro-2-oxo-1H-indol-3-yl)-5-methyl-N-[2-(4-morpholinyl)ethyl]pyrrolo[2, 1-f][1,2,4]triazine-6-carboxamide;

4-(2,3-Dihydro-2-oxo-1H-indol-3-yl)-N-[[[3 (dimethylamino)propyl]amino]carbonyl]-N-ethyl-5-methylpyrrolo[2,1-f] [1,2,4]triazine-6-carboxamide;

4-[(3-Bromophenyl)amino]-5-ethylpyrrolo[2,1-f][1,2,4]triazine-6-carboxylic acid ethyl ester;

5-Ethyl-4-[(4-phenoxyphenyl)amino]pyrrolo[2,1-f][1,2,4]triazine-6-carboxylic acid ethyl ester;

5-Ethyl-4-[[1-(phenylmethyl)-1H-indazol-4-yl]amino]pyrrolo[2,1-f][1,2,4]triazine-6-carboxylic acid ethyl ester;

4-(6-Cyano-2,3-dihydro-2-oxo-1H-indol-3-yl)-5-methylpyrrolo[2,1-f][1,2,4]triazine-6-carboxylic acid methyl ester;

4-(2,5-Dihydro-3-methyl-5-oxo-1H-pyrazol-1-yl)-5-methylpyrrolo[2,1-f][1,2,4]triazine-6-carboxylic acid methyl ester;

3-(6-Amino-5-methylpyrrolo[2,1-f][1,2,4]triazin-4-yl)-1,3-dihydro-2H-indol-2-one;

3-(6-Amino-5-methylpyrrolo[2,1-f][1,2,4]triazin-4-yl)-1,3-dihydro-2H-indol-2-one;

N-[4-(2,3-Dihydro-2-oxo-1H-indol-3-yl)-5-methylpyrrolo[2,1-f][1,2,4]triazin-6-yl]N'-[2-(4-morpholinyl)ethyl]urea;

N-[4-(2,3-Dihydro-2-oxo-1H-indol-3-yl)-5-methylpyrrolo[2,1-f][1,2,4]triazin-6-yl]N'-[ 3-(4-morpholinyl)propyl]urea;

N-[4-(2,3-Dihydro-2-oxo-1H-indol-3-yl)-5-methylpyrrolo[2,1-f][1,2,4]triazin-6-yl]N'-[4-(4-morpholinyl)butyl]urea;

5-Ethyl-4-[[1-(phenylmethyl)-1H-indazol-5-yl]amino]pyrrolo[2,1-f][1,2,4]triazine-6-methanol;

5-Ethyl-N-[3-(1H-imidazol-1-yl)propyl]-4-[[1-(phenylmethyl)-1H-indazol-5-yl]amino]pyrrolo[2, 1-f][1,2,4]triazine-6-carboxamide;

4-(2,3-Dihydro-2-oxo-1H-indol-3-yl)-5-methyl-N-[3-(1 pyrrolidinyl)propyl]pyrrolo[2, 1-f][1,2,4]triazine-6-carboxamide;

5-Ethyl-N-[2-(4-morpholinyl)ethyl]-4-[[1-(phenylmethyl)-1H-indazol-5-yl]amino] pyrrolo[2,1-f][1,2,4]triazine-6-carboxamide;

5-Ethyl-N-[6-[3-(1H-imidazol-1-yl)propyl]-2-pyridinyl]-4-[[1-(phenylmethyl)-1 H-indazol-5-yl]amino]pyrrolo[2,1-f] [1,2,4]triazine-6-carboxamide;

7-Bromo-5-ethyl-4-[[1-(phenylmethyl)-1H-indazol-5-yl] amino]pyrrolo[2,1-f] [1,2,4]triazine-6-carboxylic acid ethyl ester;

7-Bromo-5-ethyl-4-[[1-(phenylmethyl)-1H-indazol-5-yl] amino]pyrrolo[2, 1 f] [1,2,4]triazine-6-methanol;

N-[4-(2,3-Dihydro-2-oxo-1H-indol-3-yl)-5-methylpyrrolo[2,1-f][1,2,4]triazin-6-yl]-4-morpholinebutanamide;

5-Ethyl-6-[[2-(4-morpholinyl)ethoxy]methyl]-N-[1-(phenylmethyl)-1H-indazol-5-yl]pyrrolo[2,1-f][1,2,4]triazin-4-amine;

7-Bromo-5-ethyl-N-[2-(4-morpholinyl)ethyl]-4-[[1-(phenylmethyl)-1H-indazol-5-yl]amino]pyrrolo[2,1-f][1,2,4]triazine-6-carboxamide;

N-[4-(2,3-Dihydro-2-oxo-1H-indol-3-yl)-5-methylpyrrolo[2,1-f][1,2,4]triazin-6-yl]-2-methylpropanamide;

3-[6-(Dimethylamino)-7-(hydroxymethyl)-5-methylpyrrolo[2,1-f][1,2,4]triazin-4-yl] -1,3-dihydro-2H-indol-2-one;

N-[4-(2,3-Dihydro-2-oxo-1H-indol-3-yl)-5-methylpyrrolo[2,1-f][1,2,4]triazin-6-yl]methanesulfonamide;

3-(5,6-Dimethoxypyrrolo[2,1-f][1,2,4]triazin-4-yl)-1,3-dihydro-2H-indol-2-one;

N-[4-(2,3-Dihydro-2-oxo-1H-indol-3-yl)-5-methylpyrrolo[2,1-f][1,2,4]triazin-6-yl]-4-morpholinepropanesulfonamide;

[4-(2,3-Dihydro-2-oxo-1H-indol-3-yl)-5-methoxypyrrolo[2, 1-f][1,2,4]triazin-6-yl] carbamic acid phenylmethyl ester;

1,3-Dihydro-3-[5-methoxy-6-[[4-(4-methyl-1-piperazinyl) butyl]amino]pyrrolo[2,1-f] [1,2,4]triazin-4-yl]-2H-indol-2-one;

3-(6-Amino-5-methoxypyrrolo[2,1-f][1,2,4]triazin-4-yl)-1, 3-dihydro-2H-indol-2-one;

1,3-Dihydro-3-[5-methoxy-6-[[4-(4-morpholinyl)butyl] amino]pyrrolo[2,1-f] [1,2,4]triazin-4-yl]-2H-indol-2-one;

4-[(3-Hydroxy-5-methylphenyl)amino]-5-methylpyrrolo[2, 1-f][1,2,4]triazine-6-carboxylic acid methyl ester;

4-[(4-Ethyl-3-hydroxyphenyl)amino]-5-methylpyrrolo[2,1-f][1,2,4]triazine-6-carboxylic acid methyl ester;

5-[(5,6-Dimethoxypyrrolo[2,1-f][1,2,4]triazin-4-yl)amino]-2-methylphenol;

4-[(4-Bromo-3-hydroxyphenyl)amino]-5-methylpyrrolo[2, 1-f][1,2,4]triazine-6-carboxylic acid methyl ester;

4-[[3-Hydroxy-4-(1-methylethyl)phenyl]amino]-5-methylpyrrolo[2,1-f][1,2,4]triazine-6-carboxylic acid methyl ester;

5-[(6-Amino-5-methylpyrrolo[2,1-f][1,2,4]triazin-4-yl) amino]-2-methylphenol;

5-Ethyl-4-[(6-methoxy-3-pyridinyl)amino]-N-[2-(1-pyrrolidinyl)ethyl]pyrrolo[2,1-f] [1,2,4]triazine-6-carboxamide;

5-Ethyl-4-[(6-methoxy-3-pyridinyl)amino]-N-methyl-N-[2-(1-pyrrolidinyl)ethyl]pyrrolo[2,1-f] [1,2,4]triazine-6-carboxamide;

4-[(4-Hydroxy-2-naphthalenyl)amino]-5-methylpyrrolo[2, 1-f][1,2,4]triazine-6-carboxylic acid methyl ester;

4-[(4-Carboxy-3-hydroxyphenyl)amino]-5-methylpyrrolo [2,1-f][1,2,4]triazine-6-carboxylic acid methyl ester;

4-[(3-Chloro-4-fluorophenyl)amino]-5-methylpyrrolo[2,1-f][1,2,4]triazine-6-carboxylic acid methyl ester;

4-[(3-Chloro-4-fluorophenyl)amino]-5-ethylpyrrolo[2,1-f] [1,2,4]triazine-6-carboxylic acid ethyl ester;

1,3-Dihydro-3-(6-methoxy-5-methylpyrrolo[2,1-f][1,2,4] triazin-4-yl)-2H-indol-2-one;

4-[(3-Chloro-4-fluorophenyl)amino]pyrrolo[2,1-f][1,2,4] triazine-6-carboxylic acid methyl ester;

4-[3-[4-(2,3-Dihydro-2-oxo-1H-indol-3-yl)-5-methylpyrrolo[2,1-f][1,2,4]triazin-6-yl] -1-oxopropyl]morpholine;

1-[3-[4-(2,3-Dihydro-2-oxo-1H-indol-3-yl)-5-methylpyrrolo[2,1-f][1,2,4]triazin-6-yl]    -1-oxopropyl]-4-methylpiperazine;

4-(2,3-Dihydro-2-oxo-1H-indol-3-yl)-5,6-dimethoxypyrrolo[2,1-f][1,2,4]triazine-7-carboxylic acid methyl ester;

4-[(4-Butyl-3-hydroxyphenyl)amino]-5-methylpyrrolo[2,1-f][1,2,4]triazine-6-carboxylic acid methyl ester;

4-[(3-Hydroxy-4-propylphenyl)amino]-5-methylpyrrolo[2, 1-f][1,2,4]triazine-6-carboxylic acid methyl ester;

4-[(3-Hydroxy-4-methylphenyl)amino]-5-propylpyrrolo[2, 1-f][1,2,4]triazine-6-carboxylic acid ethyl ester;

4-(2,3-Dihydro-2-oxo-1H-indol-3-yl)-N-(2-methoxyethyl)-5-methylpyrrolo[2, 1-f] [1,2,4]triazine-6-carboxamide;

4-(2,3-Dihydro-2-oxo-1H-indol-3-yl)-N-(3-methoxypropyl)-5-methylpyrrolo[2,1-f] [1,2,4]triazine-6-carboxamide;

4-(2,3-Dihydro-2-oxo-1H-indol-3-yl)-5-methyl-N-[(tetrahydro-2-furanyl)methyl]pyrrolo[2,1-f][1,2,4]triazine-6-carboxamide;
5-Ethyl-4-[[1-(phenylmethyl)-1H-indazol-5-yl]amino]pyrrolo[2,1-f][1,2,4]triazine-6-carboxylic acid methyl ester;
5-Ethoxy-4-[(3-hydroxy-4-methylphenyl)amino]pyrrolo[2,1-f][1,2,4]triazine-6-carboxylic acid ethyl ester;
4-[(4-Ethyl-3-hydroxyphenyl)amino]-5-methyl-N-[3-(4-morpholinyl)propyl]pyrrolo[2,1-f][1,2,4]triazine-6-carboxamide;
4-[(4-Bromo-3-hydroxyphenyl)amino]-5-methyl-N-[3-(4-morpholinyl)propyl]pyrrolo[2,1-f][1,2,4]triazine-6-carboxamide;
5-Ethyl-4-(phenylamino)pyrrolo[2,1-f][1,2,4]triazine-6-carboxylic acid ethyl ester;
5-Ethyl-4-(methylphenylamino)pyrrolo[2,1-f][1,2,4]triazine-6-carboxylic acid ethyl ester;
5-Ethyl-4-(1,2,3,4-tetrahydro-2-isoquinolinyl)pyrrolo[2,1-f][1,2,4]triazine-6-carboxylic acid ethyl ester;
4-[(3-Hydroxy-4-methylphenyl)amino]-N-(3-methoxypropyl)-5-methylpyrrolo[2,1-f] [1,2,4]triazine-6-carboxamide;
4-[(3-Hydroxy-4-methylphenyl)amino]-5-methyl-N-[3-(4-methyl-1-piperazinyl)propyl]pyrrolo[2,1-f][1,2,4]triazine-6-carboxamide;
4-[(3-Hydroxy-4-methylphenyl)amino]-N,5-dimethylpyrrolo[2,1-f][1,2,4]triazine-6-carboxamide;
N-[2-(Dimethylamino)ethyl]-4-[(3-hydroxy-4-methylphenyl)amino]-5-methylpyrrolo[2,1-f][1,2,4]triazine-6-carboxamide;
5-Ethyl-4-(1,2,3,4-tetrahydro-1-quinolinyl)pyrrolo[2,1-f][1,2,4]triazine-6-carboxylic acid ethyl ester;
5-Ethyl-4-[(phenylmethyl)amino]pyrrolo[2,1-f][1,2,4]triazine-6-carboxylic acid ethyl ester;
4-(2,3-Dihydro-2-oxo-1H-indol-3-yl)-5-ethoxypyrrolo[2,1-f][1,2,4]triazine-6-carboxylic acid ethyl ester;
4-[(3-Hydroxy-4-methylphenyl)amino]-5-methyl-N-[3-(1-pyrrolidinyl)propyl]pyrrolo[2,1-f][1,2,4]triazine-6-carboxamide;
5-Ethyl-4-[(2-phenylethyl)amino]pyrrolo[2,1-f][1,2,4]triazine-6-carboxylic acid ethyl ester;
N-[4-(Dimethylamino)butyl]-4-[(3-hydroxy-4-methylphenyl)amino]-5-methylpyrrolo[ 2,1-f][1,2,4]triazine-6-carboxamide;
4-[(3-Hydroxy-4-methylphenyl)amino]-5-(1-methylethyl) pyrrolo[2,1-f] [1,2,4]triazine-6-carboxylic acid ethyl ester;
4-[(3-Hydroxy-4-methylphenyl)amino]-5-methyl-N-[3-(methylsulfonyl)propyl]pyrrolo[2,1-f][1,2,4]triazine-6-carboxamide;
4-[(3-Chloro-4-fluorophenyl)methyl]-5-(1-methylethyl)pyrrolo[2,1-f][1,2,4]triazine-6-carboxylic acid ethyl ester;
[4-[(3-Chloro-4-fluorophenyl)amino]-5-ethylpyrrolo[2,1-f][1,2,4]triazin-6-yl]carbamic acid phenylmethyl ester;
5-(1-Methylethyl)-4-[[1-(phenylmethyl)-1H-indazol-5-yl]amino]pyrrolo[2,1-f] [1,2,4]triazine-6-carboxylic acid ethyl ester;
4-(Butylamino)-5-ethylpyrrolo[2,1-f][1,2,4]triazine-6-carboxylic acid ethyl ester
5-Ethyl-4-[(2-methoxyethyl)amino]pyrrolo[2,1-f][1,2,4]triazine-6-carboxylic acid ethyl ester;
5-Ethyl-4-(4-morpholinyl)pyrrolo[2,1-f][1,2,4]triazine-6-carboxylic acid ethyl ester;
5-Ethyl-4-[[3-(1H-imidazol-1-yl)propyl]amino]pyrrolo[2,1-f][1,2,4]triazine-6-carboxylic acid ethyl ester;
2-Methyl-5-[[5-methyl-6-[3-(2H-1,2,3-triazol-2-yl)propoxy]pyrrolo[2,1-f] [1,2,4]triazin-4-yl]amino]phenol;
5-Ethyl-4-[[(1-S)-1-phenylethyl]amino]pyrrolo[2,1-f][1,2,4]triazine-6-carboxylic acid ethyl ester;
5-Ethyl-4-[[(1R)-1-phenylethyl]amino]pyrrolo[2,1-f][1,2,4]triazine-6-carboxylic acid ethyl ester;
5-Ethyl-4-[[2-(2-pyridinyl)ethyl]amino]pyrrolo[2,1-f][1,2,4]triazine-6-carboxylic acid ethyl ester;
4-[(4-Cyano-3-hydroxyphenyl)amino]-5-methylpyrrolo[2,1-f][1,2,4]triazine-6-carboxylic acid methyl ester;
4-[(Cyclohexylmethyl)amino]-5-ethylpyrrolo[2,1-f][1,2,4]triazine-6-carboxylic acid ethyl ester;
4-[[(4-Cyanocyclohexyl)methyl]amino]-5-ethylpyrrolo[2,1-f][1,2,4]triazine-6-carboxylic acid ethyl ester;
4-[(3-Chloro-4-fluorophenyl)amino]-5-(phenylmethyl)pyrrolo[2,1-f][1,2,4]triazine-6-carboxylic acid ethyl ester;
5-(Phenylmethyl)-4-[[1-(phenylmethyl)-1H-indazol-5-yl]amino]pyrrolo[2,1-f] [1,2,4]triazine-6-carboxylic acid ethyl ester;
4-[(3-Hydroxy-4-methylphenyl)amino]-5-(phenylmethyl)pyrrolo[2,1-f][1,2,4]triazine-6-carboxylic acid ethyl ester;
4-[[(4-Bromophenyl)methyl]amino]-5-ethylpyrrolo[2,1-f][1,2,4]triazine-6-carboxylic acid ethyl ester;
5-Ethyl-4-[(trans-4-hydroxycyclohexyl)amino]pyrrolo[2,1-f][1,2,4]triazine-6-carboxylic acid ethyl ester;
N-(3-Bromophenyl)-5-methyl-6-[3-(2H-1,2,3-triazol-2-yl)propoxy]pyrrolo[2,1-f] [1,2,4]triazin-4-amine;
N-(4-Bromo-2-fluorophenyl)-5-methyl-6-[3-(2H-1,2,3-triazol-2-yl)propoxy]pyrrolo[2, 1-f][1,2,4]triazin-4-amine;
1,3-Dihydro-3-[5-methyl-6-[3-(2H-1,2,4-triazol-2-yl)propoxy]pyrrolo[2,1 f] [1,2,4]triazin-4-yl]-2H-indol-2-one;
5-Ethyl-4-[[(1-hydroxycyclohexyl)methyl]amino]pyrrolo[2,1-f][1,2,4]triazine-6-carboxylic acid ethyl ester;
4-[[(3-Bromophenyl)methyl]amino]-5-ethylpyrrolo[2,1-f][1,2,4]triazine-6-carboxylic acid ethyl ester;
4-[[(2-Bromophenyl)methyl]amino]-5-ethylpyrrolo[2,1-f][1,2,4]triazine-6-carboxylic acid ethyl ester;
5-Ethyl-N,N-dimethyl-4-[[1-(phenylmethyl)-1H-indazol-5-yl]amino]pyrrolo[2,1-f] [1,2,4]triazine-6-carboxamide;
4-[(3-Hydroxy-4-methylphenyl)amino]-N-[3-(4-morpholinyl)propyl]-5-propylpyrrolo[2,1-f] [1,2,4]triazine-6-carboxamide;
4-[(3-Hydroxy-4-methylphenyl)amino]-5-propyl-N-[3-(1-pyrrolidinyl)propyl] pyrrolo[2,1-f][1,2,4]triazine-6-carboxamide;
N-(3-Bromophenyl)-5-methyl-6-[3-(4-morpholinyl)propyl]pyrrolo[2,1-f] [1,2,4]triazin-4-amine;
4-[(3-Chloro-4-fluorophenyl)amino]-5-[3-(phenylmethoxy)propyl]pyrrolo[2,1 f][1,2,4]triazine-6-carboxylic acid methyl ester; and
4-[[1-(Phenylmethyl)-1H-indazol-5-yl]amino]pyrrolo[2,1-f][1,2,4]triazine-6-carboxylic acid methyl ester.

What is claimed is:
1. A compound of formula I

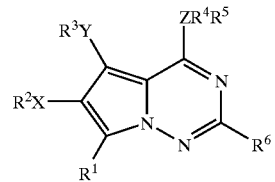

its enantiomers, diastereomers, and pharmaceutically acceptable salts, prodrugs and solvates thereof, wherein
X and Y are independently O, OCO, S, SO SO$_2$, CO, CO$_2$, NR$^{10}$, NR$^{11}$CO, NR$^{12}$CONR$^{13}$, NR$^{14}$CO$_2$, NR$^{15}$SO$_2$, NR$^{15}$SO$_2$, NR$^{16}$SO$_2$NR$^{17}$, SO$_2$NR$^{18}$, CONR$^{19}$, halogen, nitro, cyano, or X or Y are absent;

Z is O, S, N, or CR$^{20}$;

R$^1$ is hydrogen, CH$_3$, OH, OCH$_3$, SH, SCH$_3$, OCOR$^{21}$, SOR$^{22}$, SO$_2$R$^{23}$, SO$_2$NR$^{24}$R$^{25}$, CO$_2$R$^{26}$, CONR$^{27}$R$^{28}$, NH$_2$, NR$^{29}$SO$_2$NR$^{30}$R$^{31}$, NR$^{32}$SO$_2$R$^{33}$, NR$^{34}$COR$^{35}$, NR$^{36}$CO$_2$R$^{37}$, NR$^{38}$CONR$^{39}$R$^{40}$, halogen, nitro, or cyano;

R$^2$ and R$^3$ are independently hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heterocycloalkyl or substituted heterocycloalkyl, or when X is halo, nitro or cyano R$^2$ is absent or when Y is halo, nitro or cyano R$^3$ is absent;

R$^4$ is alkyl, substituted alkyl, aryl, substituted aryl, heterocyclo, substituted heterocyclo, aralkyl, substituted aralkyl;

R$^5$ is hydrogen, alkyl, substituted alkyl, aryl, substituted aryl, heterocyclo, substituted heterocyclo, aralkyl, or substituted aralkyl;

or R$^4$ and R$^5$ may together form an optionally substituted monocyclic 5–7 membered saturated or unsaturated carbocyclic or heterocyclic ring, or an optionally substituted bicyclic 7–11 membered saturated or unsaturated heterocyclic ring, except that when Z is O or S, R$^5$ is absent;

R$^6$ is hydrogen, alkyl, substituted alkyl, substituted aryl, heterocyclo, substituted heterocyclo, NR$^7$R$^8$, OR$^9$ or halogen;

R$^7$ is selected from the group consisting of hydrogen, C$_2$–C$_{20}$ alkyl, substituted alkyl, aryl, substituted aryl, heterocyclo, and substituted heterocyclo, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{21}$, R$^{24}$, R$^{25}$, R$^{26}$, R$^{27}$, R$^{28}$, R$^{29}$, R$^{30}$, R$^{31}$, R$^{32}$, R$^{34}$, R$^{35}$, R$^{36}$, R$^{38}$, R$^{39}$ and R$^{40}$ are independently selected from the group consisting of hydrogen, alkyl, substituted alkyl, aryl, substituted aryl, heterocyclo, and substituted heterocyclo, R$^{22}$, R$^{23}$, R$^{33}$ and R$^{37}$ are independently selected from the group consisting of alkyl, substituted alkyl, aryl, substituted aryl, heterocyclo, and substituted heterocyclo; and R$^{20}$ is selected from the group consisting of hydrogen, lower alkyl and substituted alkyl, or R$^{20}$ is absent if the carbon to which it is attached is part of an unsaturated aryl or heteroaryl ring;

with the provisos that:

a. R$^2$ may not be hydrogen if X is SO, SO$_2$, NR$^{13}$CO$_2$, or NR$^{14}$SO$_2$, b. R$^3$ may not be hydrogen if Y is SO, SO$_2$, NR$^{13}$ CO$_2$, or NR$^{14}$SO$_2$.

2. A compound selected from the group consisting of:

N-(4-Chlorophenyl)pyrrolo[2,1-f][1,2,4]triazin-4-amine;

2-Methyl-5-(pyrrolo[2,1-f][1,2,4]triazin-4-ylamino)phenol;

7-Bromo-N-(4-chlorophenyl)pyrrolo[2,1-f][1,2,4]triazin-4-amine;

N-(4-Chloro-2-fluorophenyl)pyrrolo[2,1-f][1,2,4}triazin-4-amine;

2-Methyl-5-[(6-methylpyrrolo[2,1-f][1,2,4]triazin-4-yl)amino]phenol;

N-(4-Bromo-2-fluorophenyl)pyrrolo[2,1-f][1,2,4]triazin-4-amine;

2-Methyl-5-[(5-methylpyrrolo[2,1-f][1,2,4]triazin-4-yl)amino]phenol;

5-[[2-(Dimethylamino)pyrrolo[2,1-f][1,2,4]triazin-4-yl]amino]-2-methylphenol;

5-[(5,7-Dimethylpyrrolo[2,1-f][1,2,4]triazin-4-yl)amino]-2-methylphenol;

5-[(6-Ethyl-5,7-dimethylpyrrolo[2,1-f][1,2,4]triazin-4-yl)amino]-2-methylphenol;

5-[(5,6-Dimethylpyrrolo[2,1-f][1,2,4]triazin-4-yl)amino]-2-methylphenol;

2-Methyl-5-[(7-methylpyrrolo[2,1-f][1,2,4}triazin-4-yl)amino]phenol;

N-(4-Bromo-2-fluorophenyl)-5-methylpyrrolo[2,1-f][1,2,4]triazin-4-amine;

N-(4-Bromo-2-fluorophenyl)-7-methylpyrrolo[2,1-f][1,2,4]triazin-4-amine;

1-[2,3-Dihydro-6-(pyrrolo[2,1-f][1,2,4]triazin-4-ylamino)-1H-indol-1-yl]ethanone;

N-(4-Bromo-2-fluorophenyl)-6-methylpyrrolo[2,1-f][1,2,4]triazin-4-amine;

5-[(5-Ethylpyrrolo[2,1-f][1,2,4]triazin-4-yl)amino]-2-methylphenol;

4-[(3-Hydroxy-4-methylphenyl)amino]-5-methylpyrrolo[2,1-f][1,2,4]triazine-6-carboxylic acid methyl ester;

4-[(3-Hydroxy-4-methylphenyl)amino]-5-methylpyrrolo[2,1-f][1,2,4]triazine-6-methanol;

4-[(3-Hydroxy-4-methylphenyl)amino]-5-methylpyrrolo[2,1-f][1,2,4]triazine-6-carboxylic acid;

1-[[4-[(3-Hydroxy-4-methylphenyl)amino]-5-methylpyrrolo[2,1-f][1,2,4]triazin-6-yl]carbonyl]4-methylpiperazine;

4-[(3-Hydroxy-4-methylphenyl)amino]-5-methyl-N-[2-(1-pyrrolidinyl)ethyl]pyrrolo[2,1-f] [1,2,4]triazine-6-carboxamide;

4-[(3-Hydroxy-4-methylphenyl)amino]-5-phenylpyrrolo[2,1-f][1,2,4]triazine-6-carboxylic acid ethyl ester;

4-[(3-Methoxy-4-methylphenyl)amino]-5-methylpyrrolo[2,1-f][1,2,4]triazine-6-carboxylic acid methyl ester;

2-Methyl-5-[5-methyl-6-(1H-1,2,4-triazol-1-ylmethyl)pyrrolo[2,1-f][1,2,4]triazin-4-yl]amino]phenol;

4-[(3-Cyanophenyl)amino]-5-methylpyrrolo[2,1-f][1,2,4}triazine-6-carboxylic acid methyl ester;

4-[(3-Carboxyphenyl)amino]-5-methylpyrrolo[2,1-fl[1,2,4]triazine-6-carboxylic acid methyl ester;

4-[3-(Acetylamino)phenyl]amino]-5-methylpyrrolo[2,1-f][1,2,4]triazine-6-carboxylic acid methyl ester;

4-[(3-Fluoro-4-methylphenyl)amino]-5-methylpyrrolo[2,1-f][1,2,4]triazine-6-carboxylic acid methyl ester;

5-Methyl-4-[(4-methyl-3-nitrophenyl)amino]pyrrolo[2,1-f][1,2,4]triazine-6-carboxylic acid methyl ester;

5-Methyl-4-[[4-methyl-3-[(methylsulfonyl)amino]phenyl]amino]pyrrolo[2,1-f] [1,2,4]triazine-6-carboxylic acid methyl ester;

4-[(3-Cyano-4-methylphenyl)amino]-5-methylpyrrolo[2,1-f][1,2,4]triazine-6-carboxylic acid methyl ester;

4-[(1-Acetyl-2,3-dihydro-1H-indol-6-yl)amino]-5-methylpyrrolo[2,1-f][1,2,4}triazine-6-carboxylic acid methyl ester;

4-(2,3-Dihydro-1H-indol-1-yl)-5-methylpyrrolo[2,1-f][1,2,4]triazine-6-carboxylic acid methyl ester;

4-[(3-Amino-4-methylphenyl)amino]-5-methylpyrrolo[2,1-f][1,2,4]triazine-6-carboxylic acid methyl ester;

4-[(4-Bromo-2-fluorophenyl)amino]-5-methylpyrrolo[2,1-f][1,2,4]triazine-6-carboxylic acid methyl ester;

4-[(2,3-Dihydro-1H-indol-6-yl)amino]-5-methylpyrrolo[2,1-f][1,2,4]triazine-6-carboxylic acid methyl ester;

5-Methyl-4-(5-quinolinylamino)pyrrolo[2,1-f][1,2,4]triazine-6-carboxylic acid methyl ester;

4-(2,3-Dihydro-2-oxo-1H-indol-3-yl)pyrrolo[2,1-f][1,2,4}triazine-6-carboxylic acid methyl ester;

4-[(3,4-Dimethylphenyl)amino]-5-methylpyrrolo[2,1-f][1,2,4]triazine-6-carboxylic acid methyl ester;

4-[[5-(Hydroxymethyl)-2-methylphenyl]amino]-5-methylpyrrolo[2,1-f][1,2,4]triazine-6-carboxylic acid methyl ester;

4-(1H-Indazol-6-ylamino)-5-methylpyrrolo[2,1-f][1,2,4]triazine-6-carboxylic acid methyl ester;

4-[(4-Bromo-3-methylphenyl)amino]-5-methylpyrrolo[2,1-f][1,2,4]triazine-6-carboxylic acid methyl ester;

4-[(4-Chloro-3-nitrophenyl)amino]-5-methylpyrrolo[2,1-f][1,2,4]triazine-6-carboxylic acid methyl ester;

4-[(2,3-Dihydro-1,4-benzodioxin-6-yl)amino]-5-methylpyrrolo[2,1-f][1,2,4}triazine-6-carboxylic acid methyl ester;

5-Methyl-4-[(5-methyl-2-pyridinyl)amino]pyrrolo[2,1-f][1,2,4]triazine-6-carboxylic acid methyl ester;

4-[(1H-Benzotriazol-5-yl)amino]-5-methylpyrrolo[2,1-f][1,2,4]triazine-6-carboxylic acid methyl ester;

5-Methyl-4-[[2-methyl-5-[(methylsulfonyl)amino]phenyl]amino]pyrrolo[2,1-f][1,2,4]triazine-6-carboxylic acid methyl ester;

4-[(1,2-Dihydro-4-methyl-2-oxo-7-quinolinyl)amino]-5-methylpyrrolo[2,1-f][1,2,4]triazine-6-carboxylic acid methyl ester;

4-[(3-Hydroxy-4-methylphenyl)methylamino]-5-methylpyrrolo[2,1-f][1,2,4}triazine-6-carboxylic acid methyl ester;

4-[(3-Hydroxyphenyl)amino]-5-methylpyrrolo[2,1-f][1,2,4]triazine-6-carboxylic acid methyl ester;

4-[[2-(Aminosulfonyl)phenyl]amino]-5-methylpyrrolo[2,1-f][1,2,4]triazine-6-carboxylic acid methyl ester;

[4-[(3-Hydroxy-4-methylphenyl)amino]-5-methylpyrrolo[2,1-f][1,2,4]triazin-6-yl]carbamic acid phenylmethyl ester;

4-(2,3-Dihydro-2-oxo-1H-indol-3-yl)-5-methylpyrrolo[2,1-f][1,2,4}triazine-6-carboxylic acid methyl ester;

4-[(3-Hydroxy-4-methoxyphenyl)amino]-5-methylpyrrolo[2,1-f][1,2,4]triazine-6-carboxylic acid methyl ester;

4-[(3-Hydroxy-2-methylphenyl)amino]-5-methylpyrrolo[2,1-f][1,2,4]triazine-6-carboxylic acid methyl ester;

4-(2-Benzothiazolylamino)-5-methylpyrrolo[2,1-f][1,2,4]triazine-6-carboxylic acid methyl ester;

4-[[3-Hydroxy-4-[(phenylsulfonyl)amino]phenyl]amino]-5-methylpyrrolo[2,1-f][1,2,4]triazine-6-carboxylic acid methyl ester;

4-[[3-(Aminosulfonyl)-4-methylphenyl]amino]-5-methylpyrrolo[2,1-f][1,2,4}triazine-6-carboxylic acid methyl ester;

4-[(2,3-Dihydro-1,3-dioxo-1H-isoindol-5-yl)amino]-5-methylpyrrolo[2,1-f][1,2,4]triazine-6-carboxylic acid methyl ester;

4-[[3-(Hydroxymethyl)phenyl]amino]-5-methylpyrrolo[2,1-f][1,2,4]triazine-6-carboxylic acid methyl ester;

4-(1H-Indol-6-ylamino)-5-methylpyrrolo[2,1-f][1,2,4}triazine-6-carboxylic acid methyl ester;

5-[(6-Amino-5-methylpyrrolo[2,1-f][1,2,4]triazin-4-yl)amino]-2-methylphenol;

4-[(3-Carboxy-4-hydroxyphenyl)amino]-5-methylpyrrolo[2,1-f][1,2,4]triazine-6-carboxylic acid methyl ester;

4-(3-Hydroxyphenoxy)-5-methylpyrrolo[2,1-f][1,2,4]triazine-6-carboxylic acid methyl ester;

5-Methyl-4-[(4-phenoxyphenyl)amino]pyrrolo[2,1-f][1,2,4]triazine-6-carboxylic acid methyl ester;

5-Methyl-4-[(1,2,3,4-tetrahydro-1,4-dioxo-6-phthalazinyl)amino]pyrrolo[2,1-f][1,2,4]triazine-6-carboxylic acid methyl ester;

4-[[3-(Hydroxysulfonyl)phenyl]amino]-5-methylpyrrolo[2,1-f][1,2,4]triazine-6-carboxylic acid methyl ester;

4-[[3-[(Butylamino)sulfonyl]phenyl]amino]-5-methylpyrrolo[2,1-f][1,2,4]triazine-6-carboxylic acid methyl ester;

4-[[3-(Aminosulfonyl)phenyl]amino]-5-methylpyrrolo[2,1-f][1,2,4]triazine-6-carboxylic acid methyl ester;

4-[(3-Hydroxy-4-methylphenyl)amino]-5-methoxypyrrolo[2,1-f][1,2,4]triazine-6-carboxylic acid ethyl ester;

4-[[3-(Hydrazinocarbonyl)phenyl]amino]-5-methylpyrrolo[2,1-f][1,2,4]triazine-6-carboxylic acid methyl ester;

5-Methyl-4-[[3-[(methylsulfonyl)amino]phenyl]amino]pyrrolo[2,1-f][1,2,4]triazine-6-carboxylic acid methyl ester;

5-Ethyl-4-[(3-hydroxy-4-methylphenyl)amino]pyrrolo[2,1-f][1,2,4]triazine-6-carboxylic acid ethyl ester;

5-Ethyl-4-[(6-methoxy-3-pyridinyl)amino]pyrrolo[2,1-f][1,2,4}triazine-6-carboxylic acid ethyl ester;

4-(2,3-Dihydro-2-oxo-1H-indol-3-yl)-5-ethylpyrrolo[2,1-f][1,2,4]triazine-6-carboxylic acid ethyl ester;

4-[(4-Bromo-2-fluorophenyl)amino]-5-methoxypyrrolo[2,1-f][1,2,4]triazine-6-carboxylic acid ethyl ester;

4-[(4-Bromo-2-fluorophenyl)amino]-5-methoxy-N-[2-(1-pyrrolidinyl)ethyl]pyrrolo[2,1-f] [1,2,4]triazine-6-carboxamide;

4-[(4-Bromo-2-fluorophenyl)amino]-5-methoxy-N-methyl-N-[2-(1-pyrrolidinyl) ethyl]pyrrolo[2,1-f][1,2,4]triazine-6-carboxamide;

4-[(6-Methoxy-3-pyridinyl)amino]-5-methylpyrrolo[2,1-f][1,2,4]triazine-6-carboxylic acid methyl ester;

4-(2,3-Dihydro-2-oxo-1H-indol-3-yl)-5-methoxypyrrolo[2,1-f][1,2,4]triazine-6-carboxylic acid ethyl ester;

5-Methoxy-4-[(6-methoxy-3-pyridinyl)amino]pyrrolo[2,1-f][1,2,4]triazine-6-carboxylic acid ethyl ester;

5-Ethyl-4-[(4-methoxyphenyl)amino]pyrrolo[2,1-f][1,2,4]triazine-6-carboxylic acid ethyl ester;

4-[(3-Amino-4-methylphenyl)amino]-5-ethylpyrrolo[2,1-f][1,2,4]triazine-6-carboxylic acid ethyl ester;

4-[(3-Hydroxy-4-methylphenyl)amino]pyrrolo[2,1-fl[1,2,4]triazine-5,6-dicarboxylic acid diethyl ester;

5-Ethyl-4-[[4-methyl-3-[(methylsulfonyl)amino]phenyl]amino]pyrrolo[2,1-f][1,2,4]triazine-6-carboxylic acid ethyl ester;

5-Ethyl-4-[(6-methoxy-3-pyridinyl)amino]pyrrolo[2,1-f][1,2,4]triazine-6-carboxylic acid;

5-Ethyl-4-[(6-methoxy-3-pyridinyl)amino]pyrrolo[2,1-f][1,2,4]triazine-6-carboxylic acid methyl ester;

4-(2,3-Dihydro-2-oxo-1H-benzimidazol-1-yl)-5-methylpyrrolo[2,1-fl[1,2,4]triazine-6-carboxylic acid methyl ester;

5-Methyl-4-(1,2,3,4-tetrahydro-3-oxo-1-quinoxalinyl)pyrrolo[2,1-f][1,2,4]triazine-6-carboxylic acid methyl ester;

5-Methyl-4-[[1-(phenylmethyl)-1H-indazol-5-yl]amino]pyrrolo[2,1-f][1,2,4]triazine-6-carboxylic acid methyl ester;

4-[[6-(Acetylamino)-3-pyridinyl]amino]-5-methylpyrrolo[2,1-f][1,2,4]triazine-6-carboxylic acid methyl ester;

5-Ethyl-4-[(6-methoxy-3-pyridinyl)amino]-N-[2-(1-pyrrolidinyl)ethyl]pyrrolo[2,1-f] [1,2,4]triazine-6-carboxamide;

5-Ethyl-4-[(6-methoxy-3-pyridinyl)amino]-N-methyl-N-[2-(1-pyrrolidinyl)ethyl]pyrrolo[2,1 f] [1,2,4]triazine-6-carboxamide;

4-[(6-Chloro-3-pyridinyl)amino]-5-ethylpyrrolo[2,1-f][1,2,4]triazine-6-carboxylic acid ethyl ester;

5-Ethyl-4-(1H-indazol-6-ylamino)pyrrolo[2,1-f][1,2,4]triazine-6-carboxylic acid ethyl ester;

4-[(6-Methoxy-3-pyridinyl)amino]-5-methylpyrrolo[2,1-f][1,2,4]triazine-6-carboxylic acid ethyl ester;

[4-[(6-Methoxy-3-pyridinyl)amino]-5-ethylpyrrolo[2,1-f][1,2,4]triazin-6-yl]carbamic acid phenylmethyl ester;

4-(2,3-Dihydro-2-oxo-1H-indol-3-yl)-5-methylpyrrolo[2,1-f][1,2,4]triazine-6-carboxylic acid;

4-Hydroxy-5-methoxypyrrolo[2,1-f][1,2,4]triazine-6-carboxylic acid ethyl ester;

4-[2,3-Dihydro-5-[(methylsulfonyl)amino]-2-oxo-1H-indol-3-yl]-5-methylpyrrolo[2,1-f] [1,2,4]triazine-6-carboxylic acid methyl ester;

5-Ethyl-4-[(4-hydroxyphenyl)amino]pyrrolo[2,1-f][1,2,4]triazine-6-carboxylic acid ethyl ester;

4-(2,3-Dihydro-2-oxo-1H-indol-3-yl)pyrrolo[2,1-f][1,2,4]triazine-6-carboxylic acid methyl ester;

5-Methyl-4-(1H-pyrazol-3-ylamino)pyrrolo[2,1-f][1,2,4]triazine-6-carboxylic acid methyl ester;

4-[(4-Methoxyphenyl)amino]-5-methylpyrrolo[2,1-f][1,2,4]triazine-6-carboxylic acid methyl ester;

4-[(3,4-Dimethoxyphenyl)amino]-5-methylpyrrolo[2,1-f][1,2,4]triazine-6-carboxylic acid methyl ester;

5-Methyl-4-[(5-methyl-1H-pyrazol-3-yl)amino]pyrrolo[2,1-f][1,2,4]triazine-6-carboxylic acid methyl ester;

4-(2,3-Dihydro-3-oxo-1H-indazol-2-yl)-5-methylpyrrolo[2,1-f][1,2,4]triazine-6-carboxylic acid methyl ester;

4-(2,3-Dihydro-3-oxo-1H-indazol-1-yl)-5-methylpyrrolo[2,1-f][1,2,4]triazine-6-carboxylic acid methyl ester;

4-[6-Fluoro-2-hydroxy-1H-indol-3-yl]-5-methylpyrrolo[2,1-f][1,2,4]triazine-6-carboxylic acid methyl ester;

4-[6-Bromo-2-hydroxy-1H-indol-3-yl]-5-methylpyrrolo[2,1-f][1,2,4]triazine-6-carboxylic acid methyl ester;

4-[5-(Aminosulfonyl)-2,3-dihydro-2-oxo-1H-indol-3-yl]-5-methylpyrrolo[2,1-f][1,2,4]triazine-6-carboxylic acid methyl ester;

4-[2,3-Dihydro-5-[[[2-(4-morpholinyl)ethyl]amino]sulfonyl]-2-oxo-1H-indol-3-yl]-5-methylpyrrolo[2,1-f] [1,2,4]triazine-6-carboxylic acid methyl ester;

4-[2,3-Dihydro-2-oxo-5-[[[2-(1-pyrrolidinyl)ethyl]amino]sulfonyl]-1H-indol-3-yl]-5-methylpyrrolo[2,1-f][1,2,4]triazine-6-carboxylic acid methyl ester;

4-(5-Fluoro-2,3-dihydro-2-oxo-1H-indol-3-yl)-5-methylpyrrolo[2,1-f][1,2,4]triazine-6-carboxylic acid methyl ester;

4-[2,3-Dihydro-2-oxo-6-(trifluoromethyl)-1H-indol-3-yl]-5-methylpyrrolo[2,1-f][1,2,4]triazine-6-carboxylic acid methyl ester;

4-(2,3-Dihydro-2-oxo-1H-indol-3-yl)pyrrolo[2,1-f][1,2,4]triazine-5,6-dicarboxylic acid diethyl ester;

4-[2,3-Dihydro-6-(methylsulfonyl)-2-oxo-1H-indol-3-yl]-5-methylpyrrolo[2,1-f][1,2,4]triazine-6-carboxylic acid methyl ester;

4-[5-[(Dimethylamino)sulfonyl]-2,3-dihydro-2-oxo-1H-indol-3-yl]-5-methylpyrrolo[2,1-f] [1,2,4]triazine-6-carboxylic acid methyl ester;

4-[5-(Aminocarbonyl)-2,3-dihydro-2-oxo-1H-indol-3-yl]-5-methylpyrrolo[2,1-f][1,2,4]triazine-6-carboxylic acid methyl ester;

[4-(2,3-Dihydro-2-oxo-1H-indol-3-yl)-5-methylpyrrolo[2,1-f][1,2,4]triazin-6-yl]carbamic acid phenylmethyl ester;

4-(5-Cyano-2,3-dihydro-2-oxo-1H-indol-3-yl)-5-methylpyrrolo[2,1-f][1,2,4]triazine-6-carboxylic acid methyl ester;

4-(2,3-Dihydro-6-methyl-2-oxo-1H-pyrazolo[2,3-d]pyrimidin-3-yl)-5-methylpyrrolo[2,1-f] [1,2,4]triazine-6-carboxylic acid methyl ester;

4-(2,3-Dihydro-2-oxo-1H-pyrazolo[2,3-b]pyridin-3-yl)-5-methylpyrrolo[2,1-f][1,2,4]triazine-6-carboxylic acid methyl ester;

4-(2,3-Dihydro-2-oxo-1H-indol-3-yl)-N,5-dimethyl-N-[2-(1-pyrrolidinyl)ethyl]pyrrolo [2,1-f][1,2,4]triazine-6-carboxamide;

4-(2,3-Dihydro-2-oxo-1H-indol-3-yl)-5-methyl-N-[2-(1-pyrrolidinyl)ethyl]pyrrolo[2,1-f] [1,2,4]triazine-6-carboxamide;

4-(2,3-Dihydro-2-oxo-1H-indol-3-yl)-5-methyl-N-[3-(4-morpholinyl)propyl]pyrrolo[2,1-f] [1,2,4]triazine-6-carboxamide;

4-(2,3-Dihydro-2-oxo-1H-indol-3-yl)-5-methyl-N-[2-(4-morpholinyl)ethyl]pyrrolo[2,1-f] [1,2,4]triazine-6-carboxamide;

4-(2,3-Dihydro-2-oxo-1H-indol-3-yl)-N-[[[3-(dimethylamino)propyl]amino]carbonyl]-N-ethyl-5-methylpyrrolo[2,1-f][1,2,4}triazine-6-carboxamide;

4-[2,3-Dihydro-5-[[(2-hydroxyethyl)amino]sulfonyl]-2-oxo-1H-indol-3-yl]-5-methylpyrrolo[2,1 f][1,2,4]triazine-6-carboxylic acid methyl ester;

4-[2,3-Dihydro-5-(4-morpholinylsulfonyl)-2-oxo-1H-indol-3-yl]-5-methylpyrrolo[2,1-f] [1,2,4]triazine-6-carboxylic acid methyl ester;

4-[2,3-Dihydro-5-[(methylamino)sulfonyl]-2-OxO-1H-indol-3-yl]-5-methylpyrrolo[2,1-f] [1,2,4]triazine-6-carboxylic acid methyl ester;

4-[(3-Bromophenyl)amino]-5-ethylpyrrolo[2,1-f[1,2,4]triazine-6-carboxylic acid ethyl ester;

5-Ethyl-4-[(4-phenoxyphenyl)amino]pyrrolo[2,1-f][1,2,4]triazine-6-carboxylic acid ethyl ester;

5-Ethyl-4-[[1-(phenylmethyl)-1H-indazol-4-yl]amino]pyrrolo[2,1-f][1,2,4]triazine-6-carboxylic acid ethyl ester;

4-(6-Cyano-2,3-dihydro-2-oxo-1H-indol-3-yl)-5-methylpyrrolo[2,1-f][1,2,4]triazine-6-carboxylic acid methyl ester;

4-(2,5-Dihydro-3-methyl-5-oxo-1H-pyrazol-1-yl)-5-methylpyrrolo[2,1-f][1,2,4]triazine-6-carboxylic acid methyl ester;

3-(6-Amino-5-methylpyrrolo[2,1-f][1,2,4]triazin-4-yl)-1,3-dihydro-2H-indol-2-one;

3-(6-Amino-5-methylpyrrolo[2,1-f][1,2,4]triazin-4-yl)-1,3-dihydro-2H-indol-2-one;

4-[(3-Hydroxy-4-methylphenyl)amino]-5-methyl-N-[3-(4-morpholinyl)propyl]pyrrolo [2,1-f][1,2,4]triazine-6-carboxamide;

N-[4-(2,3-Dihydro-2-oxo-1H-indol-3-yl)-5-methylpyrrolo[2,1-f][1,2,4]triazin-6-yl]-N'-[2-(4-morpholinyl)ethyl] urea;

N-[4-(2,3-Dihydro-2-oxo-1H-indol-3-yl)-5-methylpyrrolo[2,1-f][1,2,4]triazin-6-yl]-N'-[3-(4-morpholinyl)propyl] urea;

N-[4-(2,3-Dihydro-2-oxo-1H-indol-3-yl)-5-methylpyrrolo[2,1-f][1,2,4]triazin-6-yl]-N'-[4-(4-morpholinyl)butyl] urea;

5-Ethyl-4-[[1-(phenylmethyl)-1H-indazol-5-yl]amino]pyrrolo[2,1-f][1,2,4]triazine-6-methanol;

4-(2,3-Dihydro-1-methyl-2-oxo-1H-indol-3-yl)-5-methylpyrrolo[2,1-f][1,2,4]triazine-6-carboxylic acid methyl ester;

5-Ethyl-4-[(6-methoxy-3-pyridinyl)amino]-N-[2-(1-pyrrolidinyl)ethyl]pyrrolo[2,1-f] [1,2,4]triazine-6-carboxamide;

5-Ethyl-4-[(6-methoxy-3-pyridinyl)amino]-N-methyl-N-[2-(1-pyrrolidinyl)ethyl]pyrrolo [2,1-f][1,2,4]triazine-6-carboxamide;

5-Ethyl-N-[3-(1H-imidazol-1-yl)propyl]-4-[[1-(phenylmethyl)-1H-indazol-5-yl]amino]pyrrolo[2,1-f] [1,2,4]triazine-6-carboxamide;

4-(2,3-Dihydro-2-oxo-1H-indol-3-yl)-5-methyl-N-[3-(1-pyrrolidinyl)propyl]pyrrolo[2,1-f] [1,2,4]triazine-6-carboxamide;

4-(2,3-Dihydro-2-oxo-1H-indol-3-yl)-5-methyl-N-[3-(4-methyl-1-piperazinyl)propyl] pyrrolo[2,1-f][1,2,4]triazine-6-carboxamide;

4-(2,3-Dihydro-2-oxo-1H-indol-3-yl)-5-methyl-N-[3-(1H-1,2,3-triazol-1-yl)propyl]pyrrolo[2,1 f] [1,2,4]triazine-6-carboxamide;

4-(2,3-Dihydro-2-oxo-1H-indol-3-yl)-5-methyl-N-[3-(2H-1,2,3-triazol-2-yl)propyl]pyrrolo[2,1 f] [1,2,4}triazine-6-carboxamide;

4-(2,3-Dihydro-2-oxo-1H-indol-3-yl)-5-methyl-N-[3-(1H-1,2,4-triazol-1-yl) propyl]pyrrolo[2,1 f] [1,2,4]triazine-6-carboxamide;

4-(2,3-Dihydro-2-oxo-1H-indol-3-yl)-5-methyl-N-[3-(2-methyl-1H-imidazol-1-yl) propyl]pyrrolo[2,1-f][1,2,4]triazine-6-carboxamide;

4-(2,3-Dihydro-2-oxo-1H-indol-3-yl)-5-methyl-N-[4-(4-morpholinyl)butyl]pyrrolo[2,1-f] [1,2,4]triazine-6-carboxamide;

4-(2,3-Dihydro-2-oxo-1H-indol-3-yl)-N,5-dimethyl-N-[3-(4-morpholinyl)propyl]pyrrolo [2,1-f][1,2,4]triazine-6-carboxamide;

4-(6-Fluoro-2,3-dihydro-2-oxo-1H-indol-3-yl)-5-methyl-N-[3-(4-morpholinyl) propyl]pyrrolo[2,1-f][1,2,4]triazine-6-carboxamide;

5-Ethyl-N-[2-(4-morpholinyl)ethyl]-4-[[1-(phenylmethyl)-1H-indazol-5-yl]amino]pyrrolo[2,1 f] [1,2,4]triazine-6-carboxamide;

5-Ethyl-N-[6-[3-(1H-imidazol-1-yl)propyl]-2-pyridinyl]-4-[[1-(phenylmethyl)-1H-indazol-5-yl] amino}pyrrolo[2,1-f][1,2,4]triazine-6-carboxamide;

4-(5-Fluoro-2,3-dihydro-2-oxo-1H-indol-3-yl)-5-methyl-N-[3-(4-morpholinyl)propyl] pyrrolo[2,1-f][1,2,4]triazine-6-carboxamide;

4-(3-Hydroxy-4-methoxyphenyl)-5-methyl-N-[3-(4-morpholinyl)propyl]pyrrolo[2,1-f] [1,2,4]triazine-6-carboxamide;

7-Bromo-5-ethyl-4-[[1-(phenylmethyl)-1H-indazol-5-yl]amino]pyrrolo[2,1-f][1,2,4]triazine-6-carboxylic acid ethyl ester;

7-Bromo-5-ethyl-4-[[1-(phenylmethyl)-1H-indazol-5-yl]amino]pyrrolo[2,1-f][1,2,4]triazine-6-methanol;

N-[4-(2,3-Dihydro-2-oxo-1H-indol-3-yl)-5-methylpyrrolo[2,1-f][1,2,4]triazin-6-yl]-4-morpholinebutanamide;

5-Ethyl-6-[[2-4(4-morpholinyl)ethyoxy]methyl]-N-[1-(phenylmethyl)-1H-indazol-5-yl]pyrrolo[2,1-f] [1,2,4]triazin-4-amine;

7-Bromo-5-ethyl-N-[2-(4-morpholinyl)ethyl]-4-[[1-(phenylmethyl)-1H-indazol-5-yl]amino]pyrrolo[2,1-f] [1,2,4]triazine-6-carboxamide;

4-(2,3-Dihydro-2-oxo-1H-indol-3-yl)-5-methylpyrrolo[2,1-f][1,2,4]triazine-6-carboxamide;

4-(2,3-Dihydro-2-oxo-1H-indol-3-yl)-N,5-dimethylpyrrolo[2,1-f][1,2,4]triazine-6-carboxamide;

4-(2,3-Dihydro-2-oxo-1H-indol-3-yl)-5-methoxy-N-[3-(1H-1,2,4-triazol-1-yl)propyl]pyrrolo[2,1-f] [1,2,4}triazine-6-carboxamide;

4-(2,3-Dihydro-2-oxo-1H-indol-3-yl)-5-methoxy-N-[3-(4-morpholinyl)propyl]pyrrolo [2,1-f][1,2,4]triazine-6-carboxamide;

4-[(4-Bromophenyl)amino]-5-methyl-N-[3-(4-morpholinyl)propyl]pyrrolo[2,1-f] [1,2,4]triazine-6-carboxamide;

N-[4-(2,3-Dihydro-2-oxo-1H-indol-3-yl)-5-methylpyrrolo[2,1-f][1,2,4]triazin-6-yl]-2-methylpropanamide;

3-[6-(Dimethylamino)-7-(hydroxymethyl)-5-methylpyrrolo[2,1-f][1,2,4]triazin-4-yl]1,3-dihydro-2H-indol-2-one;

N-[4-(2,3-Dihydro-2-oxo-1H-indol-3-yl)-5-methylpyrrolo[2,1-f][1,2,4]triazin-6-yl]methanesulfonamide;

3-(5,6-Dimethoxypyrrolo[2,1-f][1,2,4]triazin-4-yl)-1,3-dihydro-2H-indol-2-one; N-[4-(2,3-Dihydro-2-oxo-1H-indol-3-yl)-5-methylpyrrolo[2,1-f][1,2,4]triazin-6-yl]-4-morpholinepropanesulfonamide;

[4-(2,3-Dihydro-2-oxo-1H-indol-3-yl)-5-methoxypyrrolo[2,1-f][1,2,4]triazin-6-yl}carbamic acid phenylmethyl ester;

4-[5-(Aminosulfonyl)-2,3-dihydro-2-oxo-1H-indol-3-yl]-5-methyl-N-[3-(4-morpholinyl)propyl]pyrrolo[2,1-f][1,2,4]triazine-6-carboxamide;

1,3-Dihydro-3-[5-methoxy-6-[[4-(4-methyl-1-piperazinyl)butyl]amino]pyrrolo[2,1-f] [1,2,4]triazin-4-yl]-2H-indol-2-one;

3-(6-Amino-5-methoxypyrrolo[2,1-f][1,2,4]triazin-4-yl)-1,3-dihydro-2H-indol-2-one;

1,3-Dihydro-3-[5-methoxy-6-[[4-(4-morpholinyl)butyl]amino]pyrrolo[2,1-f][1,2,4}triazin-4-yl]-2H-indol-2-one;

4-[(3-Hydroxy-5-methylphenyl)amino]-5-methylpyrrolo[2,1-f][1,2,4]triazine-6-carboxylic acid methyl ester;

4-[(4-Ethyl-3-hydroxyphenyl)amino]-5-methylpyrrolo[2,1-f][1,2,4]triazine-6-carboxylic acid methyl ester;

1,3-Dihydro-3-[5-methyl-6-[2-(1H-1,2,4-triazol-1-yl)ethoxy]pyrrolo[2,1-f][1,2,4]triazin-4-yl]-2H-indol-2-one;

5-[(5,6-Dimethoxypyrrolo[2,1-f][1,2,4]triazin-4-yl)amino]-2-methylphenol;

4-[(4-Bromo-3-hydroxyphenyl)amino]-5-methylpyrrolo[2,1-f][1,2,4]triazine-6-carboxylic acid methyl ester;

4-[[3-Hydroxy-4-(1-methylethyl)phenyl]amino]-5-methylpyrrolo[2,1-f][1,2,4]triazine-6-carboxylic acid methyl ester;

4-(2,3-Dihydro-2-oxo-1H-indol-3-yl)-5-methylpyrrolo[2,1-f][1,2,4]triazine-6-propanoic acid methyl ester;

4-[(4-Hydroxy-2-naphthalenyl)amino]-5-methylpyrrolo[2,1-f][1,2,4]triazine-6-carboxylic acid methyl ester;

4-[(4-Carboxy-3-hydroxyphenyl)amino]-5-methylpyrrolo[2,1-f][1,2,4]triazine-6-carboxylic acid methyl ester;

4-[(3-Chloro-4-fluorophenyl)amino]-5-methylpyrrolo[2,1-f][1,2,4]triazine-6-carboxylic acid methyl ester;

4-[(3-Chloro-4-fluorophenyl)amino]-5-ethylpyrrolo[2,1-f][1,2,4]tnazine-6-carboxylic acid ethyl ester;

1,3-Dihydro-3-(6-methoxy-5-methylpyrrolo[2,1-f][1,2,4]triazin-4-yl)-2H-indol-2-one;

4-[(3-Chloro-4-fluorophenyl)amino]pyrrolo[2,1-f][1,2,4]triazine-6-carboxylic acid methyl ester;

4-[3-[4-(2,3-Dihydro-2-oxo-1H-indol-3-yl)-5-methylpyrrolo[2,1-f][1,2,4}triazin-6-yl]-1-oxopropyl]morpholine;

1-[3-[4-(2,3-Dihydro-2-oxo-1H-indol-3-yl)-5-methylpyrrolo[2,1-f][1,2,4]triazin-6-yl]-1 oxopropyl]-4-methylpiperazine;

4-[[1-(Phenylmethyl)-1H-indazol-5-yl]amino]-5-ethylpyrrolo[2,1-f][1,2,4]triazine-6-carboxylic acid ethyl ester;

4-[[1-(Phenylmethyl)-1H-indazol-5-yl]amino]-5-propylpyrrolo[2,1-f][1,2,4]triazine-6-carboxylic acid ethyl ester;

4-[(4-Bromophenyl)amino]-5-ethylpyrrolo[2,1-f][1,2,4]triazine-6-carboxylic acid ethyl ester;

4-(2,3-Dihydro-2-oxo-1H-indol-3-yl)-5,6-dimethoxypyrrolo[2,1-f][,1,2,4]triazine-7-carboxylic acid methyl ester;

4-[(4-Butyl-3-hydroxyphenyl)amino]-5-methylpyrrolo[2,1-f][1,2,4]triazine-6-carboxylic acid methyl ester;

4-[(3-Hydroxy-4-propylphenyl)amino]-5-methylpyrrolo[2,1-f][1,2,4]triazine-6-carboxylic acid methyl ester;

4-[(3-Hydroxy-4-methylphenyl)amino]-5-propylpyrrolo[2,1-f][1,2,4]triazine-6-carboxylic acid ethyl ester;

4-(2,3-Dihydro-2-oxo-1H-indol-3-yl)-N-(2-methoxyethyl)-5-methylpyrrolo[2,1-f] [1,2,4]triazine-6-carboxamide;

4-(2,3-Dihydro-2-oxo-1H-indol-3-yl)-N-(3-methoxypropyl)-5-methylpyrrolo[2,1-f] [1,2,4]triazine-6-carboxamide;

4-(2,3-Dihydro-2-oxo-1H-indol-3-yl)-5-methyl-N-[(tetrahydro-2-furanyl)methyl]pyrrolo[2,1 f] [1,2,4]triazine-6-carboxamide;

5-Ethoxy-4-[(3-hydroxy-4-methylphenyl)amino}pyrrolo[2,1-f][1,2,4]triazine-6-carboxylic acid ethyl ester;

4-[(4-Ethyl-3-hydroxyphenyl)amino]-5-methyl-N-[3-(4-morpholinyl)propyl]pyrrolo[2,1-f] [1,2,4]triazine-6-carboxamide;

4-[(4-Bromo-3-hydroxyphenyl)amino]-5-methyl-N-[3-(4-morpholinyl)propyl]pyrrolo[2,1 f] [1,2,4]triazine-6-carboxamide;

4-[(3-Hydroxy-4-methylphenyl)amino]-5-methyl-N-[3-(2H-1,2,3-triazol-2-yl)propyl] pyrrolo[2,1-f][1,2,4]triazine-6-carboxamide;

5-Ethyl-4-(phenylamino)pyrrolo[2,1-f][1,2,4]triazine-6-carboxylic acid ethyl ester;

5-Ethyl-4-(methylphenylamino)pyrrolo[2,1-f][1,2,4]triazine-6-carboxylic acid ethyl ester;

5-Ethyl-4-(1,2,3,4-tetrahydro-2-isoquinolinyl)pyrrolo[2,1-f][1,2,4]triazine-6-carboxylic acid ethyl ester;

4-[(3-Hydroxy-4-methylphenyl)amino]-N-(3-methoxypropyl)-5-methylpyrrolo[2,1-f] [1,2,4]triazine-6-carboxamide;

4-[(3-Hydroxy-4-methylphenyl)amino]-5-methyl-N-[3-(4-methyl-1-piperazinyl) propyl]pyrrolo[2,1-f][1,2,4]triazine-6-carboxamide;

4-[(3-Hydroxy-4-methylphenyl)amino]-N,5-dimethylpyrrolo[2,1-f][1,2,4]triazine-6-carboxamide;

N-[2-(Dimethylamino)ethyl]-4-[(3-hydroxy-4-methylphenyl)amino]-5-methylpyrrolo[2,1 f] [1,2,4]triazine-6-carboxamide;

5-Ethyl-4-(1,2,3,4-tetrahydro-1-quinolinyl)pyrrolo[2,1-f][1,2,4]triazine-6-carboxylic acid ethyl ester;

5-Ethyl-4-[(phenylmethyl)amino]pyrrolo[2,1-f][1,2,4]triazine-6-carboxylic acid ethyl ester;

4-(2,3-Dihydro-2-oxo-1H-indol-3-yl)-5-ethoxypyrrolo[2,1-f][1,2,4]triazine-6-carboxylic acid ethyl ester;

4-[(3-Hydroxy-4-methylphenyl)amino]-5-methyl-N-[3-(1-pyrrolidinyl)propyl]pyrrolo[2,1-f] [1,2,4]triazine-6-carboxamide;

5-Ethyl-4-(2-phenyl ethyl)amino]pyrrolo[2,1-f][1,2,4]triazine-6-carboxylic acid ethyl ester;

N-[4-(Dimethylamino)butyl]-4-[(3-hydroxy-4-methylphenyl)amino]-5-methylpyrrolo[2, 1-f][1,2,4]triazine-6-carboxamide;

4-[(3-Hydroxy-4-methylphenyl)amino]-5-(1-methylethyl)pyrrolo[2,1-f][1,2,4]triazine-6-carboxylic acid ethyl ester;

4-[(3-Hydroxy-4-methylphenyl)amino]-5-methyl-N-13-(methylsulfonyl)propyl]pyrrolo[2, 1-fi[1,2,4]triazine-6-carboxamide;

4-[(3-Chloro-4-fluorophenyl)methyl]-5-(1-methylethyl)pyrrolo[2,1-fl[1,2,4]triazine-6-carboxylic acid ethyl ester;

[4-[(3-Chloro-4-fluorophenyl)amino]-5-ethylpyrrolo[2,1-f][1,2,4]triazin-6-yl]carbamic acid phenylmethyl ester;

5-(1-Methylethyl)-4-[[1-(phenylmethyl)-1H-indazol-5-yl]amino]pyrrolo[2,1-f] [1,2,4]triazine-6-carboxylic acid ethyl ester;

4-(Butylamino)-5-ethylpyrrolo[2,1-fi][1,2,4]triazine-6-carboxylic acid ethyl ester;

5-Ethyl-4-1(2-methoxyethyl)amino]pyrrolo[2,1-f][1,2,4]triazine-6-carboxylic acid ethyl ester;

5-Ethyl-4-(4-morpholinyl)pyrrolo[2,1-fi[1,2,4]triazine-6-carboxylic acid ethyl ester;

5-Ethyl-4-[13-(1H-imidazol-1-yl)propyl]amino]pyrrolo[2,1-f][1,2,4}triazine-6-carboxylic acid ethyl ester;

2-Methyl-5-[[5-methyl-6-[3-(2H-1,2,3-triazol-2-yl)propoxy]pyrrolo[2,1-f][1,2,4]triazin-4-yl] amino]phenol;

1,3-Dihydro-3-[5-methyoxy-6-(phenylmethoxy)pyrrolo[2,1-f][1,2,4]triazin-4-yl]-2H-indol-2-one;

5-Ethyl-4-[[(1S)-1-phenylethyl]amino]pyrrolo[2,1-f][1,2,4]triazine-6-carboxylic acid ethyl ester;

5-Ethyl-4-[[(1R)-1-phenylethyl]amino]pyrrolo[2,1-f][1,2,4]triazine-6-carboxylic acid ethyl ester;

5-Ethyl-4-[[2-(2-pyridinyl)ethyl]amino]pyrrolo[2,1-f][1,2,4]triazine-6-carboxylic acid ethyl ester;

4-[(4-Cyano-3-hydroxyphenyl)amino]-5-methylpyrrolo[2,1-f]1,2,4]triazine-6-carboxylic acid methyl ester;

4-[(Cyclohexylmethyl)amino]-5-ethylpyrrolo[2,1-f][1,2,4]triazine-6-carboxylic acid ethyl ester;

4-[[(4-Cyanocyclohexyl)methyl]amino]-5-ethylpyrrolo[2,1-f][1,2,4]triazine-6-carboxylic acid ethyl ester;

4-[(3-Chloro-4-fluorophenyl)amino]-5-(phenylmethyl)pyrrolo[2,1-f][1,2,4]triazine-6-carboxylic acid ethyl ester;

5-(Phenylmethyl)-4-[[1-(phenylmethyl)-1H-indazol-5-yl]amino]pyrrolo[2,1-f] [1,2,4]triazine-6-carboxylic acid ethyl ester;

4-[(3-Hydroxy-4-methylphenyl)amino]-5-(phenylmethyl)pyrrolo[2,1-f][1,2,4}triazine-6-carboxylic acid ethyl ester;

4-1[(4-Bromophenyl)methyl]amino]-5-ethylpyrrolo[2,1-f][1,2,4]triazine-6-carboxylic acid ethyl ester;

5-Ethyl-4-[(trans-4-hydroxycyclohexyl)amino]pyrrolo[2,1-f][1,2,4]triazine-6-carboxylic acid ethyl ester;

N-(3-Bromophenyl)-5-methyl-6-[3-(2H-1,2,3-triazol-2-yl)propoxy]pyrrolo[2,1-f][1,2,4]triazin-4-amine;

N-(4-Bromo-2-fluorophenyl)-5-methyl-6-[3-(2H-1,2,3-triazol-2-yl)propoxy]pyrrolo[2,1-f] [1,2,4]triazin-4-amine;

1,3-Dihydro-3-[5-methyl-6-[3-(2H-1,2,4-triazol-2-yl)propoxy]pyrrolo[2,1-f][1,2,4]triazin-4-yl]2H-indol-2-one;

5-Ethyl-4-[[(1-hydroxycyclohexyl)methyl]amino]pyrrolo[2,1-f][1,2,4]triazine-6-carboxylic acid ethyl ester;

4-[[(3-Bromophenyl)methyl]amino]-5-ethyl pyrrolo[2,1-f][1,2,4]triazine-6-carboxylic acid ethyl ester;

4-[[(2-Bromophenyl)methyl]amino]-5-ethylpyrrolo[2,1-f][1,2,4]triazine-6-carboxylic acid ethyl ester;

5-Ethyl-N,N-dimethyl-4-[[1-(phenylmethyl)-1H-indazol-5-yl]amino]pyrrolo[2,1-f] [1,2,4}triazine-6-carboxamide;

4-[(3-Hydroxy-4-methylphenyl)amino]-N-[3-(4-morpholinyl)propyll-5-propylpyrrolo[2,1-f] [1,2,4]triazine-6-carboxamide;

4-[(3-Hydroxy-4-methylphenyl)amino]-5-propyl-N-[3-(1-pyrrolidinyl)propyl}pyrrolo[2,1-f] [1,2,4]triazine-6-carboxamide;

N-(3-Bromophenyl)-5-methyl-6-[3-(4-morpholinyl)propyl]pyrrolo[2,1-f][1,2,4]triazin-4-amine;

4-(3-Chloro-4-fluorophenyl)amino]-5-[3-(phenylmethoxy)propyl]pyrrol o[2,1-f][1,2,4]triazine-6-carboxylic acid methyl ester; and 4-[[1-(Phenylmethyl)-1H-indazol-5-yl]amino]pyrrolo[2, 1-f][1,2,4]triazine-6-carboxylic acid methyl ester; and pharmaceutically acceptable salts thereof.

3. A pharmaceutical composition comprising a compound of claim 1 and a pharmaceutically acceptable carrier.

4. A pharmaceutical composition comprising a compound of claim 1 a compound of formula I

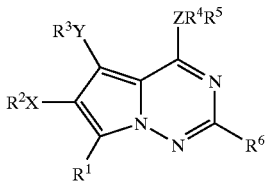

its enantiomers, diastereomers, and pharmaceutically acceptable salts, prodrugs and solvates thereof, wherein X and Y are independently O, OCO, S, SO, $SO_2$, CO, $CO_2$, $NR^{10}$, $NR^{11}CO$, $NR^{12}CONR^{13}$, $NR^{14}CO_2$, $NR^{15}SO_2$, $NR^{16}SO_2NR^{17}$, $SO_2NR^{18}$, $CONR^{19}$, halogen, nitro, cyano, or X or Y are absent;

Z is O, S, N, or $CR^{20}$, $R^1$ is hydrogen, $CH_3$, OH, $OCH_3$, SH, $SCH_3$, $OCOR^{21}$, $SOR^{22}$, $SO_2 R^{23}$, $SO_2NR^{24}R^{25}$, $CO_2R^{26}$, $CONR^{27}R^{28}$, $NH_2$, $NR^{29}SO_2NR^{30}R^{31}$, $NR^{32} SO_2R^{33}$, $NR^{34}COR^{35}$, $NR^{36}CO_2R^{37}$, $NR^{38}CONR^{39}R^{40}$, halogen, nitro, or cyano;

$R^2$ and $R^3$ are independently hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heterocycloalkyl or substituted heterocycloalkyl, or when X is halo, nitro or cyano $R^2$ is absent or when Y is halo, nitro or cyano $R^3$ is absent;

$R^4$ and $R^5$ are independently hydrogen, alkyl, substituted alkyl, aryl, substituted aryl, heterocyclo, substituted heterocyclo, aralkyl, substituted aralkyl;

or $R^4$ and $R^5$ may together form an optionally substituted monocyclic 5–7 membered saturated or unsaturated carbocyclic or heterocyclic ring, or an optionally substituted bicyclic 7–11 membered saturated or unsaturated heterocyclic ring, except that when Z is O or S, $R^5$ is absent, or when Z is nitrogen, $R^4$ and $R^5$ are not both hydrogen;

$R^6$ is hydrogen, alkyl, substituted alkyl, substituted aryl, heterocyclo, substituted heterocyclo, $NR^7R^8$, $OR^9$ or halogen;

$R^7$ is selected from the group consisting of hydrogen, $C_2$–$C_{20}$ alkyl, substituted alkyl, aryl, substituted aryl, heterocyclo, and substituted heterocyclo, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{21}$, $R^{24}$, $R^{25}$, $R^{26}$, $R^{27}$, $R^{28}$, $R^{29}$, $R^{30}$, $R^{31}$, $R^{32}$, $R^{34}$, $R^{35}$, $R^{36}$, $R^{38}$, $R^{39}$ and $R^{40}$ are independently selected from the group consisting of hydrogen, alkyl, substituted alkyl, aryl, substituted aryl, heterocyclo, and substituted heterocyclo, $R^{22}$, $R^{23}$, $R^{33}$ and $R^{37}$ are independently selected from the group consisting of alkyl, substituted alkyl, aryl, substituted aryl, heterocyclo, and substituted heterocyclo; and $R^{20}$ is selected from the group consisting of hydrogen, lower alkyl and substituted alkyl, or $R^{20}$ is absent if the carbon to which it is attached is part of an unsaturated aryl or heteroaryl ring;

with the provisos that:

a. $R^2$ may not be hydrogen if X is SO, $SO_2$, $NR^{13}CO_2$, or $NR^{14}SO_2$ b. $R^3$ may not be hydrogen if Y is SO, $SO_2$, $NR^{13}CO_2$, or $NR^{14}SO_2$; in combination with pharmaceutically acceptable carrier and an anti-cancer or cytotoxic agent formulated as a fixed dose.

5. The pharmaceutical composition as recited in claim 4, wherein said anticancer or cytotoxic agent is selected from the group consisting of: taxoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teiposide, amsacrine, irinotecan, topotecan and an epothilone.

6. A method for producing an antitangiogenic effect which comprises administering to a warm-blooded species in need thereof, an effective antiangiogenic producing amount of a compound of claim 1.

7. A compound of formula I

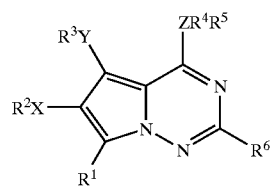

its enantiomers, diastereomers, and pharmaceutically acceptable salts, prodrugs and solvates thereof, wherein X and Y are independently O, OCO, S, SO $SO_2$, CO, $CO_2$, $NR^{10}$, $NR^{11}CO$, $NR^{12}CoNR^{13}$, $NR^{14}CO_2$, $NR^{15}SO_2$, $NR^{16}SO_2NR^{17}$, $SO_2NR^{18}$, $CONR^{19}$, halogen, nitro, cyano, or X or Y are absent;

Z is O, S, N, or $CR^{20}$;

$R^1$ is hydrogen, $CH_3$, OH, $OCH_3$, SH, $SCH_3$, $OCOR^{21}$, $SOR^{22}$, $SO_2R^{23}$, $SO_2NR^{24}R^{25}$, $CO_2R^{26}$, $CoNR^{27}R^{28}$, $NH_2$, $NR^{29}SO_2NR^{30}R^{31}$, $NR^{32}SO_2R^{33}$, $NR^{34} COR^{35}$, $NR^{36}CO_2R^{37}$, $NR^{38}CONR^{39}R^{40}$, halogen, nitro, or cyano;

$R^2$ and $R^3$ are independently hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heterocycloalkyl or substituted heterocycloalkyl, or when X is halo, nitro or cyano $R^2$ is absent or when Y is halo, nitro or cyano $R^3$ is absent;

$R^4$ is heterocyclo or substituted heterocylco, $R^5$ is hydrogen, alkyl, substituted alkyl, aryl, substituted aryl, heterocyclo, substituted heterocyclo, aralkyl, or substituted aralkyl;

except that when Z is O or S, $R^5$ is absent;

$R^6$ is hydrogen, alkyl, substituted alkyl, substituted aryl, heterocyclo, substituted heterocyclo, $NR^7R^8$, $OR^9$ or halogen;

$R^7$ is selected from the group consisting of hydrogen, $C_2$–$C_{20}$ alkyl, substituted alkyl, aryl, substituted aryl, heterocyclo, and substituted heterocyclo, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{21}$, $R^{24}$, $R^{25}$, $R^{26}$, $R^{27}$, $R^{28}$, $R^{29}$, $R^{30}$, $R^{31}$, $R^{32}$, $R^{34}$, $R^{35}$, $R^{36}$, $R^{38}$, $R^{39}$ and $R^{40}$ are independently selected from the group consisting of hydrogen, alkyl, substituted alkyl, aryl, substituted aryl, heterocyclo, and substituted heterocyclo, $R^{22}$, $R^{23}$, $R^{33}$ and $R^{37}$ are independently selected from the group consisting of alkyl, substituted alkyl, aryl, substituted aryl, heterocyclo, and substituted heterocyclo; and $R^{20}$ is selected from the group consisting of hydrogen, lower alkyl and substituted alkyl, or $R^{20}$ is absent if the carbon to which it is attached is part of an unsaturated aryl or heteroaryl ring;

with the provisos that:

a. $R^2$ may not be hydrogen if X is SO, $SO_2$, $NR^{13}CO_2$, or $NR^{14}SO_2$, b. $R^3$ may not be hydrogen if Y is SO, $SO_2$, $NR^{13}CO_2$, or $NR^{14}SO_2$.

8. The compound of claim 7, wherein $R^4$ is a substituted 7 to 11 membered bicyclic ring system which has at least one heteroatom in at least one carbon atom-containing ring.

9. The compound of claim 8, wherein R4 is substituted indolyl.

* * * * *

UNITED STATES PATENT AND TRADEMARK OFFICE
CERTIFICATE OF CORRECTION

PATENT NO.         : 6,982,265 B1
APPLICATION NO. : 09/573829
DATED                 : January 3, 2006
INVENTOR(S)       : Hunt et al.

It is certified that error appears in the above-identified patent and that said Letters Patent is hereby corrected as shown below:

In column 3, Lines 49-50 "a. $R^2$ may not be hydrogen if X is SO, $SO_2$, $NR^{13}CO_2$, or $NR^{14}SO_2$" should read: -- a. $R^2$ may not be hydrogen if X is SO, $SO_2$, $NR^{14}CO_2$, or $NR^{15}SO_2$ --

In column 3, Lines 51-52 "b. $R^3$ may not be hydrogen if Y is SO, $SO_2$, $NR^{13}CO_2$, or $NR^{14}SO_2$." should read: -- b. $R^3$ may not be hydrogen if Y is SO, $SO_2$, $NR^{14}CO_2$, or $NR^{15}SO_2$ --

In column 100, Line 66 "X and Y are independently O, OCO, S, SO $SO_2$, CO, $CO_2$," should read: -- X and Y are independently O, OCO, S, SO, $SO_2$, CO, $CO_2$, --

In column 101, Lines 14-15 "halo, nitro or cyano $R^2$ is absent or when Y is halo, nitro or cyano $R^3$ is absent;" should read: -- halo, nitro or cyano, $R^2$ is absent; or when Y is halo, nitro or cyano, $R^3$ is absent; --

In column 101, Lines 49-50 "a. $R^2$ may not be hydrogen if X is SO, $SO_2$, $NR^{13}CO_2$, or $NR^{14}SO_2$," should read: -- a. $R^2$ may not be hydrogen if X is SO, $SO_2$, $NR^{14}CO_2$, or $NR^{15}SO_2$, --

In column 101, Lines 51-52 "b. $R^3$ may not be hydrogen if Y is SO, $SO_2$, $NR^{13}CO_2$, or $NR^{14}SO_2$." should read: -- b. $R^3$ may not be hydrogen if Y is SO, $SO_2$, $NR^{14}CO_2$, or $NR^{15}SO_2$. --

In column 106, Line 19 "4-[2,3-Dihydro-5-[(methylamino)sulfonyl]-2-OxO-1H-" should read: -- 4-[2,3-Dihydro-5- [(methylamino)sulfonyl]-2-oxo-1H- --

In column 110, Lines 66-67 "4. A pharmaceutical composition comprising a compound of claim 1 a compound of formula I" should read: -- 4. A pharmaceutical composition comprising a compound of formula I --

In column 111, Lines 28-29 "halo, nitro or cyano $R^2$ is absent or when Y is halo, nitro or cyano $R^3$ is absent;" should read: -- halo, nitro or cyano, $R^2$ is absent; or when Y is halo, nitro or cyano, $R^3$ is absent; --

In column 111, Lines 62-63 "a. $R^2$ may not be hydrogen if X is SO, $SO_2$, $NR^{13}CO_2$, or $NR^{14}SO_2$" should read: -- a. $R^2$ may not be hydrogen if X is SO, $SO_2$, $NR^{14}CO_2$, or $NR^{15}SO_2$ --

UNITED STATES PATENT AND TRADEMARK OFFICE
CERTIFICATE OF CORRECTION

PATENT NO. : 6,982,265 B1
APPLICATION NO. : 09/573829
DATED : January 3, 2006
INVENTOR(S) : Hunt et al.

It is certified that error appears in the above-identified patent and that said Letters Patent is hereby corrected as shown below:

In column 111, Lines 64-52 "b. $R^3$ may not be hydrogen if Y is SO, $SO_2$, $NR^{13}CO_2$, or $NR^{14}SO_2$; in combination with pharmaceutically" should read: -- b. $R^3$ may not be hydrogen if Y is SO, $SO_2$, $NR^{14}CO_2$, or $NR^{15}SO_2$; in combination with pharmaceutically --

In column 112, Line 3 "the group consisting of: taxoxifen, toremifen, raloxifene," should read: --the group consisting of: tamoxifen, toremifen, raloxifene, --

In column 112, Lines 32-33 "X and Y are independently O, OCO, S, SO $SO_2$, CO, $CO_2$, $NR^{10}$, $NR^{11}CO$, $NR^{12}CoNR^{13}$, $NR^{14}CO_2$, $NR^{15}SO_2$," should read: -- X and Y are independently O, OCO, S, SO, $SO_2$, CO, $CO_2$, $NR^{10}$, $NR^{11}CO$, $NR^{12}CONR^{13}$, $NR^{14}CO_2$, $NR^{15}SO_2$, --

In column 112, Line 38 "$SOR^{22}$, $SO_2R^{23}$, $SO_2NR^{24}R^{25}$, $CO_2R^{26}$, $CoNR^{27}R^{28}$," should read: -- $SOR^{22}$, $SO_2R^{23}$, $SO_2NR^{24}R^{25}$, $CO_2R^{26}$, $CONR^{27}R^{28}$, --

In column 112, Lines 47-48 "halo, nitro or cyano $R^2$ is absent or when Y is halo, nitro or cyano $R^3$ is absent;" should read: --halo, nitro or cyano, $R^2$ is absent; or when Y is halo, nitro or cyano, $R^3$ is absent; --

In column 112, Lines 66-67 "substituted heterocyclo, $R^{22}$, $R^{23}$, $R^{33}$, and $R^{37}$ are independently selected from the group consisting of" should read:
     -- substituted heterocyclo,
$R^{22}$, $R^{23}$, $R^{33}$, and $R^{37}$ are independently selected from the group consisting of --

In column 113, Lines 8-9 "a. $R^2$ may not be hydrogen if X is SO, $SO_2$, $NR^{13}CO_2$, or $NR^{14}SO_2$," should read: -- a. $R^2$ may not be hydrogen if X is SO, $SO_2$, $NR^{14}CO_2$, or $NR^{15}SO_2$, --

In column 114, Lines 1-2 "b. $R^3$ may not be hydrogen if Y is SO, $SO_2$, $NR^{13}CO_2$, or $NR^{14}SO_2$." should read: -- b. $R^3$ may not be hydrogen if Y is SO, $SO_2$, $NR^{14}CO_2$, or $NR^{15}SO_2$. --

UNITED STATES PATENT AND TRADEMARK OFFICE
CERTIFICATE OF CORRECTION

PATENT NO. : 6,982,265 B1
APPLICATION NO. : 09/573829
DATED : January 3, 2006
INVENTOR(S) : Hunt et al.

It is certified that error appears in the above-identified patent and that said Letters Patent is hereby corrected as shown below:

In column 114, Line 6 "9. The compound of claim 8, wherein R4 is substituted" should read: --9. The compound of claim 8, wherein $R^4$ is substituted --

Signed and Sealed this

Nineteenth Day of June, 2007

JON W. DUDAS
*Director of the United States Patent and Trademark Office*